United States Patent
Day et al.

(10) Patent No.: US 10,160,705 B2
(45) Date of Patent: Dec. 25, 2018

(54) CLASS OF HDAC INHIBITORS EXPANDS THE RENAL PROGENITOR CELLS POPULATION AND IMPROVES THE RATE OF RECOVERY FROM ACUTE KIDNEY INJURY

(75) Inventors: Billy W. Day, Pittsburgh, PA (US); Neil Hukriede, Allison Park, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 742 days.

(21) Appl. No.: 13/982,512

(22) PCT Filed: Feb. 10, 2012

(86) PCT No.: PCT/US2012/024625
§ 371 (c)(1),
(2), (4) Date: Nov. 12, 2013

(87) PCT Pub. No.: WO2012/109527
PCT Pub. Date: Aug. 16, 2012

(65) Prior Publication Data
US 2014/0081054 A1 Mar. 20, 2014
US 2016/0332943 A9 Nov. 17, 2016

Related U.S. Application Data

(60) Provisional application No. 61/441,560, filed on Feb. 10, 2011.

(51) Int. Cl.
| C07C 29/80 | (2006.01) |
| B01D 15/18 | (2006.01) |
| C07C 317/44 | (2006.01) |
| C07C 323/52 | (2006.01) |
| C07C 323/56 | (2006.01) |
| C07C 323/60 | (2006.01) |
| C07C 323/62 | (2006.01) |
| C07C 229/18 | (2006.01) |

(52) U.S. Cl.
CPC .......... *C07C 29/80* (2013.01); *B01D 15/1821* (2013.01); *C07C 229/18* (2013.01); *C07C 317/44* (2013.01); *C07C 323/52* (2013.01); *C07C 323/56* (2013.01); *C07C 323/60* (2013.01); *C07C 323/62* (2013.01)

(58) Field of Classification Search
CPC .... C07C 229/18; C07C 317/44; C07C 323/62
See application file for complete search history.

(56) References Cited

U.S. PATENT DOCUMENTS

| 6,300,514 B1 * | 10/2001 | Takahashi ............. C07C 317/44 546/342 |
| 6,476,027 B1 | 11/2002 | Villamil et al. |
| 2007/0173527 A1 | 7/2007 | Bressi et al. |

FOREIGN PATENT DOCUMENTS

| JP | 5758663 A | 4/1982 | | |
| WO | 9965495 A1 | 12/1999 | | |
| WO | 0138322 A1 | 5/2001 | | |
| WO | WO 0138322 A1 * | 5/2001 | ........... | C07C 259/06 |
| WO | WO-0138322 A1 * | 5/2001 | ........... | C07C 259/06 |
| WO | 2004046094 A1 | 6/2004 | | |
| WO | 2007107758 A1 | 9/2007 | | |

OTHER PUBLICATIONS

DeGroh, E.D. et al. "Inhibition of Histone Deacetylase Expands the Renal Progenitor Cell Population" J. Am. Soc. Nephrol. 2010, 21, 794-802.*
Patani, G. A.; LaVoie, E.J. "Bioisosterism: A Rational Approach in Drug Design" Chem. Rev. 1996, 96, 3147-3176.*
Medline "Interstitial nephritis" (https://www.nlm.nih.gov/medlineplus/ency/article/000464.htm) updated Sep. 22, 2015, pp. 1-4.*
Imai, N. et al."Inhibition of Histone Deacetylase Activates Side Population Cells in Kidney and Partially Reverses Chronic Renal Injury" Stem Cells 2007, 25, 2469-2475.*
Marson, C.M., et al. "Aromatic Sulfide Inhibitors of Histone Deacetylase Based on Arylsulfinyl-2,4-hexadienoic Acid Hydroxyamides" J. Med. Chem. 2006, 49, 800-805.*
de Groh, E.D. "4-(Phenylthio)Butanoic Acid, A Novel Histone Deacetylase Inhibitor, Stimulates Renal Progenitor Cell Proliferation" PhD dissertation, University of Pittsburgh, publically available Nov. 10, 2011, pp. 1-118.*
"DeGroh dissertation date" (http://d-scholarship.pitt.edu/10308/) p. 1-3.*
Romagnani, P. "From Proteus to Prometheus: Learning from Fish to Modulate Regeneration" J Am Soc Nephrol 21: 726-728, 2010.*
Imai, N. et al. "Inhibition of Histone Deacetylase Activates Side Population Cells in Kidney and Partially Reverses Chronic Renal Injury" Stem Cells 2007, 25, 2469-2475. (Year: 2007).*
Marson, C.M., et al. "Aromatic Sulfide Inhibitors of Histone Deacetylase Based on Arylsulfinyl-2,4-hexadienoic Acid Hydroxyamides" J. Med. Chem. 2006, 49, 800-805 (Year: 2006).*
de Groh, E.D. "4-(Phenylthio)Butanoic Acid, A Novel Histone Deacetylase Inhibitor, Stimulates Renal Progenitor Cell Proliferation" PhD dissertation, University of Pittsburgh, publically available Nov. 10, 2011, pp. 1-118 (Year: 2011).*
"DeGroh dissertation date" (http://d-scholarship.pitt.edu/10308/) p. 1-3 (Year: 2017).*
Romagnani, P. "From Proteus to Prometheus: Learning from Fish to Modulate Regeneration" J Am Soc Nephrol 21: 726-728, 2010. (Year: 2010).*
Abraira, V. E. et al., Changes in Sef Levels Influence Auditory Brainstem Development and Function, The Journal of Neuroscience, Apr. 18, 2007, vol. 27, No. 16, pp. 4273-4282.

(Continued)

*Primary Examiner* — Andrew S Rosenthal
(74) *Attorney, Agent, or Firm* — The Webb Law Firm

(57) ABSTRACT

Compounds and compositions are provided that inhibit histone deacylase activity and which expand renal progenitor cell populations and improve kidney function in a damaged kidney. Methods of use of the compounds and compositions are provided.

16 Claims, 32 Drawing Sheets
Specification includes a Sequence Listing.

(56) References Cited

OTHER PUBLICATIONS

Almo, S. C. et al., Structural genomics of protein phosphatases, J Struct Funct Genomics, 2007, vol. 8, pp. 121-140.

Andersen, C. L. et al., Normalization of real-time quantitative reverse transcription-PCR data: a model-based variance estimation approach to identify genes suited for normalization, applied to bladder and colon cancer data sets, Cancer Res 64, (2004), pp. 5245-5250.

Anderson, R. J. et al., Retinoic acid regulation of renal tubular epithelial and vascular smooth muscle cell function, J Am Soc Nephrol 9, (1998), pp. 773-781.

Argiles, A. et al., Retinoic acid affects the cell cycle and increases total protein content in epithelial cells, Kidney Int 36, (1989), pp. 954-959.

Atilgan, A. R. et al., Anisotropy of Fluctuation Dynamics of Proteins with an Elastic Network Model, Biophysical Journal, Jan. 2001, vol. 80, pp. 505-515.

Bacallo, R. et al., Molecular events in the organization of renal tubular epithelium: from nephrogenesis to regeneration, Am J Physiol 257, (1989), pp. F913-F924.

Bahar, I et al., Intrinsic Enzyme Dynamics in the Unbound State and Relation to Allosteric Regulation, Curr. Opin. Struct Biol, Dec. 2007, vol. 17, No. 6, pp. 633-640.

Bakan, A. et al., Toward a Molecular Understanding of the Interaction of Dual Specificity Phosphatases with Substrates: Insights from Stucture-Based Modeling and High Throughput Screening, Current Medicinal Chemistry, 2008, vol. 15, pp. 2536-2544.

Balasubramanian, S. et al. Isoform-specific histone deacetylase inhibitors: The next step?, Cancer Lett 280, (2009), pp. 211-221.

Bi, B. et al., Stromal cells protect against acute tubular injury via an endocrine effect, J Am Soc Nephrol. 2007; 18(9):2486-96.

Bieliauskas, A. V. et al., Isoform-selective histone deacetylase inhibitors, Chem Soc Rev 37, (2008), pp. 1402-1413.

Blumberg, B. et al., An essential role for retinoid signaling in anteroposterior neural patterning, Development 124, (1997), pp. 373-379.

Bolden, J. E. et al., Anticancer activities of histone deacetylase inhibitors, Nat Rev Drug Discov 5, (2006), pp. 769-784.

Boner G. et al., Combination Antihypertensive Therapy in the Treatment of Diabetic Nephropathy, Diabetes Technol Ther 2002;4(3):313-321.

Bradner, J. E. et al., Chemical phylogenetics of histone deacetylases, Nat Chem Biol 6, (2010), pp. 238-243.

Brewster, M.E. et al., Cyclodextrins as pharmaceutical solubilizers, Advanced Drug Delivery Reviews 59:645-666 (2007).

Brown, J. L. et al., Transcriptional profiling of endogenous germ layer precursor cells identifies dusp4 as an essential gene in zebrafish endoderm specification, Proc Natl Acad Sci, Aug. 26, 2008, vol. 105, No. 34, pp. 12337-12342.

Buchwald, M. et al., HDACi—Targets beyond chromatin, Cancer Lett 280, (2009), pp. 160-167.

Butler, K. V. et al., Chemical Origins of Isoform Selectivity in Histone Deacetylase Inhibitors, Curr Pharm Des 14, (2008), pp. 505-528.

Camps, M. et al., Catalytic Activation of the Phosphatase MKP-3 by ERK2 Mitogen-Activated Protein Kinase, Science, May 22, 1998, vol. 280, pp. 1262-1265.

Cartry, J. et al., Retinoic acid signalling is required for specification of pronephric cell fate, Dev Biol 299, (2006), pp. 35-51.

Chen, P. et al., Discordance between the Binding Affinity of Mitogen-activated Protein Kinase Subfamily Members for MAP Kinase Phosphatase-2 and Their Ability to Activate the Phosphatase Catalytically, The Journal of Biological Chemistry, Aug. 3, 2001, vol. 276, No. 31, pp. 29440-29449.

Chen, J. et al., Zebrafish tinman homolog demarcates the heart field and initiates myocardial differentiation, Development, 1996, vol. 122, pp. 3809-3816.

Chen, J. et al., Genetics of heart development, TIG, Sep. 2000, vol. 16, No. 9, pp. 383-388.

Cianciolo Cosenitino, C. et al., (2010) Intravenous Microinjections of Zebrafish Larvae to Study Acute Kidney Injury, JoVE Aug. 4 (42).

Cole, J. et al., Profiling the Isomerization of Biologically Relevant (E)-(Z) Isomers by Supercritical Fluid Chromatography (SFC), Modern Medicine, Jun. 1, 2009, pp. 1-6.

Dailey, L. et al., Mechanisms underlying differential responses to FGF signaling, Cytokine & Growth Factor Reviews, 2005, vol. 16, pp. 233-247.

De Groh, E. D. et al., Inhibition of Histone Deacetylase Expands the Renal Pprogenitor Cell Population, J Am Soc Nephrol 21, (2010), pp. 794-802.

Doi K. et al., Animal models of sepsis and sepsis-induced kidney injury, J Clin Invest. 2009; 119(10):2868-78.

Dowd, S. et al., Isolation of the human genes encoding the Pyst1 and Pyst2 phosphatases: characterisation of Pyst2 as a cytosolic dual-specificity MAP kinase phosphatase and its catalytic activation by both MAP and SAP kinases, Journal of Cell Science, 1998, vol. 111, pp. 3389-3399.

Drummond, I. A., Kidney Development and Disease in the Zebrafish, J Am Soc Nephrol 16, (2005), pp. 299-304.

Ducruet, A. P. et al., Dual Specificity Protein Phosphatases: Therapeutic Targets for Cancer and Alzheimer's Disease, Annu. Rev. Med., 2005, vol. 45, pp. 725-750.

Ekker, M. et al., Coordinate embryonic expression of three zebrafish engrailed genes, Development, 1992, vol. 116, pp. 1001-1010.

Eyal, E. et al., Anisotropic network model: systematic evaluation and a new web interface, Bioinformatics, 2006, vol. 22, No. 21, pp. 2619-2627.

Fürthauer, M. et al., sprouty4 acts in vivo as a feedback-induced antagonist of FGF signaling in zebrafish, Development, 2001, vol. 128, pp. 2175-2186.

Gurtner, G. C. et al., Wound repair and regeneration, Nature, May 15, 2008, vol. 453, pp. 314-321.

Haggarty, S. J. et al., Domain-selective small-molecule inhibitor of histone deacetylase 6 (HDAC6)-mediated tubulin deacetylation, Proc Natl Acad Sci USA 100, (2003), pp. 4389-4394.

Harris, W. A. et al., Neuronal Determination without Cell Division in Xenopus Embryos, Neuron 6, (1991), pp. 499-515.

Hassner, A. et al., The Chemistry of Derivatives of 2-Benzaltetralone. II. Absorption Spectra and Stereostructure, J Am Soc Chem, Feb. 20, 1958, vol. 80, pp. 893-900.

Hubbert, C. et al., HDAC6 is a microtubule-associated deacetylase, Nature 417, (2002), pp. 455-458.

Huey, R. et al., A Semiempirical Free Energy Force Field with Charge-Based Desolvation, J Comput Chem, 2007, vol. 28, pp. 1145-1152.

Imai, N. et al., Inhibition of Histone Deacetylase Activates Side Population Cells in Kidney and Partially Reverses Chronic Renal Injury, Stem Cells 25, (2007), pp. 2469-2475.

Isin, B. et al., Mechanism of Signal Propagation upon Retinal Isomerization: Insights from Molecular Dynamics Simulations of Rhodopsin Restrained by Normal Modes, Biophysical Journal, Jul. 2008, vol. 95, pp. 789-803.

Jacobsen, F. E., et al., The Design of Inhibitors for Medicinally Relevant Metalloproteins, ChemMedChem 2, (2007), pp. 152-171.

Jeong, D. G. et al., Crystal Structure of the Catalytic Domain of Human MAP Kinase Phosphatase 5: Structural Insight into Constitutively Active Phosphatase, J. Mol. Biol., 2006, vol. 360, pp. 946-955.

Jeong, D. G. et al., Crystal Structure of the Catalytic Domain of Human DUSP5, a Dual Specificity MAP Kinase Protein Phosphatase, Proteins, 2007, vol. 66, pp. 253-258.

Jones, G. et al., Molecular Recognition of Receptor Sites using a Genetic Alogorithm with a Description of Desolvation, J. Mol. Biol., 1995, vol. 245, pp. 43-53.

Jones, G. et al., Development and Validation of a Genetic Algorithm for Flexible Docking, J. Mol. Biol., 1997, vol. 267, pp. 727-748.

Keegan, B. R. et al., Organization of cardiac chamber progenitors in the zebrafish blastula, Development, 2004, vol. 131, pp. 3081-3091.

Keegan, B. R. et al. Retinoic Acid Signaling Restricts the Cardiac Progenitor Pool, Science 307, (2005), pp. 247-249.

(56) References Cited

OTHER PUBLICATIONS

Kennedy, S. E. et al., Murine renal ischaemia-reperfusion injury, Nephrology (Carlton). 2008; 13(5):390-6.
Khan, N. et al., Determination of the class and isoform selectivity of small-molecule histone deacetylase inhibitors, Biochem J 409, (2008), pp. 581-589.
Kimmel, C. B. et al., Stages of Embryonic Development of the Zebrafish, Dev Dyn 203(3), (1995), pp. 253-310.
Kudoh, T. et al., A Gene Expression Screen in Zebrafish Embryogenesis, Genome Research, 2001, vol. 11, pp. 1979-1987.
Latinkić, B. V. et al., The Xenopus Brachyury promoter is activated by FGF and low concentrations of activin and suppressed by high concentrations of activin and by paired-type homeodomain proteins, Genes & Development, 1997, vol. 11, pp. 3265-3276.
Lazo, J. S. et al., Discovery and Biological Evaluation of a New Family of Potent Inhibitors of the Dual Specificity Protein Phosphatase Cdc25, J. Med. Chem., 2001, vol. 44, pp. 4042-4049.
Lazo, J. S. et al., Novel benzofuran inhibitors of human mitogen-activated protein kinase phosphatase-1, Bioorganic & Medicinal Chemistry, 2006, pp. 5643-5650, vol. 14.
Lazo, J. S. et al., Structurally Unique Inhibitors of Human Mitogen-Activated Protein Kinase Phosphatase-1 Identified in a Pyrrole Carboxamide Library, The Journal of Pharmacology and Experimental Therapeutics, 2007, vol. 322, No. 3, pp. 940-947.
Lepilina, A. et al., A Dynamic Epicardial Injury Response Supports Progenitor Cell Activity during Zebrafish Heart Regeneration, Cell, Nov. 3, 2006, vol. 127, pp. 607-619.
Li, C. et al., Dusp6(Mkp3) is a negative feedback regulator of FGF stimulated ERK signaling during mouse development, Development, Jan. 2007, vol. 134, No. 1, pp. 167-176.
Liao, E. C. et al., SCL/Tal-1 transcription factor acts downstream of cloche to specify hematopoietic and vascular progenitors in zebrafish, Genes & Development, 1998, vol. 12, pp. 621-626.
Lipinski, C. A. et al., Experimental and computational approaches to estimate solubility and permeability in drug discovery and development settings, Adv Drug Deliv Rev 46, (2001), pp. 3-26.
Loftsson, T. et al., Self-Association of Cyclodextrins and Cyclodextrin Complexes, J. Pharm. Sci. 93(5):1091-1099 (2004).
Loftsson, T. et al., Cyclodextrins in Drug Delivery, Expert. Opin. Drug Deliv. 2:335-351 (2005).
Lovell, S. C. et al., The Penultimate Rotamer Library, Proteins, 2000, vol. 40, pp. 389-408.
Mackerell, A. D., Jr. et al., All-Atom Empirical Potential for Molecular Modeling and Dynamics Studies of Proteins, J. Phys. Chem. B, 1998, vol. 102, pp. 3586-3616.
Maillet, M. et al., DUSP6 (MKP3) Null Mice Show Enhanced ERK1/2 Phosphorylation at Baseline and Increased Myocyte Proliferation in the Heart Affecting Disease Susceptibility, The Journal of Biological Chemistry, Nov. 7, 2008, vol. 283, No. 45, pp. 31246-31255.
Mandl, M. et al., Specific Inactivation and Nuclear Anchoring of Extracellular Signal-Regulated Kinase 2 by the Inducible Dual-Specificity Protein Phosphatase DUSP5, Molecular and Cellular Biology, Mar. 2005, vol. 25, No. 5, pp. 1830-1845.
Mark, J. K. et al., Over-expression and refolding of MAP kinase phosphatase 3, Protein Expression & Purification, 2007, vol. 54, pp. 253-260.
Marques, S. R. et al., Reiterative roles for FGF signaling in the establishment of size and proportion of the zebrafish heart, Dev. Biol, Sep. 15, 2008, vol. 321 No. 2, pp. 397-406.
Martin, Y. C. et al., Examination of the Utility of the Topliss Schemes for Analog Synthesis, J Med Chem. 1973;16(5):578-9.
Martínez, A. et al., Studies on the chemistry of 2-(2-oxo-3-phenylpropyl)-benzaldehydes: novel total synthesis of 3-phenylnaphthalen-2-ols and 2-hydroxy-3-phenyl-1,4-naphthoquinones, Tetrahedron, 2005, vol. 61, pp. 485-492.
Marumo, T. et al., Epigenetic Regulation of BMP7 in the Regenerative Response to Ischemia, J Am Soc Nephrol 19, (2008), pp. 1311-1320.

Maury, G. et al., Mobile Keto Allyl Systems. VI. Reaction of 3-Bromo-2-benzal-1-indanone with Amines, The Journal of Organic Chemistry, May 1968, vol. 33, No. 5, pp. 1900-1907.
Maves, L. et al., FGF3 and FGF8 mediate a rhombomere 4 signaling activity in the zebrafish hindbrain, Development, 2002, vol. 129, pp. 3825-3837.
Menegola, E. et al., Inhibition of Histone Deacetylase as a New Mechanism of Teratogenesis, Birth Defects Res C Embryo Today 78, (2006), pp. 345-353.
Mitamura, T. et al., Diphtheria Toxin Binds to the Epidermal Growth Factor (EGF)-like Domain of Human Heparin-binding EGF-like Growth Factor/Diphtheria Toxin Receptor and Inhibits Specifically Its Mitogenic Activity, J Biol Chem 270, (1995), pp. 1015-1019.
Molina, G. A. et al., Generation of FGF reporter transgenic zebrafish and their utility in chemical screens, BMC Developmental Biology, 2007, vol. 7, No. 62, pp. 1-14.
Molina, G. et al., Zebrafish chemical screening reveals an inhibitor of Dusp6 that expands cardiac cell lineages, Nat Chem Biol 5, (2009), pp. 680-687.
Morris, G. M. et al., Automated Docking Using a Lamarckian Genetic Algorithm and an Empirical Binding Free Energy Function, Journal of Computational Chemistry, 1998, vol. 19, No. 14, pp. 1639-1662.
Mundel, P. et al., Rearrangements of the Cytoskeleton and Cell Contacts Induce Process Formation During Differentiation of Conditionally Immortalized Mouse Podocyte Cell Lines, Exp Cell Res 236, (1997), pp. 248-258.
Murray, R. J. et al., Mobile Keto Allyl Systems. 18. Synthesis and Charge-Transfer Interactions of 2-(alpha Aminobenzyl)-1-indenones, J. Org. Chem., 1976, vol. 41, No. 22, pp. 3540-3545.
Noel, E. S. et al., Organ-specific requirements for Hdac1 in liver and pancreas formation, Dev Biol 322, (2008), pp. 237-250.
North, T. E. et al., Prostaglandin E2 regulates vertebrate haematopoietic stem cell homeostasis, Nature, Jun. 21, 2007, vol. 447, pp. 1007-1011.
Owens, D. M. et al., Differential regulation of MAP kinase signalling by dual-specificity protein phosphatases, Oncogene, 2007, vol. 26, pp. 3203-3213.
Oxtoby, E. et al., Cloning of the zebrafish krox-20 gene (krx-20) and its expression during hindbrain development, Nucleic Acids Research, 1993, vol. 21, No. 5, pp. 1087-1095.
Pearson, B. D. et al., Elimination Reactions of alpha-Halogenated Ketones. IX . A Comparison of the Reactions of 2-Bromo-2-(alpha-bromobenzyl)-1-indanone with Those of 2-Bromo-2-( alpha-bromobenzyl)-3,3-dimethyl-1-indanone, J. Org. Chem., Sep. 1962, vol. 27, pp. 3038-3044.
Peterson, R. T. et al., Small molecule developmental screens reveal the logic and timing of vertebrate development, Proc Natl Acad Sci USA, Nov. 21, 2000, vol. 97, No. 24, pp. 12965-12969.
Pham, V. N. et al., Combinatorial function of ETS transcription factors in the developing vasculature, Dev Biol., Mar. 15, 2007, vol. 303, No. 2, pp. 772-783.
Phillips, J. C. et al., Scalable Molecular Dynamics with NAMD, J Comput Chem., Dec. 2005, vol. 26, No. 16, pp. 1781-1802.
Picker, A. et al., A novel positive transcriptional feedback loop in midbrain-hindbrain boundary development is revealed through analysis of the zebrafish pax2.1 promoter in transgenic lines, Development 2002 129 (13): pp. 3227-3239.
Pohl, L. R. et al., Electrophilic halogens as potentially toxic metabolites of halogenated compounds, Trends Pharm Sci 5, (1984), pp. 61-64.
Popa-Burke, I. G. et al., Streamlined System for Purifying and Quantifying a Diverse Library of Compounds and the Effect of Compound Concentration Measurements on the Accurate Interpretation of Biological Assay Results, Anal Chem 76, (2004), pp. 7278-7287.
Qian, F. et al., Microarray Analysis of Zebrafish cloche Mutant Using Amplified cDNA and Identification of Potential Downstream Target Genes, Developmental Dynamics, 2005, vol. 233, pp. 1163-1172.
Rasheed, A. et al., Cyclodextrins as Drug Carrier Molecule: A Review, Sci. Pharm. 76:567-598 (2008).

(56) References Cited

OTHER PUBLICATIONS

Reifers, F. et al., Fgf8 is mutated in zebrafish acerebellar (ace) mutants and is required for maintenance of midbrain-hindbrain boundary development and somitogenesis, Development, 1998, vol. 125, pp. 2381-2395.
Reifers, F. et al., Induction and differentiation of the zebrafish heart requires fibroblast growth factor 8 (fgf8/acerebellar), Development, 2000, vol. 127, pp. 225-235.
Remington: The Science and Practice of Pharmacy, 21st edition, ed. Paul Beringer et al., Lippincott, Williams & Wilkins, Baltimore, MD, Easton, PA (2005) Chapters 37, 39, 41, 42, and 45.
Ruijter, J. M. et al., Amplification efficiency: linking baseline and bias in the analysis of quantitative PCR data, Nucleic Acids Res 37, e45, (2009), 12 pages.
Sanderson, L. et al., Plasma pharmacokinetics and metabolism of the histone deacetylase inhibitor trichostatin after intraperitoneal administration to mice, Drug Metab Dispos 32, (2004), pp. 1132-1138.
Schoenebeck, J. J. et al., Vessel and Blood Specification Override Cardiac Potential in Anterior Mesoderm, Developmental Cell, Aug. 2007, vol. 13, pp. 254-326.
Schwartz, E. J. et al., Human Immunodeficiency Virus-1 Induces Loss of Contact Inhibition in Podocytes, J Am Soc Nephrol 12, (2001), pp. 1677-1684.
Slack, D. N. et al., Distinct Binding Determinants for ERK2/p38alpha and JNK MAP Kinases Mediate Catalytic Activation and Substrate Selectivity of MAP Kinase Phosphatase-1, The Journal of Biological Chemistry, May 11, 2001, vol. 276, No. 19, pp. 16491-16500.
Soroldoni, D. et al., Simple and Efficient Transgenesis with Meganuclease Constructs in Zebrafish, Methods Mol Bio 2009; 546: 117-30.
Stewart, A. E. et al., Crystal structure of the MAPK phosphatase Pyst1 catalytic domain and implications for regulated activation, Nature Structural Biology, Feb. 1999, vol. 6, No. 2, pp. 174-181.
Sumanas, S. et al., Identification of novel vascular endothelial-specific genes by the micorarray analysis of the zebrafish cloche mutants, Blood, Jul. 15, 2005, vol. 106, No. 2, pp. 534-541.
Swanhart, L. M. et al., Characterization of an Ihx1a transgenic reporter in zebrafish, Int J Dev Biol 54(4): 731-6 (2010).
Tang, R. et al., Validation of Zebrafish (*Danio rerio*) Reference Genes for Quantitative Real-time RT-PCR Normalization, Acta Biochim Biophys Sin (Shanghai) 39, (2007), pp. 384-390.
Testa, B. et al., Lipophilicity in Molecular Modeling, Pharm Res 13, (1996), pp. 335-343.
Thisse, B. et al., Fast Release Clones: A High Throughput Expression Analysis, ZFIN Direct Data Submission, 2004, 2 pages.
Thisse, B. et al., Functions and regulations of fibroblast growth factor signaling during embryonic development, Developmental Biology, 2005, vol. 287, pp. 390-402.
Traynelis, V. J. et al., Seven-Membered Heterocycles. I. Synthesis of Benzo[b]thiepin 1,1-Dioxide and 1-Phenylsulfony1-4-phenyl-1,3-butadiene, J Org Chem 26, (1961), pp. 2728-2733.
Treibs, von W. et al., Pseudoaromatic compounds from 2-indanones, Justus Liebigs Ann Chem 639, 1961, pp. 204-213.
Tsang, M. et al., Identification of Sef, a novel modulator of FGF signalling, Nature Cell Biology, Feb. 2002, vol. 4, pp. 165-169.
Tsang, M. et al., A role for MKP3 in axial patterning of the zebrafish embryo, Development, Mar. 4, 2004, vol. 131, pp. 2769-2779.
Tsang, M. et al., Promotion and Attenuation of FGF Signaling Through the Ras-MAPK Pathway, Science's Stke, Apr. 14, 2004, pp. 1-5.
Urness, L. D. et al., Expression of ERK signaling inhibitors Dusp6, Dusp7 and Dusp9 during mouse ear development, Dev Dyn., Jan. 2008, vol. 237, No. 1, pp. 163-169.
Villar-Garea, A. et al., Histone deacetylase inhibitors: understanding a new wave of anticancer agents, Int J Cancer 112, (2004), pp. 171-178.
Vogt, A. et al., Chemical complementation: a definitive phenotypic strategy for identifying small molecule inhibitors of elusive cellular targets, Pharmacology & Therapeutics, 2005, vol. 107, pp. 212-221.
Vogt, A. et al., The Benzo[c]phenanthridine Alkaloid, Sanguinarine, Is a Selective, Cell-active Inhibitor of Mitogen-activated Protein Kinase Phosphatase-1, The Journal of Biological Chemistry, May 13, 2005, vol. 280, No. 19, pp. 19078-19086.
Vogt, A. et al., Implementation of high-content assay for inhibitors of mitogen-activated protein kinase phosphatases, Methods, Jul. 2007, vol. 42, No. 3, pp. 268-277.
Vogt, A. et al., High-content analysis of cancer-cell specific apoptosis and inhibition of in vivo angiogenesis by synthetic (−)-pironetin and analogs, Chem Biol Drug Des. 2009;74(4):358-68.
Vogt, A. et al., Automated Image-Based Phenotypic Analysis in Zebrafish Embryos, Dev Dyn. 2009; 238(3):656-663.
Yelon, D. et al., Restricted Expression of Cardiac Myosin Genes Reveals Regulated Aspects of Heart Tube Assembly in Zebrafish, Developmental Biology 1999, vol. 214, pp. 23-37.
Yelon, D. et al., the bHLH transcription factor Hand2 plays parallel roles in zebrafish heart and pectoral fin development, Development, 2000, vol. 127, pp. 2573-2582.
Yelon, D., Cardiac Patterning and Morphogenesis in Zebrafish, Developmental Dynamics, 2001, vol. 222, pp. 552-563.
Yu, P. B. et al., Dorsomorphin inhibits BMP signals required for embryogenesis and iron metabolism, Nat Chem Biol., Jan. 2008, vol. 4, No. 1, pp. 33-41.
Yuen, P. S. T. et al., A simplified method for HPLC determination of creatinine in mouse serum, Am J Physiol Renal Physiol. 2004;286(6):F1116-9.
Zhang, L. et al., Cell cycle progression is required for zebrafish somite morphogenesis but not segmentation clock function, Development 135, (2008), pp. 2065-2070.
Zhou, B. et al., Mapping ERK2-MKP3 Binding Interfaces by Hydrogen/Deuterium Exchange Mass Spectrometry, The Journal of Biological Chemistry, Dec. 15, 2006, vol. 281, No. 50, pp. 38834-38844.
Zon, L. I. et al., In Vivo Drug Discovery in the Zebrafish, Nature Reviews, Jan. 2005, vol. 4, pp. 35-44.
Brizzi, A. et al., "Design, Synthesis, and Binding Studies of New Potent Ligands of Cannabinoid Receptors", J. Med. Chem., 2005, pp. 7343-7350, vol. 48, No. 23.
Carey, FA. Organic Chemistry, 6th Ed., McGraw Hill. 2006, Chapter 1, pp. 8-10.
Marson, CM. et al., "Aromatic Sulfide Inhibitors of Histone Deacetylase Based on Arylsulfiny1-2,4-hexadienoic Acid hlydroxyamides", J. Med. Chem., 2006, pp. 800-805, vol. 49, No. 2.
Van Beneden. K. et al, "HDAC inhibitors in experimental liver and kidney fibrosis", Fibrogenesis & Tissue Repair, 2013, pp. 1-14, vol. 6, No. 1.

\* cited by examiner

CLASS OF HDAC INHIBITORS EXPANDS THE RENAL PROGENITOR CELLS POPULATION AND IMPROVES THE RATE OF RECOVERY FROM ACUTE KIDNEY INJURY

CROSS REFERENCE TO RELATED APPLICATIONS

This application is a 371 of International Patent Application No. PCT/US2012/024625, filed Feb. 10, 2012, which claims the benefit of U.S. Provisional Application No. 61/441,560, filed Feb. 10, 2011, entitled "Class of HDAC Inhibitors Expands the Renal Progenitor Cells Population and Improves the Rate of Recovery from Acute Kidney Injury," which is incorporated herein by reference in its entirety.

STATEMENT REGARDING FEDERAL FUNDING

This invention was made with government support under Grant Nos. DK069403 and DK053287 awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 6527_132648_ST25.txt. The size of the text file is 2,330 bytes, and the text file was created on Jul. 25, 2013.

Severe acute kidney injury (AKI) is remarkably common and has an unacceptably high mortality that has been unchanged for the last twenty years. AKI therapies that have been developed in experimental models when administered prior to the onset of injury have failed to show therapeutic benefit in humans. However, the kidney has an innate capacity to undergo epithelial regeneration following injury, suggesting that drugs that enhance this regenerative capacity are more likely to be of benefit when given after the onset of injury.

AKI is a multi-factorial disorder that occurs in approximately 7% of in-patients hospital admissions. It is an independent predictor of in-hospital mortality. Severe AKI requiring renal replacement therapy occurs in 4% of critically ill patients and has 50% in-patient mortality. Long term follow up studies in survivors of severe AKI indicate that approximately 12.5% become dialysis-dependent. Despite these sobering statistics, renal replacement is the only approved therapy for AKI, and there are no established therapies that have been proven to prevent renal injury or accelerate the rate of renal recovery following induction of AKI in man. Therefore there is an urgent need to develop effective therapies that will accelerate the rate of recovery following induction of renal injury.

SUMMARY

The studies below identify novel, non-toxic therapeutic agents that accelerate recovery from AKI by enhancing the innate regenerative capacity of the kidney, thereby identifying a number of lead compounds with a high probability of targeted translatability for application in human AKI. A state of the art, high content functional screen using transgenic zebrafish embryos was developed to identify compounds that cause expansion of embryonic renal progenitor cells. This strategy was validated by identifying a unique and novel class of histone deacetylase inhibitors (HDACi) that increase the rate of recovery in a mouse model of AKI. These findings point to a promising role for this class of small molecules in patients with AKI.

BRIEF DESCRIPTION OF THE DRAWINGS

FIG. 9. PTBA treatment expands several pronephric regions. (A through F) In situ hybridization for the podocyte marker wt1a (A and B), the proximal tubule marker slc4a4 (C and D) and the distal tubule marker slc12a1 (E and F) in 48 hpf embryos treated with 0.5% DMSO (A, C, and E) or 3 µM PTBA (B, D, and F). Brackets in A and B indicate the expression domain of wt1a.

Figure 28:
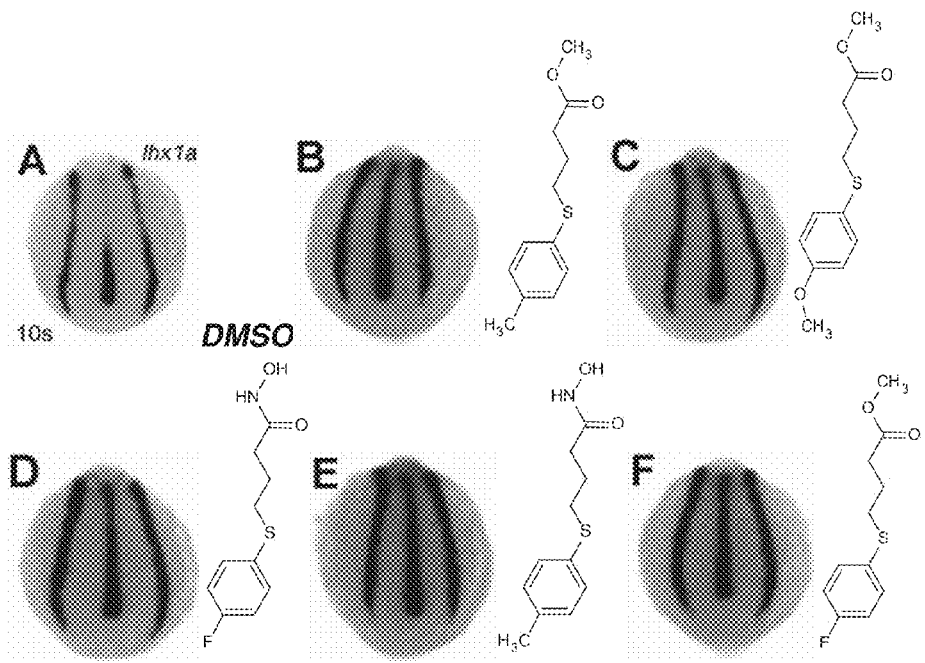

FIG. 28. PTBA analogs exhibiting efficacy at 800 nM. (A through F) In situ hybridization for lhx1a expression in 10-somite embryos treated from 2 hpf with 0.5% DMSO (A) or 800 nM of the following compounds: methyl 4-[(methylphenyl)thio]butanoate (49% expansion) (B), methyl 4-[(methoxyphenyl)thio]butanoate (57% expansion) (C), 4-[(4-fluorophenyl)thio]-N-hydroxybutanamide (60% expansion) (D), N-hydroxy-4[(methylphenyl)thio]butanamide (61% expansion) (E), and methyl 4-[(4-fluorophenyl) thio] butanoate (64% expansion, n=36) (F).

Figure 29:
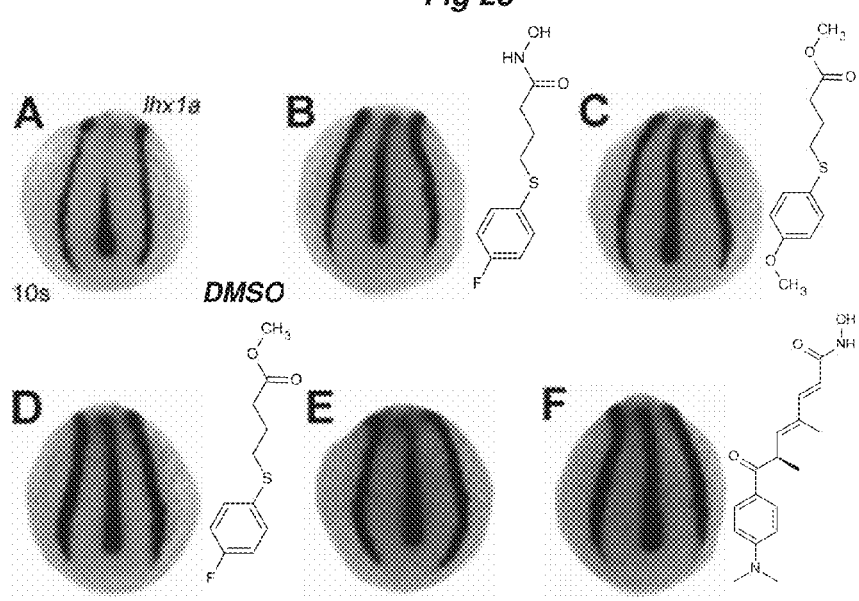

FIG. 29. PTBA analogs exhibiting efficacy at or below 400 nM. (A through F) In situ hybridization for lhx1a expression in 10-somite embryos treated from 2 hpf with 0.5% DMSO (A) or concentrations of the following compounds as indicated: 400 nM 4-[(4-fluorophenyl)thio]-N-hydroxybutanamide (35% expansion) (B), 400 nM methyl 4-[(methoxyphenyl)thio]butanoate (29% expansion) (C), 200 nM methyl 4-[(4-fluorophenyl) thio]butanoate (26% expansion) (D), 400 nM apicidin (22% expansion) (E), and 100 nM TSA (97% expansion) (F).

Figure 30:
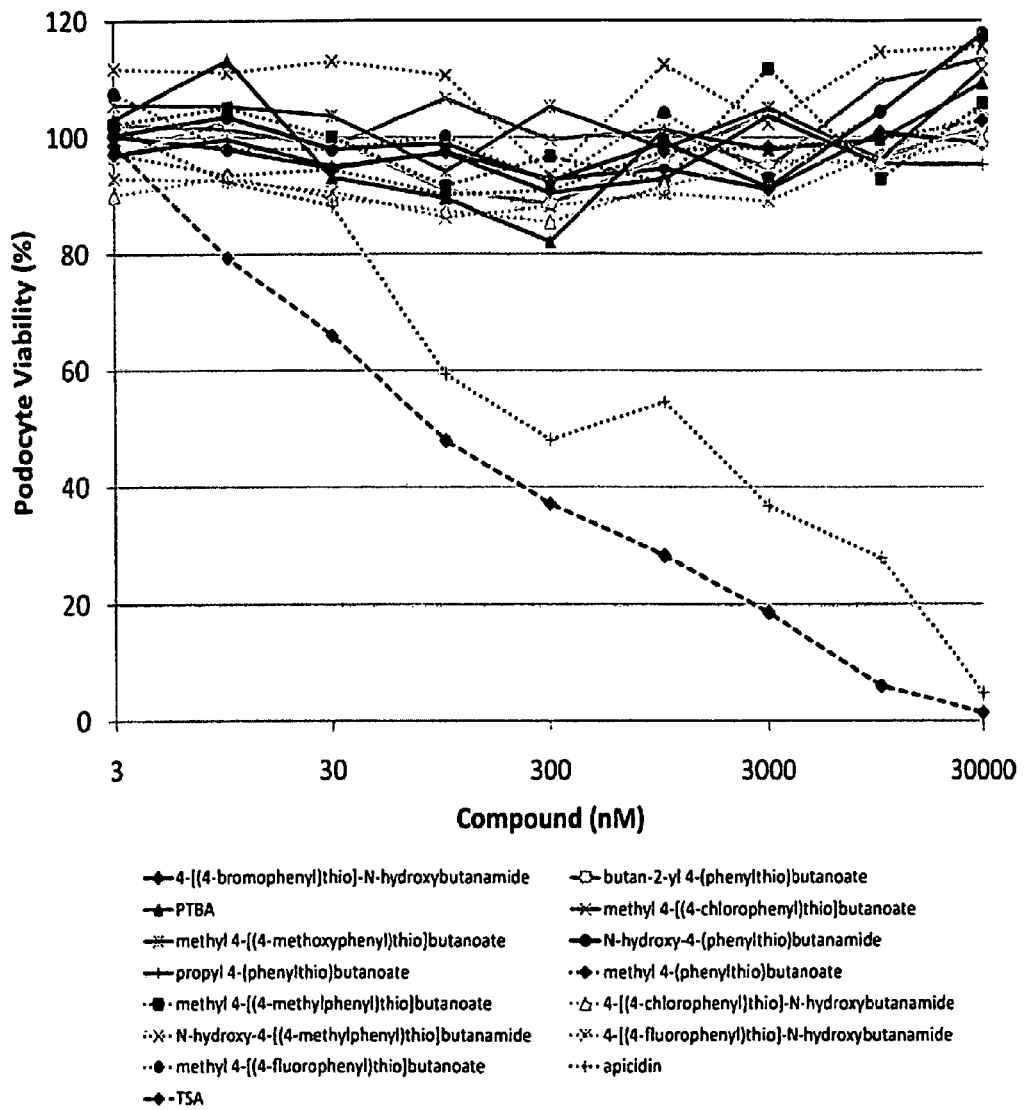

FIG. 30. Structural PTBA analogs exhibit low toxicity in cultured podocytes. Podocytes were treated for 72 hours with 30 µM, 10 µM, 1 µM, 300 nM, 100 nM, 30 nM, 10 nM, or 3 nM of each compound or a DMSO control. Viability was assessed using Cell Titer-Blue. Viability was calculated as a percentage of the DMSO control, which was considered 100% viability. Data represent the average results of three independent experiments using duplicate wells for each condition.

Figure 31:
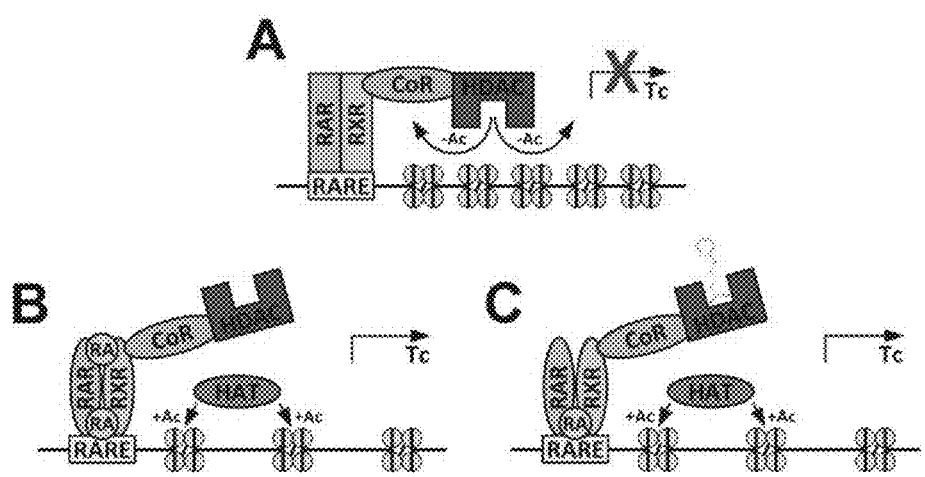

FIG. 31. HDACis enhance RA signaling. (A) In the absence of RA, RAR/RXR dimers recruit a corepressor complex (CoR) containing an HDAC. The HDAC deacetylates nucleosomes, causing chromatin condensation and preventing transcription. (B) In the presence of RA, the RAR/RXR dimer undergoes a conformational change, removing the HDAC from close association with nucleosomes. This allows coactivators such as a histone acetyltransferase (HAT) to acetylate the nucleosomes, which decondenses the chromatin and permits transcription. (C) HDAC inhibitors, such as PTBA, have been hypothesized to decrease the required concentration of RA necessary to trigger the RAR/RXR conformational switch. Figure adapted from Menegola and coworkers (Menegola, E., et al. Inhibition of histone deacetylase as a new mechanism of teratogenesis. Birth Defects Res C Embryo Today 78, 345-353, (2006)).

Figure 32:
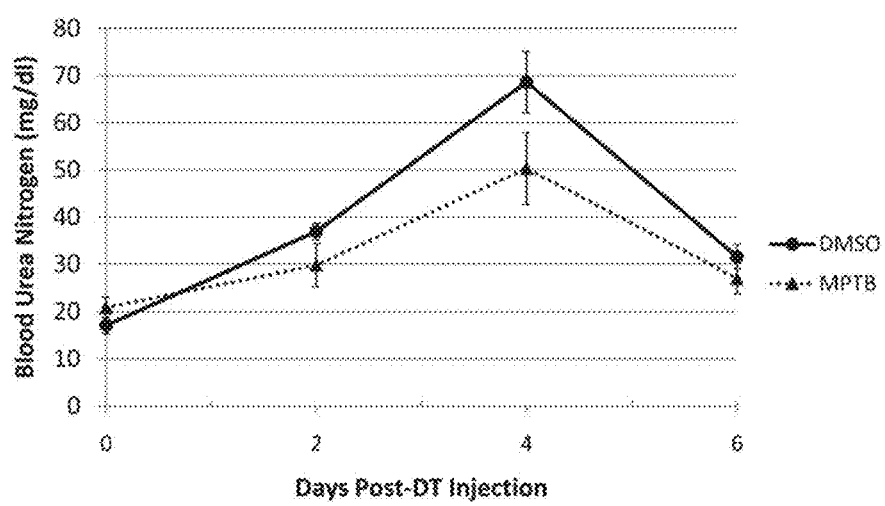

FIG. 32. Treatment with MPTB increases the rate of renal recovery in mice following acute kidney injury. Female PTC-DTR mice were injected with 0.1 µg/kg DT on day 0. Beginning on day 1, mice were treated with daily injections of 1% DMSO or 3.4 mg/kg MPTB (n=5 per group). Blood urea nitrogen (BUN), a biomarker of nitrogenous wastes, was determined every two days following DT injection. Error bars are the standard error of the mean. Asterisk represents a significant difference in BUN concentration (p<0.002) as determined by t-test.

Figure 33:
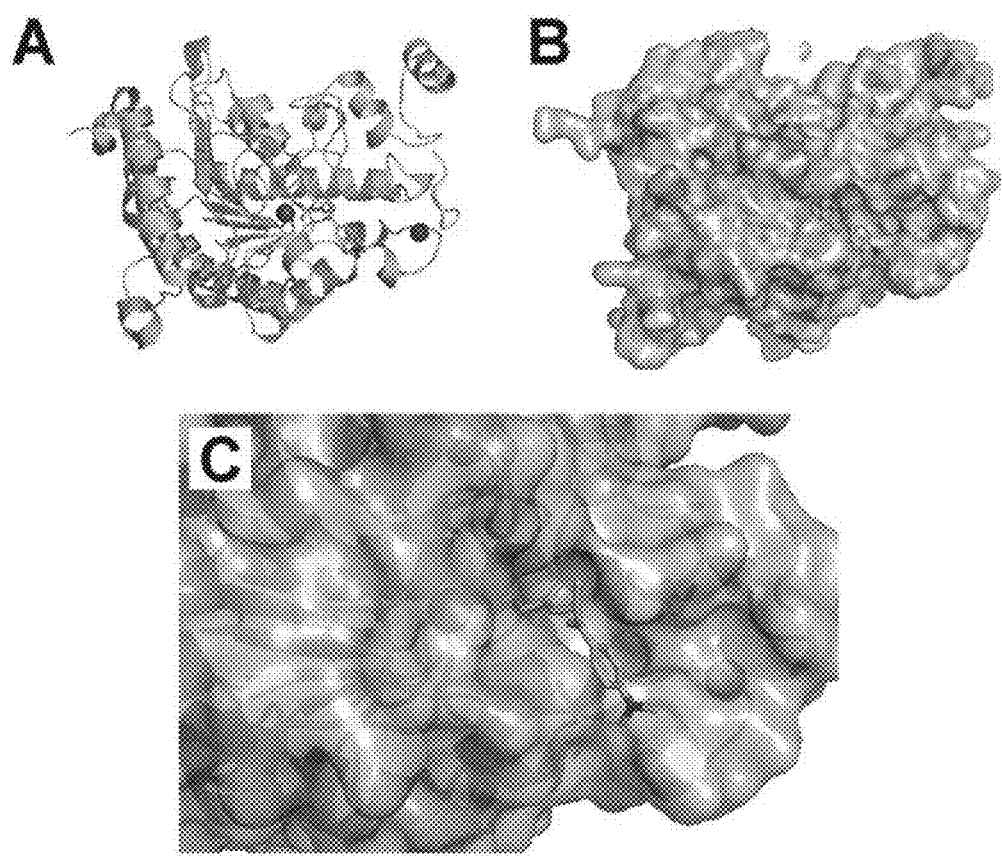

FIG. 33. Binding of TSA to human HDAC7 as determined by X-ray crystallography. (A) TSA co-crystallized with HDAC7 (ribbon model). (B) TSA co-crystallized with HDAC7 (space-filling model). (C) Magnification of (B), showing coordination of the hydroxamic motif of TSA with the catalytic site $Zn^{2+}$.

Figure 34:
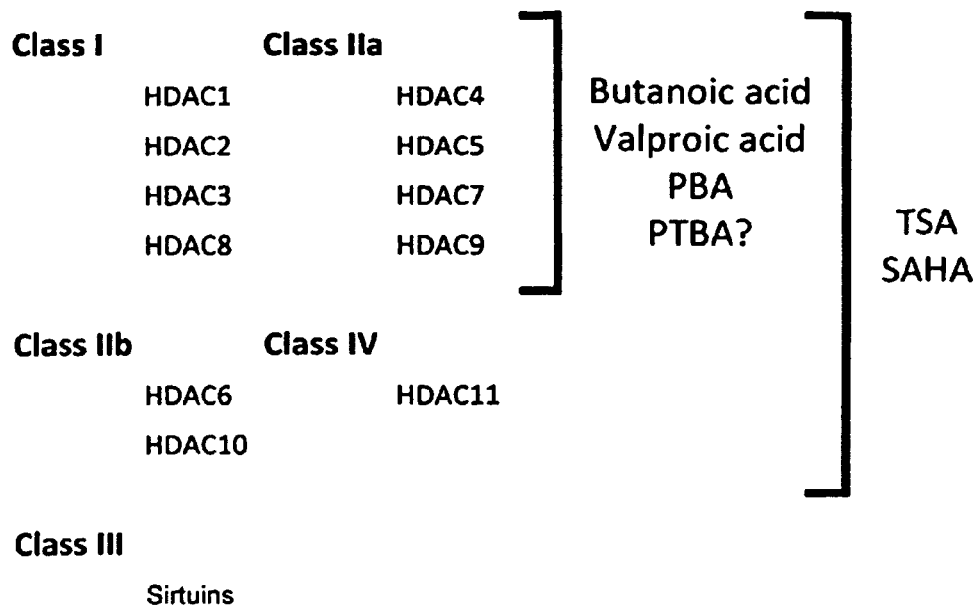

FIG. 34. HDAC classes inhibited by carboxylic and hydroxamic acid HDACis. Carboxylic acid HDACis: butanoic acid, valproic acid, PBA, and TSA. Hydroxamic acid HDACis: TSA and SAHA. Class I, II, and IV HDACs utilize $Zn^{2+}$-dependent catalysis, while the Class III sirtuins employ an NAD+-dependent mechanism.

Figure 35:
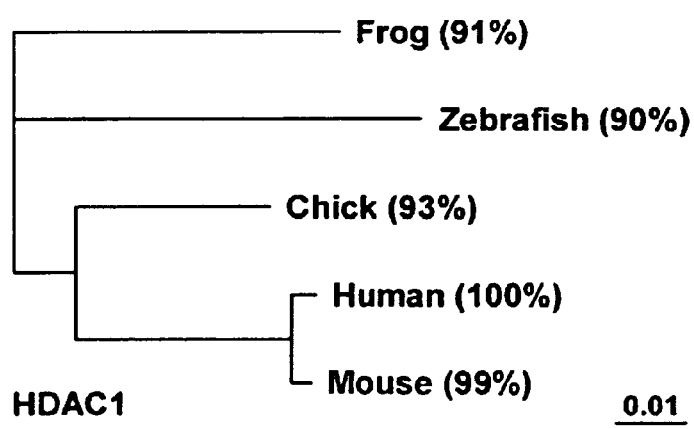

FIG. 35. Evolutionary relationship between HDAC1 orthologs in selected vertebrates. Cladogram generated using TreeView software (ver. 1.6.6) and HDAC1 RefSeq protein sequences for each species. Percentage denotes percent sequence identity with the human isoform. Scale bar represents nucleotide substitutions per site.

Figure 36:
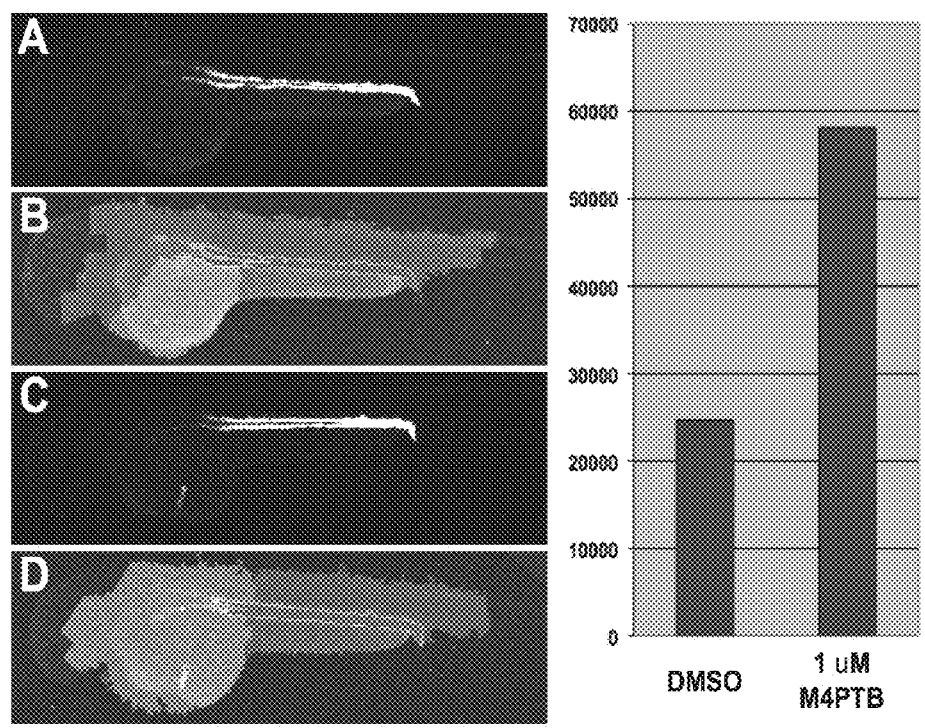

FIG. 36. Image based high-content screen. Tg(cad17: EGFP) zebrafish embryos arrayed in 96-well plates and the size of the fluorescently labeled kidney field quantified fish treated with the PTBA analogue, m4PTB. A/C shows GFP images in larvae at 56 hours; B/D show corresponding CNT image analysis. Bar graph shows quantification of the identified renal field (red).

Figure 37:
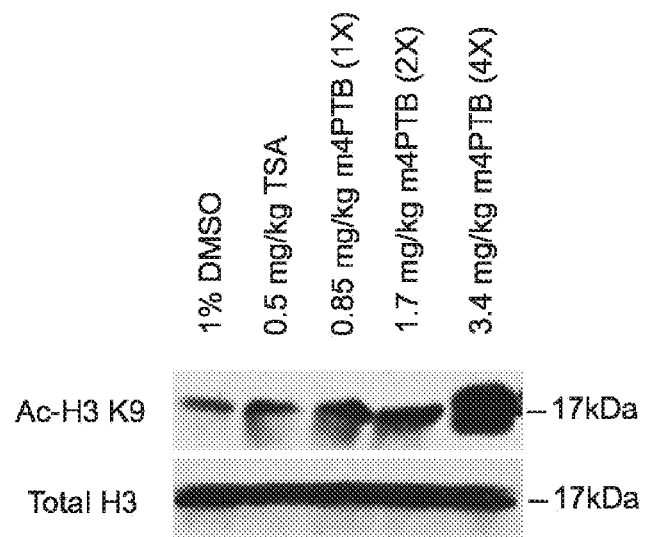

FIG. 37. Renal histone acetylation after treatment with m4PTB. CD1 mice injected S/C with the indicated doses of TSA or m4PTB, were sacrificed after 24 hours, and Ac—H3 K9 evaluated in kidney nuclear extracts by Western blot. Total H3 provides control for histone loading.

Figure 38:
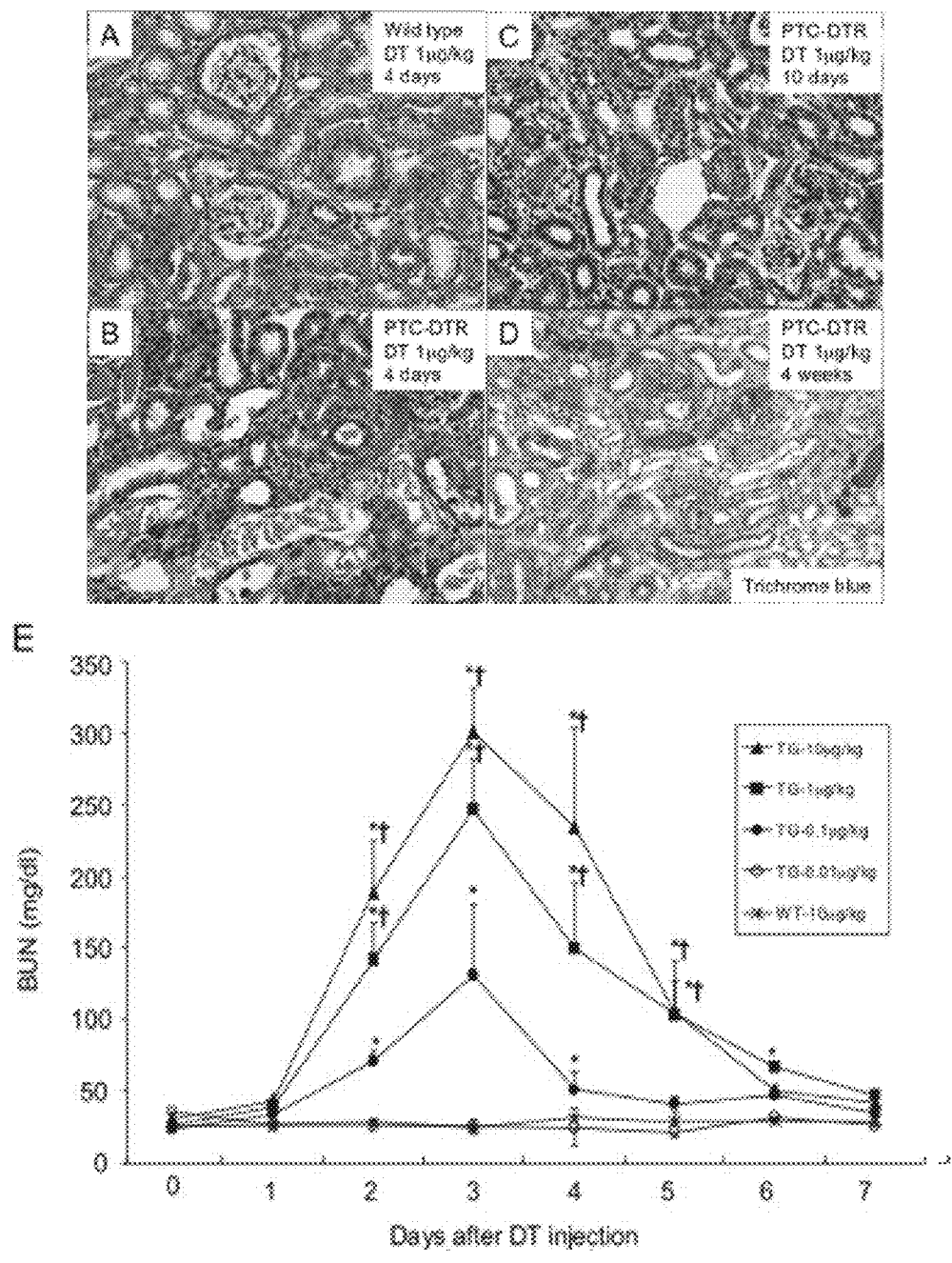

FIG. 38. Mouse model of AKI. Diphtheria toxin (DT) injected at day 0 in wild type and PTC-DTR mice (male). A-D, Renal histology at different time points after injection of 1 µg/kg DT. Trichrome blue stain showing collagen deposition after 4 weeks (D). (E) BUN time course after different doses of DT in wild type and PTC-DTR mice. Mean+/−SD BUN measurements (6 mice per group). T-test, p<0.01*vs. wild type control, +vs. 0.1 µg/kg DT.

Figure 39A:
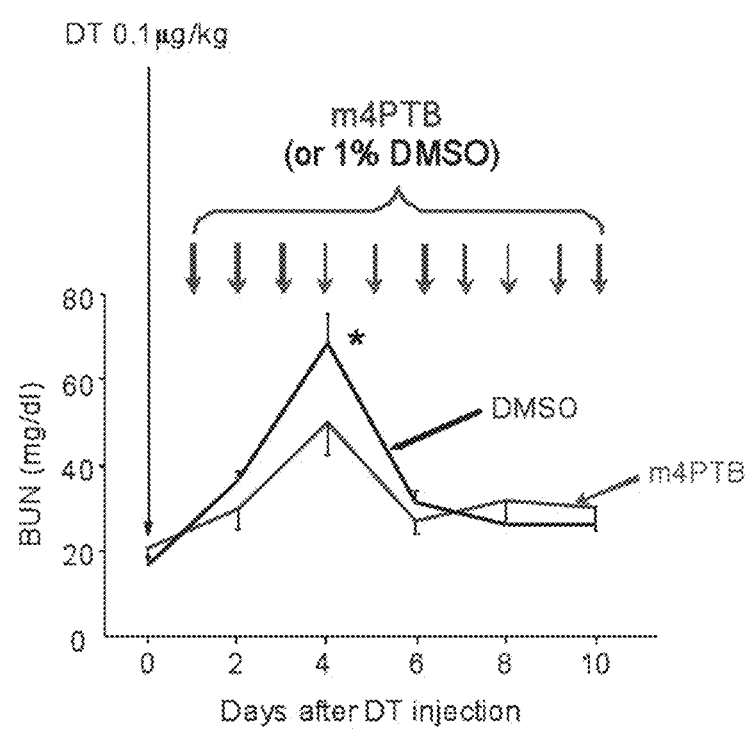
Figure 39B:
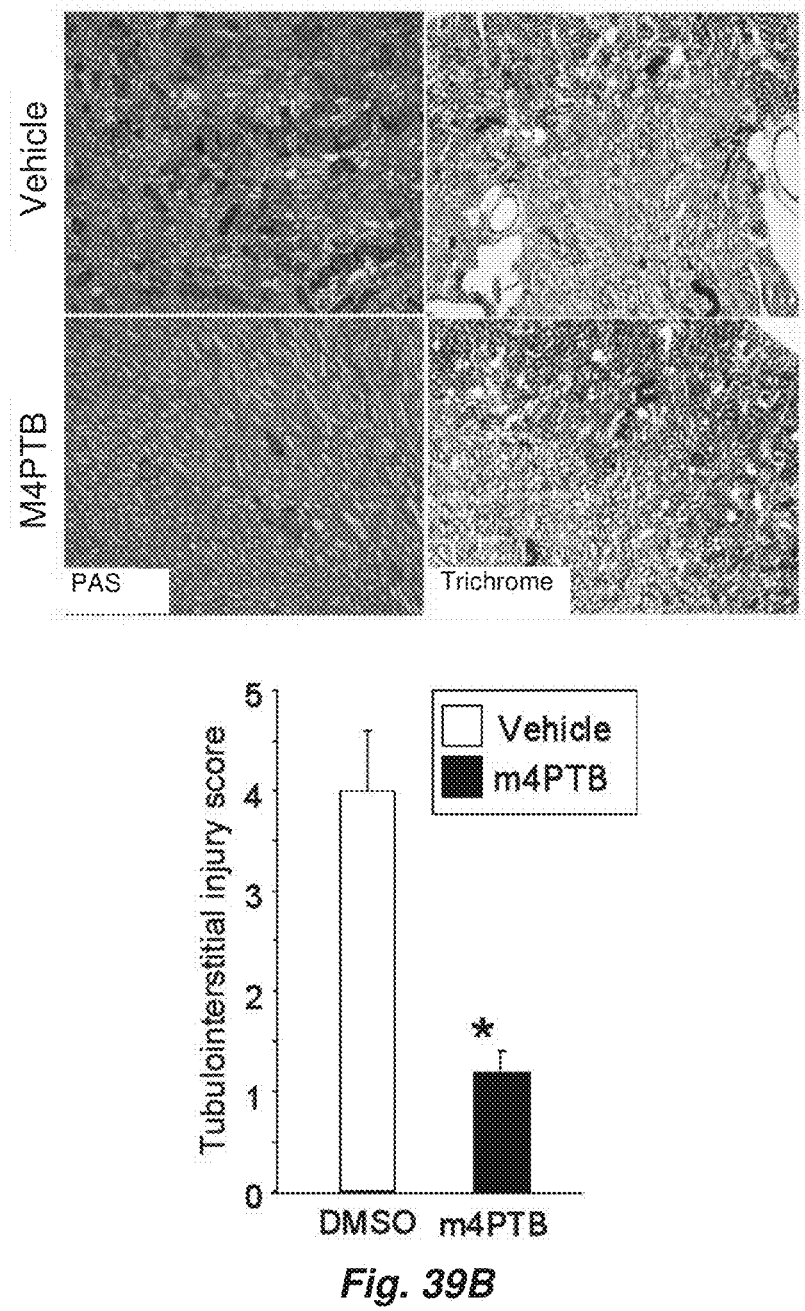

FIG. 39. Effect of post-treatment with m4PTB on AKI. Female PTC-DTR mice injected with 0.1 µg/kg DT injected and treated 24 hrs later with daily injections of 3.4 mg/kg m4PTB or DMSO control. (n=5 per group). (A) Renal function. Mean+/−SEM BUN, ANOVA, p<0.05, *DMSO vs. m4PTB; (B) Renal fibrosis. PAS and Trichrome staining of kidneys illustrating areas of tubulointerstitial fibrosis and tubular atrophy. Quantification of tubulointerstitial injury score (0-5, blinded analysis). Mean+/−SEM, T-Test p<0.002, *DMSO (vehicle) vs. m4PTB.

FIG. 40. Graphs showing $EC_{50}$s for PTBA (A) and m4PTB (B) done via CNT analysis.

Figure 41:
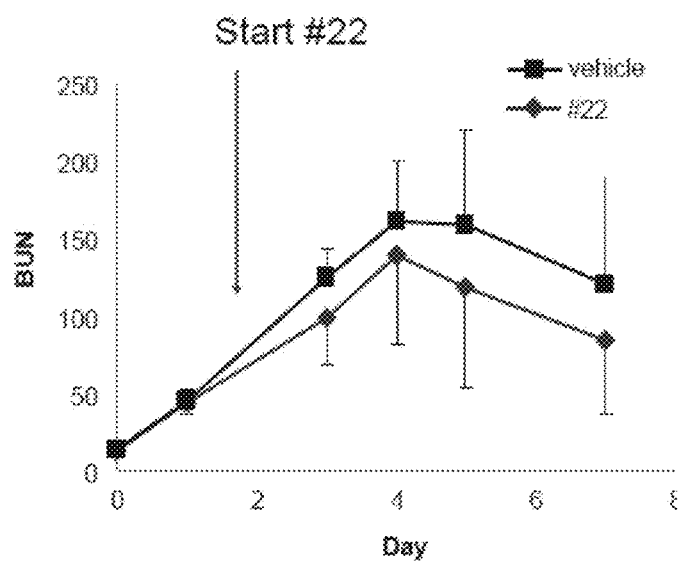

FIG. 41. Graph showing the results of an AKI model using $HgCl_2$ induced injury.

Figure 42:
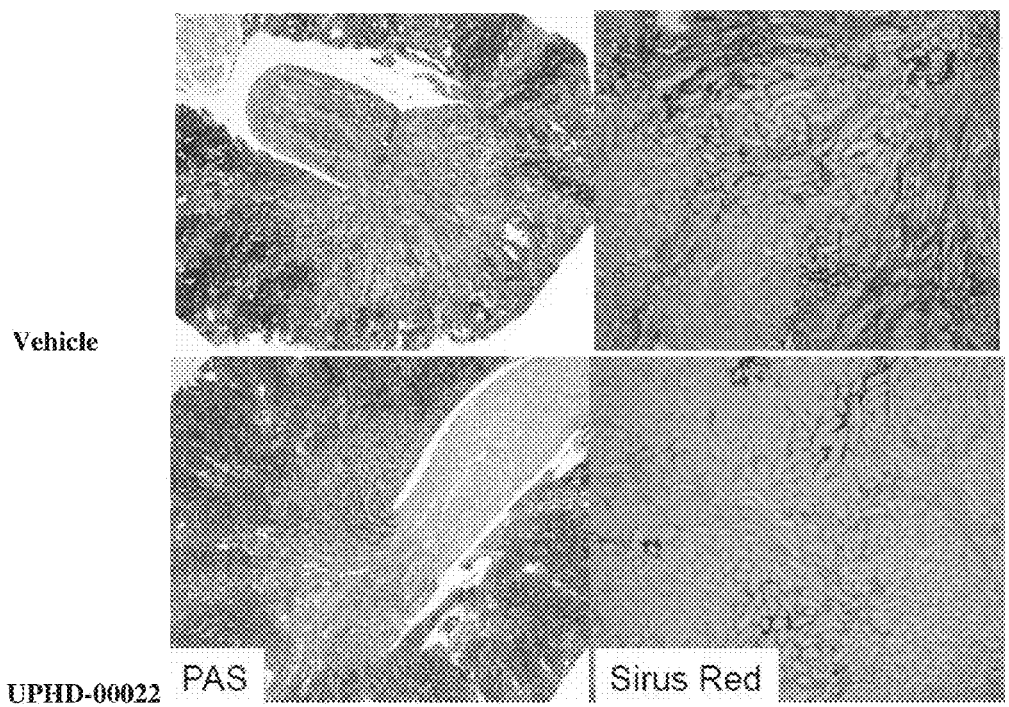

FIG. 42. Photomicrographs showing the results of an AKI model using folic acid-induced injury.

FIG. 43. Graph showing the results of an AKI model using gentamycin-induced injury (A) and table providing day results (B).

Figure 44:
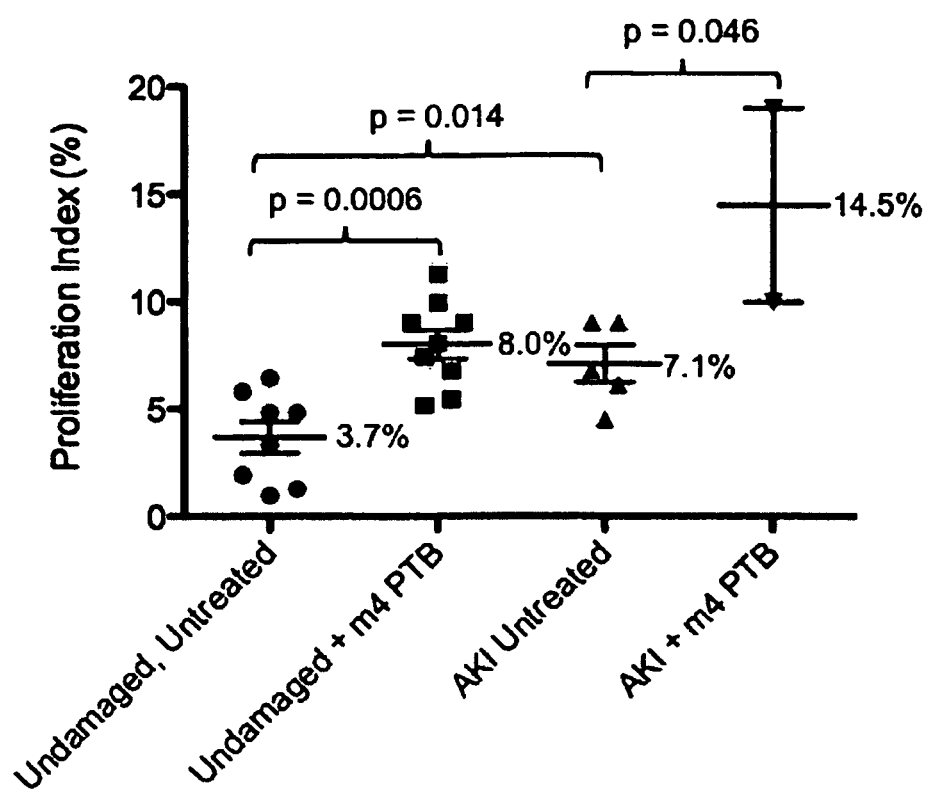

FIG. 44. Graph showing proliferation of renal cells examined post AKI for m4PTB in zebrafish embryos.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. "Comprising" and like terms are open-ended. The terms "a" and "an" refer to one or more.

As used herein, the term "patient" refers to members of the animal kingdom including but not limited to human beings and implies no relationship between a doctor or veterinarian and a patient.

Provided herein are compounds useful for improving kidney function, inhibiting a histone deacylase in a cell, expand renal progenitor cells and/or stimulating kidney repair in cells in vitro, ex vivo or in vivo (in a patient). Compositions also are provided for delivery of the compounds to a patient. Also provided are methods for improving kidney function, inhibiting a histone deacylase in a cell, expand renal progenitor cells and/or stimulating kidney repair in cells in vitro, ex vivo or in vivo (in a patient) comprising contacting the cells with, or administering to a patient and amount of one or more of the compounds effective to improve kidney function in a patient, inhibit a histone deacylase in a cell, expand renal progenitor cells and/or stimulate kidney repair in cells. Therefore provided are in vitro (including ex vivo) or in vivo (in a patient) methods. Efficacy of the compounds is demonstrated below.

Figure 1:
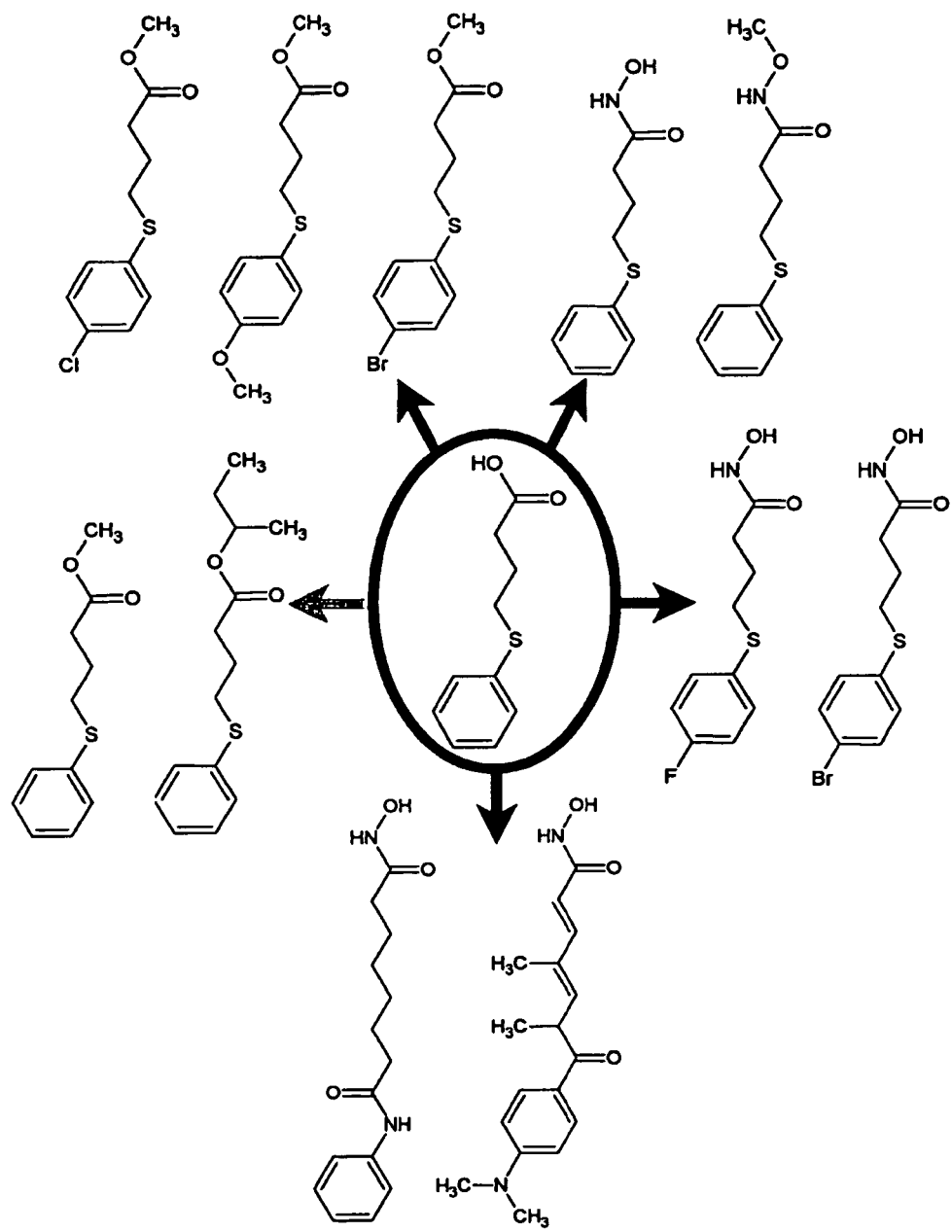
FIG. 1. HDACi Analogs. Lead compound, PTBA is shown in the center. Potential HDACi analogue families include: left arrow, esterified compounds; upper left arrow, esterified compounds with bulk added to the phenol ring for increased Log P; upper right arrow, hydroxamic compounds with bi-dentate zinc chelator; right arrow, hydroxamic compounds with bulk added to the phenol ring for increased Log P; downward arrow, other proven HDACi, such as SAHA and TSA.

The lead compound, PTBA, is unique in that it has relatively low toxicity when compared with several other established HDACi in zebrafish toxicity assays (see below), and a unique thioester moiety in the position of the connecting unit, a site that is typically occupied by an amide bond and has recently gained interest as a target for new drug design efforts. These findings have great potential because they identify for the first time a class of compounds that are non-toxic and accelerate renal recovery by enhancing the innate potential of renal tubular epithelium to regenerate following injury. By validating the use of this screening strategy, our preliminary studies also indicate that this strategy can be used to identify chemical modifications and synergistic interactions that will enhance the regenerative capacity of lead compounds both in the zebrafish embryo and subsequently in mouse models of AKI. Thus the examples presented below provide a unique opportunity to develop a panel of compounds that could have a real impact on the clinical outcome of a large number of patients presenting with AKI, particularly those with severe AKI in which potentially the majority of naturally occurring self-renewing epithelial cells have been depleted. In FIG. 1, exemplary HDACi analogues of PTBA are shown, with PTBA in the center. Potential HDACi analogue families to test include: esterified compounds; esterified compounds with bulk added to the phenol ring for increased Log P; hydroxamic compounds with bi-dentate zinc chelator; hydroxamic compounds with bulk added to the phenol ring for increased Log P; and, other proven HDACi, such as SAHA and TSA.

According to one non-limiting embodiment, a compound is provided having the formula:

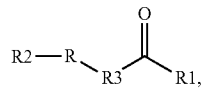

in which
R is S, S(O), S(O)$_2$ or NH,
R1 is —NH—R4 where R4 is OH, aminophenyl, hydroxyphenyl, C$_{1-4}$ alkyl hydroxyphenyl or phenyl hydroxyphenyl, or —O—R5 where R5 is H or C$_{1-4}$ alkyl,
R2 is phenyl; substituted phenyl;

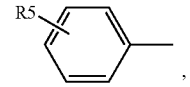

where R5 is halo; C$_{1-4}$ alkyl, methyl; methoxy, C$_{1-4}$ alkoxy; naphthyl; 1H-1,3-benzodiazol-2-yl; 1,3-benzothiazol-2-yl; pyrimidinyl, 1-methyl-1H-1,3benzodiazol-2-yl; pyridyl; methoxyphenyl; or methylthiophenyl, and R3 is from 0 to 5 methylene groups ((—CH$_2$—)$_{0-5}$) and 0 or 1 phenylene wherein at least one methylene or phenylene is present,
or a pharmaceutically acceptable salt thereof, other than 4-(phenylthio)butanoic acid (PTBA, also 4-(phenylsulfanyl) butanoic acid). In one example, R is S. R3 is an aliphatic alkylene, such as —CH$_2$—CH$_2$—CH$_2$—, —CH$_2$—CH$_2$—CH$_2$—CH$_2$— or —CH$_2$—CH$_2$—CH$_2$—CH$_2$—CH$_2$— that may include one phenylene group (i.e., 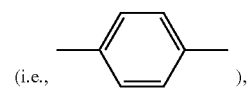 ), for example, R3 can be;

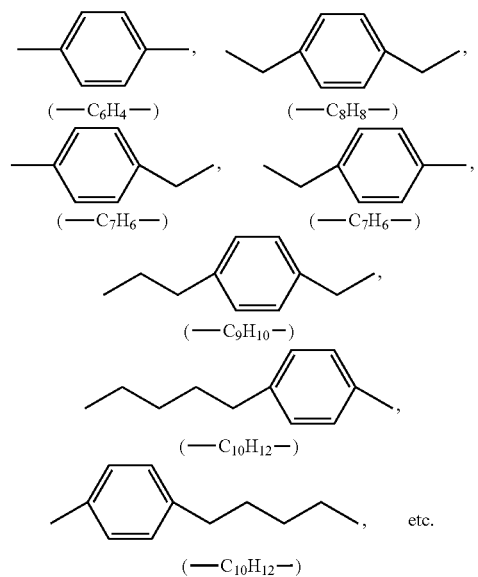

According to certain examples, R2 is phenyl, 4-fluorophenyl, 4-methoxyphenyl or 4-methylphenyl and/or R3 is —CH$_2$—CH$_2$—CH$_2$— or —CH$_2$—CH$_2$—CH$_2$—CH$_2$—CH$_2$—. In other examples, R1 is —NH—OH, —NH-2-aminophenyl, —NH-2-hydroxyphenyl or —O—CH$_3$. Specific examples of useful compounds include: UPHD-00029; UPHD-00028; UPHD-00034; UPHD-00051; UPHD-00067; UPHD-00025; UPHD-00030; UPHD-00022; UPHD-00047; UPHD-00048; UPHD-00049; UPHD-00053; UPHD-00077; or pharmaceutically acceptable salts thereof. Structures of non-limiting compounds described herein and useful in the methods described herein are provided in Table 1.

TABLE 1

| Compound structure | ID | MW | EF | LogP | Name |
|---|---|---|---|---|---|
| (phenyl-S-CH2CH2CH2-COOH) | UPHD-00020 | 196.27 | $C_{10}H_{12}O_2S$ | 2.5 | 4-(phenylthio)butanoic acid (PTBA) |
| (phenyl-S-CH2CH2CH2-C(O)NHOH) | UPHD-00023 (VNK-I-276) | 211.28 | $C_{10}H_{13}NO_2S$ | 1.69 | N-hydroxy-4(phenyl-sulfanyl)butanamide |
| (4-F-phenyl-S-CH2CH2CH2-C(O)NHOH) | UPHD-00029 (VNK-I-294) | 229.27 | $C_{10}H_{12}FNO_2S$ | 1.83 | 4-[(4-fluoro-phenyl)sulfanyl]-N-hydroxybutanamide |
| (4-Me-phenyl-S-CH2CH2CH2-C(O)NHOH) | UPHD-00028 (VNK-I-305) | 225.31 | $C_{11}H_{15}NO_2S$ | 2.2 | N-hydroxy-4-[(4-methyl-phenyl)sulfanyl]butanamide |
| (4-Cl-phenyl-S-CH2CH2CH2-C(O)NHOH) | UPHD-00027 (VNK-I-287) | 245.73 | $C_{10}H_{12}ClNO_2S$ | 2.3 | 4-[(4-chloro-phenyl)sulfanyl]-N-hydroxybutanamide |
| (4-MeO-phenyl-SO2-CH2CH2CH2-COOH) | UPHD-00097 | 258.2909 (Exact = 258.0562) | $C_{11}H_{14}O_5S$ | 0.81 | 4-[(4-methoxy-benzene)sulfonyl]butanoic acid |
| (phenyl-S-CH2CH2CH2CH2-C(O)NHOH) | UPHD-00035 | 225.3073 | $C_{11}H_{15}NO_2S$ | 2.14 | N-hydroxy-5-(phenyl-sulfanyl)pentanamide |
| (4-F-phenyl-S-CH2CH2CH2CH2-C(O)NHOH) | UPHD-00034 | 243.3 | $C_{11}H_{14}FNO_2S$ | 2.28 | 5-[(4-fluoro-phenyl)sulfanyl]-N-hydroxypentanamide |
| (phenyl-S-CH2CH2CH2CH2CH2-C(O)NHOH) | UPHD-00050 | 239.3339 | $C_{12}H_{17}NO_2S$ | 2.72 | N-hydroxy-6-(phenyl-sulfanyl)hexanamide |
| (4-F-phenyl-S-CH2CH2CH2CH2CH2-C(O)NHOH) | UPHD-00051 | 257.3243 | $C_{12}H_{16}FNO_2S$ | 3.07 | 6-[(4-fluoro-phenyl)sulfanyl]-N-hydroxyhexanamide |

TABLE 1-continued

| Compound structure | ID | MW | EF | LogP | Name |
|---|---|---|---|---|---|
| (3-fluorophenyl sulfanyl hexanohydroxamic acid structure) | UPHD-00119 | 257.3243 (Exact = 257.0886) | $C_{12}H_{16}FNO_2S$ | 2.72 | 6-[(3-fluoro-phenyl)sulfanyl]-N-hydroxyhexanamide |
| (2-fluorophenyl sulfanyl hexanohydroxamic acid structure) | UPHD-00118 | 257.3243 (Exact = 257.0886) | $C_{12}H_{16}FNO_2S$ | 2.72 | 6-[(2-fluoro-phenyl)sulfanyl]-N-hydroxyhexanamide |
| (4-chlorophenyl sulfanyl hexanohydroxamic acid structure) | UPHD-00143 | 273.7789 (Exact = 273.059) | $C_{12}H_{16}ClNO_2S$ | | 6-[(4-fluoro-phenyl)sulfanyl]-N-hydroxyhexanamide |
| (4-methoxyphenyl sulfanyl hexanohydroxamic acid structure) | UPHD-00130 | 269.3599 (Exact = 269.1086) | $C_{13}H_{19}NO_3S$ | 2.42 | N-hydroxy-6-[(4-methoxy-phenyl)sulfanyl]hexanamide |
| (3-methoxyphenyl sulfanyl hexanohydroxamic acid structure) | UPHD-00131 | 269.3599 (Exact = 269.1086) | $C_{13}H_{19}NO_3S$ | 2.42 | N-hydroxy-6-[(3-methoxy-phenyl)sulfanyl]hexanamide |
| (2-methoxyphenyl sulfanyl hexanohydroxamic acid structure) | UPHD-00132 | 269.3599 (Exact = 269.1086) | $C_{13}H_{19}NO_3S$ | 2.42 | N-hydroxy-6-[(2-methoxy-phenyl)sulfanyl]hexanamide |
| (phenyl sulfanyl heptanohydroxamic acid structure) | UPHD-00041 | 253.3605 | $C_{13}H_{19}NO_2S$ | 3.02 | N-hydroxy-7-(phenyl-sulfanyl)heptanamide |
| (4-fluorophenyl sulfanyl heptanohydroxamic acid structure) | UPHD-00042 | 271.3509 | $C_{13}H_{18}FNO_2S$ | 3.17 | 7-[(4-fluoro-phenyl)sulfanyl]-N-hydroxyheptanamide |
| (phenylsulfanylmethyl benzohydroxamic acid structure) | UPHD-00052 | 259.3235 | $C_{14}H_{13}NO_2S$ | 3.07 | N-hydroxy-4-[(phenyl-sulfanyl)methyl]benzamide |
| (4-fluorophenyl sulfanyl ethyl benzohydroxamic acid structure) | UPHD-00067 | 291.3406 (Exact = 291.0729) | $C_{15}H_{14}FNO_2S$ | 3.5 | 4-{2[(4-fluoro-phenyl)sulfanyl]ethyl}-N-hydroxybenzamide |

TABLE 1-continued

| Compound structure | ID | MW | EF | LogP | Name |
|---|---|---|---|---|---|
| 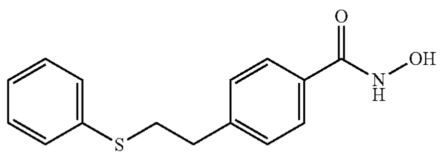 [SMILES: O=C(NO)c1ccc(CCSc2ccccc2)cc1] | UPHD-00061 | 273.3501 (Exact = 273.0823) | $C_{15}H_{15}NO_2S$ | 3.36 | N-hydroxy-4-[2-(phenyl-sulfanyl)ethyl]benzamide |
| 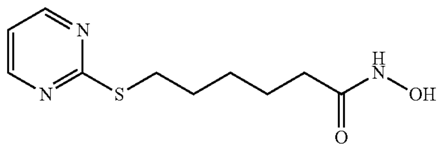 [SMILES: O=C(CCCCCSc1ncccn1)NO] | UPHD-00074 | 241.31 (Exact = 241.0885) | $C_{10}H_{15}N_3O_2S$ | 1.34 | N-hydroxy-6-(pyrmidin-2-ylsulfanyl)hexanamide |
| 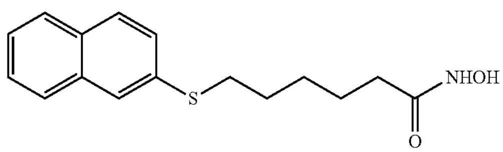 | UPHD-00059 | 289.3926 (Exact = 289.1136) | $C_{16}H_{19}NO_2S$ | 3.57 | N-hydroxy-6-(naphthalen-2-ylsulfanyl)hexanamide |
| 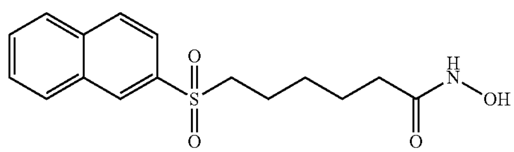 [SMILES: O=C(CCCCCS(=O)(=O)c1ccc2ccccc2c1)NO] | UPHD-00069 | 321.3914 (Exact = 321.1035) | $C_{16}H_{19}NO_4S$ | 2.04 | N-hydroxy-6-(naphthalene-2-sulfonyl)hexanamide |
| 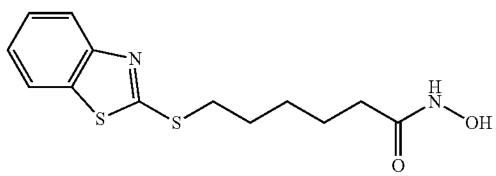 [SMILES: O=C(CCCCCSc1nc2ccccc2s1)NO] | UPHD-00070 | 296.4083 (Exact = 296.0653) | $C_{13}H_{16}N_2O_2S_2$ | 3.4 | 6-(1,3-benzothiazol-2-ylsulfanyl)-N-hydroxyhexanamide |
| 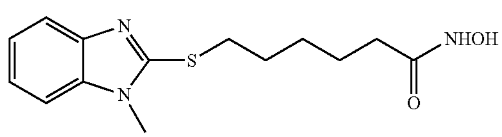 | UPHD-00085 | 293.3846 (Exact = 293.1198) | $C_{14}H_{19}N_3O_2S$ | 2.77 | N-hydroxy-6-[(1-methyl-1H-1,3benzodiazol-2-yl)sulfanyl]hexanamide |
| 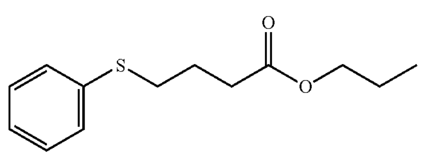 [SMILES: CCCOC(=O)CCCSc1ccccc1] | UPHD-00024 | 238 | $C_{13}H_{18}O_2S$ | 3.53 | propyl 4-(phenylsulfanyl)butanoate |
| 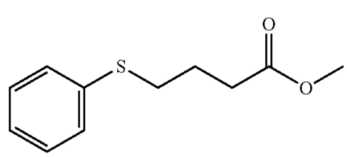 | UPHD-00025 | 210.29 | $C_{11}H_{14}O_2S$ | 2.65 | methyl 4-(phenylsulfanyl)butanoate (m4PTB) |
| 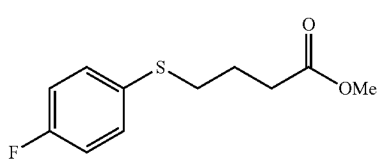 [SMILES: COC(=O)CCCSc1ccc(F)cc1] | UPHD-00030 (VNK-I-291) | 228.28 | $C_{11}H_{13}FO_2S$ | 2.79 | methyl 4-[(4-fluoro-phenyl)sulfanyl]butanoate |
| 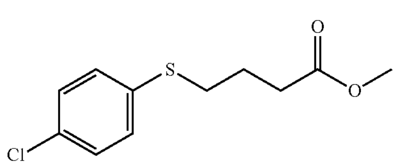 | UPHD-00021 (VNK-I-284) | 244.74 | $C_{11}H_{13}ClO_2S$ | 3.25 | methyl 4-[(4-chloro-phenyl)sulfanyl]butanoate |

TABLE 1-continued

| Compound structure | ID | MW | EF | LogP | Name |
|---|---|---|---|---|---|
| 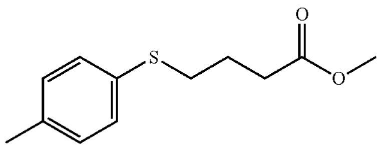 | UPHD-00026 (VNK-I-285) | 224.32 | $C_{12}H_{16}O_2S$ | 3.16 | methyl 4-[(4-methyl-phenyl)sulfanyl]butanoate |
| 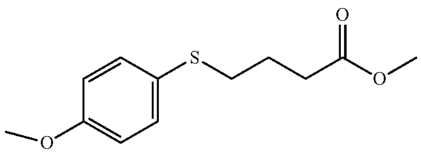 | UPHD-00022 (VNK-I-286) | 240.32 | $C_{12}H_{16}O_3S$ | 2.49 | methyl 4-[(4-methoxy-phenyl)sulfanyl]butanoate |
| 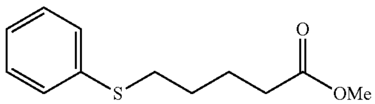 [SMILES: COC(=O)CCCCSc1ccccc1] | UPHD-00033 | 224.3192 | $C_{12}H_{16}O_2S$ | 3.09 | methyl 5-(phenylsulfanyl)pentanoate |
| 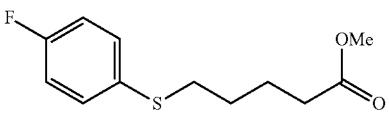 [SMILES: COC(=O)CCCCSc1ccc(F)cc1] | UPHD-00032 | 242.3097 | $C_{12}H_{15}FO_2S$ | 3.23 | methyl 5-[(4-fluoro-phenyl)sulfanyl]pentanoate |
| 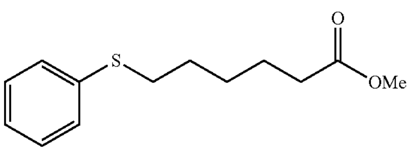 [SMILES: COC(=O)CCCCCSc1ccccc1] | UPHD-00047 | 238.3458 | $C_{13}H_{18}O_2S$ | 3.68 | methyl 6-(phenyl-sulfanyl)hexanoate |
| 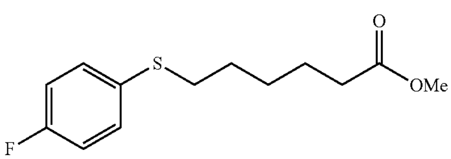 [SMILES: COC(=O)CCCCCSc1ccc(F)cc1] | UPHD-00048 | 256.3363 | $C_{13}H_{17}FO_2S$ | 3.54 | methyl 6-[(4-fluoro-phenyl)sulfanyl]hexanoate |
| 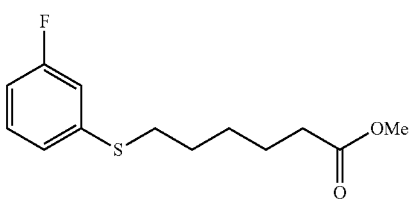 [SMILES: COC(=O)CCCCCSc1cccc(F)c1] | UPHD-00088 | 256.3363 (Exact = 256.0933) | $C_{13}H_{17}FO_2S$ | 3.68 | methyl 6-[(3-fluoro-phenyl)sulfanyl]hexanoate |
| 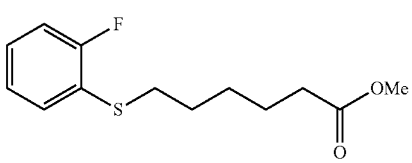 [SMILES: COC(=O)CCCCCSc1ccccc1F] | UPHD-00089 | 256.3363 (Exact = 256.0933) | $C_{13}H_{17}FO_2S$ | 3.68 | methyl 6-[(2-fluoro-phenyl)sulfanyl]hexanoate |
| 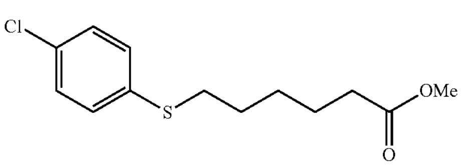 [SMILES: COC(=O)CCCCCSc1ccc(Cl)cc1] | UPHD-00111 | 272.7909 (Exact = 272.0638) | $C_{13}H_{17}ClO_2S$ | 4.14 | methyl 6-[(4-chloro-phenyl)sulfanyl]hexanoate |
| 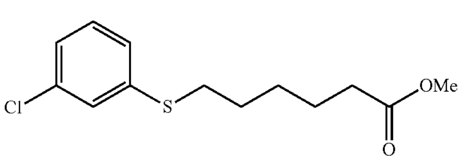 [SMILES: COC(=O)CCCCCSc1cccc(Cl)c1] | UPHD-00113 | 272.7909 (Exact = 272.0638) | $C_{13}H_{17}ClO_2S$ | 4.14 | methyl 6-[(3-chloro-phenyl)sulfanyl]hexanoate |

TABLE 1-continued

| Compound structure | ID | MW | EF | LogP | Name |
|---|---|---|---|---|---|
| 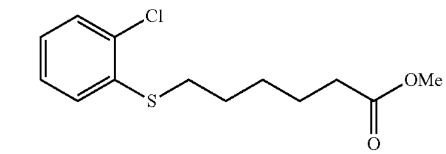 [SMILES: COC(=O)CCCCCSc1ccccc1Cl] | UPHD-00112 | 272.7909 (Exact = 272.0638) | $C_{13}H_{17}ClO_2S$ | 4.14 | methyl 6-[(2-chloro-phenyl)sulfanyl]hexanoate |
| 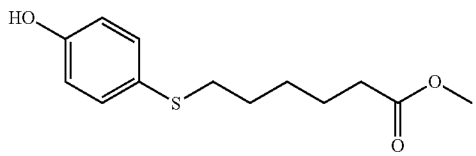 [SMILES: COC(=O)CCCCCSc1ccc(O)cc1] | UPHD-00144 | 254.3452 | $C_{13}H_{18}O_3S$ | | methyl 6-[(4-hydroxy-phenyl)sulfanyl]hexanoate |
| 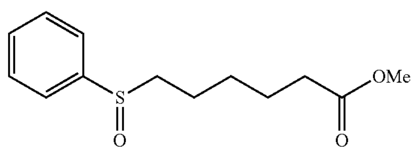 [SMILES: COC(=O)CCCCCS(=O)c1ccccc1] | UPHD-00106 | 254.3452 (Exact = 254.0977) | $C_{13}H_{18}O_3S$ | 1.9 | methyl 6-(phenylsulfinyl)hexanoate |
| 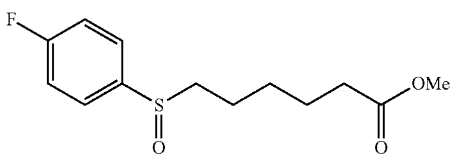 [SMILES: COC(=O)CCCCCS(=O)c1ccc(F)cc1] | UPHD-00107 | 272.3357 (Exact = 272.0882) | $C_{13}H_{17}FO_3S$ | 2.04 | methyl 6-[(4-fluoro-phenyl)sulfinyl]hexanoate |
| 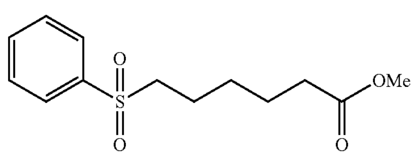 [SMILES: COC(=O)CCCCCS(=O)(=O)c1ccccc1] | UPHD-00091 | 270.3446 (Exact = 270.0926) | $C_{13}H_{18}O_4S$ | 2 | methyl 6-(benzenesulfonyl)hexanoate |
| 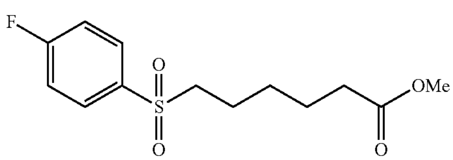 [SMILES: COC(=O)CCCCCS(=O)(=O)c1ccc(F)cc1] | UPHD-00092 | 288.3351 (Exact = 288.0832) | $C_{13}H_{17}FO_4S$ | 2.15 | methyl 6-[(4-fluoro-benzene)sulfonyl]hexanoate |
| 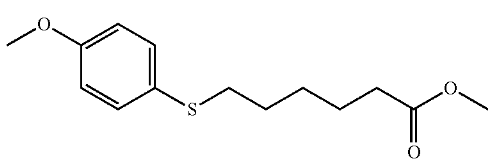 | UPHD-00090 | 268.3718 (Exact = 268.1133) | $C_{14}H_{20}O_3S$ | 3.38 | methyl 6-[(4-methoxy-phenyl)sulfanyl]hexanoate |
| 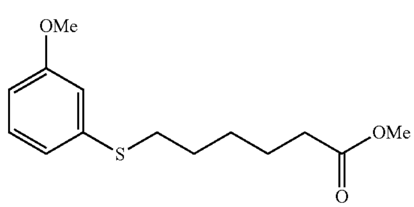 [SMILES: COC(=O)CCCCCSc1cccc(OC)c1] | UPHD-00100 | 268.3718 (Exact = 268.1133) | $C_{14}H_{20}O_3S$ | 3.38 | methyl 6-[(3-methoxy-phenyl)sulfanyl]hexanoate |
| 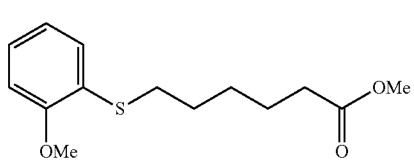 [SMILES: COC(=O)CCCCCSc1ccccc1OC] | UPHD-00101 | 268.3718 (Exact = 268.1133) | $C_{14}H_{20}O_3S$ | 3.38 | methyl 6-[(2-methoxy-phenyl)sulfanyl]hexanoate |

TABLE 1-continued

| Compound structure | ID | MW | EF | LogP | Name |
|---|---|---|---|---|---|
| 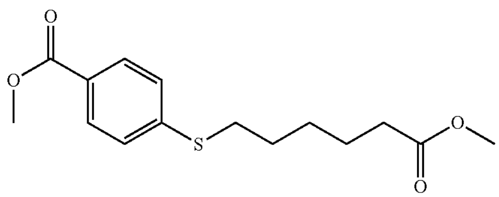 [SMILES: COC(=O)CCCCCSc1ccc(C(=O)OC)cc1] | UPHD-00135 | 296.3819 (Exact = 296.1082) | $C_{15}H_{20}O_4S$ | 3.54 | methyl 4-[(6-methoxy-6-oxohexyl)sulfanyl]benzoate |
| 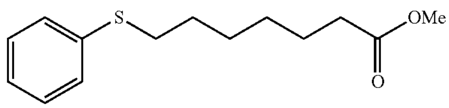 [SMILES: COC(=O)CCCCCCSc1ccccc1] | UPHD-00040 | 252.3724 | $C_{14}H_{20}O_2S$ | 3.98 | methyl 7-(phenylsulfanyl)heptanoate |
| 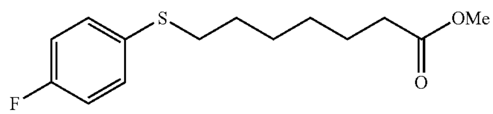 [SMILES: COC(=O)CCCCCCSc1ccc(F)cc1] | UPHD-00039 | 270.3629 | $C_{14}H_{19}FO_2S$ | 4.12 | methyl 7-[(4-fluorphenyl)sulfanyl]heptanoate |
| 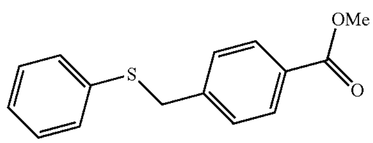 [SMILES: COC(=O)c1ccc(CSc2ccccc2)cc1] | UPHD-00045 | 258.3355 | $C_{15}H_{14}O_2S$ | 4.23 | methyl 4[(phenylsulfanyl)methyl]benzoate |
| 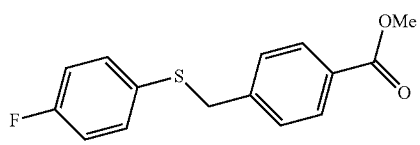 [SMILES: COC(=O)c1ccc(CSc2ccc(F)cc2)cc1] | UPHD-00046 | 276.3259 | $C_{15}H_{13}FO_2S$ | 4.37 | methyl 4-{[(4-fluorophenyl)sulfanyl]methyl}benzoate |
| 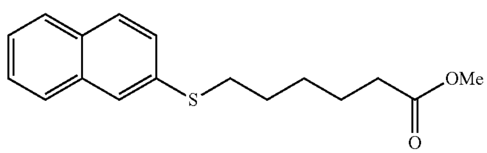 [SMILES: COC(=O)CCCCCSc1ccc2ccccc2c1] | UPHD-00057 | 288.4045 (Exact = 288.1184) | $C_{17}H_{20}O_2S$ | 4.53 | methyl 6-(naphthalen-2-ylsulfanyl)hexanoate |
| 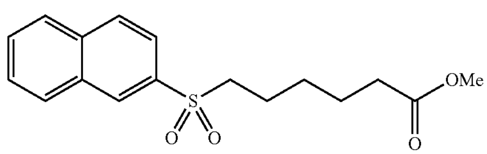 [SMILES: COC(=O)CCCCCS(=O)(=O)c1ccc2ccccc2c1] | UPHD-00063 | 320.4033 (Exact = 320.1082) | $C_{17}H_{20}O_4S$ | 2.99 | methyl 6-(naphthalen-2-ylsulfonyl)hexanoate |
| 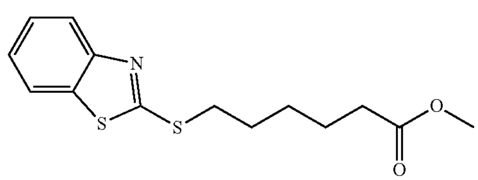 [SMILES: COC(=O)CCCCCSc1nc2ccccc2s1] | UPHD-00062 | 295.4203 (Exact = 295.0701) | $C_{14}H_{17}NO_2S_2$ | 4.36 | methyl 6-(1,3-benzothiazol-2-ylsulfanyl)hexanoate) |
| 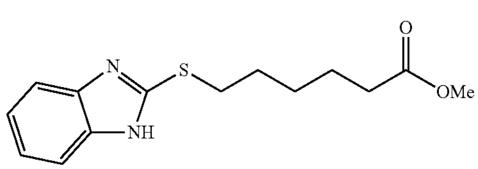 [SMILES: COC(=O)CCCCCSc1nc2ccccc2[nH]1] | UPHD-00076 | 278.3699 (Exact = 278.1089) | $C_{14}H_{18}N_2O_2S$ | 3.51 | methyl 6-(1H-1,3benzodiazol-2-ylsulfanyl)hexanoate |
| 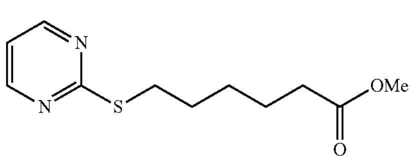 [SMILES: COC(=O)CCCCCSc1ncccn1] | UPHD-00058 | 240.3219 (Exact = 240.0932) | $C_{11}H_{16}N_2O_2S$ | 2.29 | methyl 6-(pyrimidin-2-ylsulfanyl)hexanoate |

TABLE 1-continued

| Compound structure | ID | MW | EF | LogP | Name |
|---|---|---|---|---|---|
| 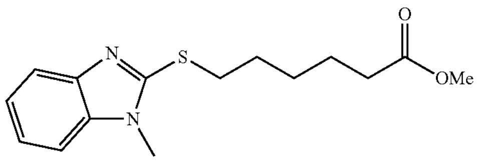 [SMILES: COC(=O)CCCCCSc1nc2ccccc2n1C] | UPHD-00075 | 292.3965 (Exact = 292.1245) | $C_{15}H_{20}N_2O_2S$ | 3.73 | methyl 6-[(1-methyl-1H-1,3-benzodiazol-2-yl)sulfanyl]hexanoate |
| 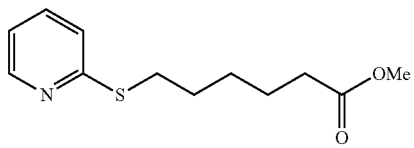 [SMILES: COC(=O)CCCCCSc1ccccn1] | UPHD-00065 | 239.3339 (Exact = 239.098) | $C_{12}H_{17}NO_2S$ | 2.91 | methyl 6-(pyridin-2-ylsulfanyl)hexanoate |
| 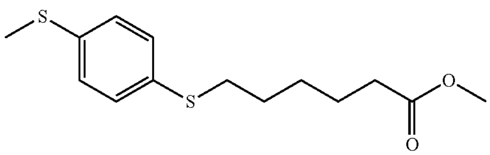 | UPHD-00142 | 284.4374 (Exact = 284.0905) | $C_{14}H_{20}O_2S_2$ | | methyl 6-[(4-(methyl-sulfanyl)phenyl)sulfanyl]hexanoate |
| 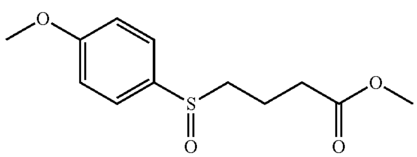 | UPHD-00094 | 256.318 (Exact = 256.0769) | $C_{12}H_{16}O_4S$ | 0.85 | methyl 4-[4-methyoxy-benzene)sulfinyl]butanoate |
| 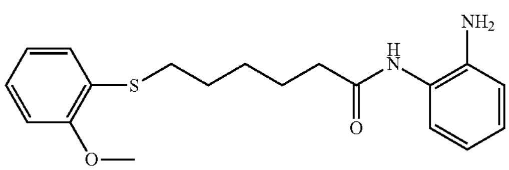 [SMILES: COc1ccccc1SCCCCCC(=O)Nc1ccccc1N] | UPHD-00129 | 344.1558 (Exact = 344.4711) | $C_{19}H_{24}N_2O_2S$ | 3.84 | N-(2-aminophenyl)-6-[(2-methoxy-phenyl)sulfanyl]hexanamide |
| 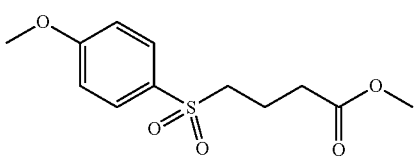 | UPHD-00093 | 272.3174 (Exact = 272.0718) | $C_{12}H_{16}O_5S$ | 0.96 | methyl 4-[(4-methoxy-benzene)sulfonyl]butanoate |
| 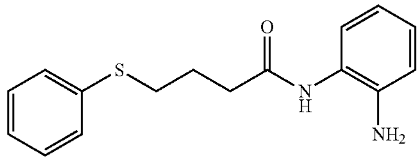 [SMILES: Nc1ccccc1NC(=O)CCCSc1ccccc1] | UPHD-00036 | 286.3919 | $C_{16}H_{18}N_2OS$ | 3.11 | N-(2-aminophenyl)-4-(phenylsulfanyl)butanamide |
| 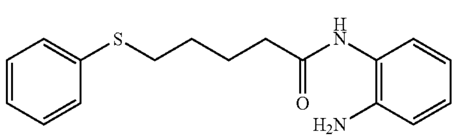 [SMILES: Nc1ccccc1NC(=O)CCCCSc1ccccc1] | UPHD-00038 | 300.4185 | $C_{17}H_{20}N_2OS$ | 3.55 | N-(2-aminophenyl)-5-(phenylsulfanyl)pentanamide |
| 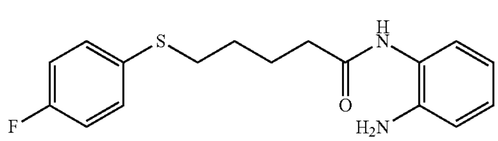 [SMILES: Nc1ccccc1NC(=O)CCCCSc1ccc(F)cc1] | UPHD-00037 | 318.409 | $C_{17}H_{19}FN_2OS$ | 3.69 | N-(2-aminophenyl)-5-[(4-fluoro-phenyl)sulfanyl]pentanamide |

TABLE 1-continued

| Compound structure | ID | MW | EF | LogP | Name |
|---|---|---|---|---|---|
| 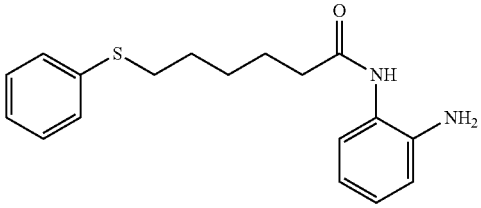 [SMILES: Nc1ccccc1NC(=O)CCCCCSc1ccccc1] | UPHD-00049 | 314.4451 (Exact = 314.1453) | $C_{18}H_{22}N_2OS$ | 4 | N-(2-aminophenyl)-6-(phenylsulfanyl)hexanamide |
| 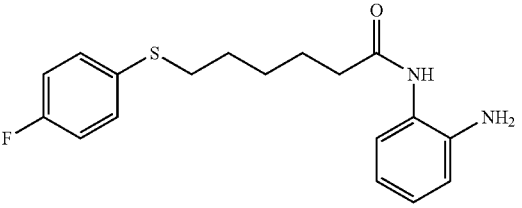 [SMILES: Nc1ccccc1NC(=O)CCCCCSc1ccc(F)cc1] | UPHD-00053 | 332.4355 (Exact = 332.1359) | $C_{18}H_{21}FN_2OS$ | 4.14 | N-(2-aminophenyl)-6-[(4-fluoro-phenyl)sulfanyl]hexanamide |
| 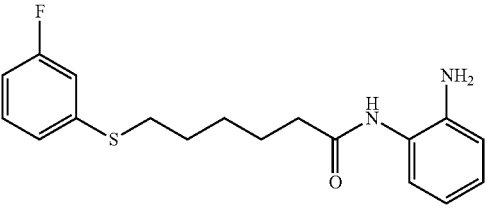 [SMILES: Nc1ccccc1NC(=O)CCCCCSc1cccc(F)c1] | UPHD-00136 | 332.4355 (Exact = 332.1359) | $C_{18}H_{21}FN_2OS$ | 4.14 | N-(2-aminophenyl)-6-[(3-fluoro-phenyl)sulfanyl]hexanamide |
| 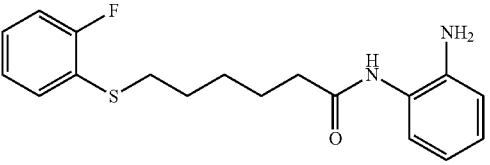 [SMILES: Nc1ccccc1NC(=O)CCCCCSc1ccccc1F] | UPHD-00122 | 332.4355 (Exact = 332.1359) | $C_{18}H_{21}FN_2OS$ | 4.14 | N-(2-aminophenyl)-6-[(2-fluoro-phenyl)sulfanyl]hexanamide |
| 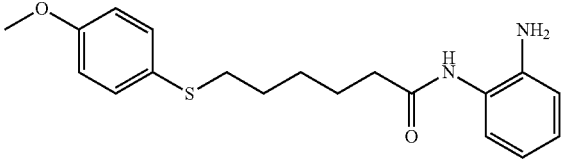 [SMILES: COc1ccc(SCCCCCC(=O)Nc2ccccc2N)cc1] | UPHD-00125 | 344.4711 (Exact = 344.1558) | $C_{19}H_{24}N_2O_2S$ | 3.84 | N-(2-aminophenyl)-6-[(4-methoxy-phenyl)sulfanyl]hexanamide |
| 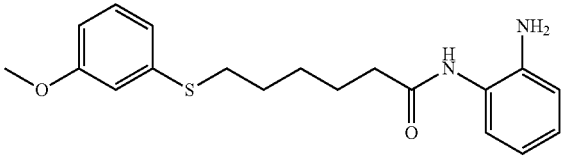 [SMILES: COc1cccc(SCCCCCC(=O)Nc2ccccc2N)c1] | UPHD-00126 | 344.4711 (Exact = 344.1558) | $C_{19}H_{24}N_2O_2S$ | 3.84 | N-(2-aminophenyl)-6-[(3-methoxy-phenyl)sulfanyl]hexanamide |
| 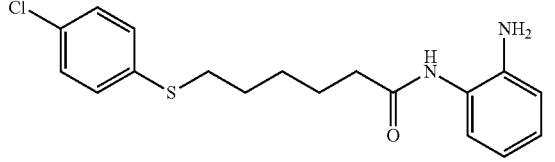 | UPHD-00128 | 348.8901 (Exact = 348.1063) | $C_{18}H_{21}ClN_2OS$ | 4.6 | N-(2-aminophenyl)-6-[(4-chloro-phenyl)sulfanyl]hexanamide |
| 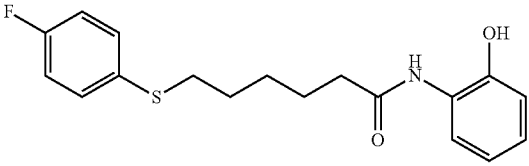 [SMILES: O=C(CCCCCSc1ccc(F)cc1)Nc1ccccc1O] | UPHD-00077 | 333.4203 (Exact = 333.1199) | $C_{18}H_{20}FNO_2S$ | 4.66 | 6-[(4-fluoro-phenyl)sulfanyl]-N-(2-hydroxyphenyl)hexanamide |

TABLE 1-continued

| Compound structure | ID | MW | EF | LogP | Name |
|---|---|---|---|---|---|
| 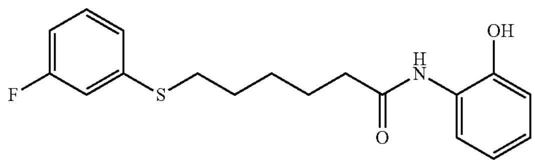 [SMILES: O=C(CCCCCSc1cccc(F)c1)Nc1ccccc1O] | UPHD-00115 | 333.4203 (Exact = 333.1199) | $C_{18}H_{20}FNO_2S$ | 4.66 | 6-[(3-fluoro-phenyl)sulfanyl]-N-(2-hydroxyphenyl)hexanamide |
| 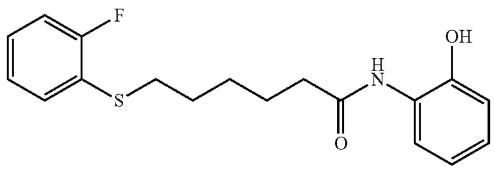 [SMILES: O=C(CCCCCSc1ccccc1F)Nc1ccccc1O] | UPHD-00114 | 333.4203 (Exact = 333.1199) | $C_{18}H_{20}FNO_2S$ | 4.66 | 6-[(2-fluoro-phenyl)sulfanyl]-N-(2-hydroxyphenyl)hexanamide |
| 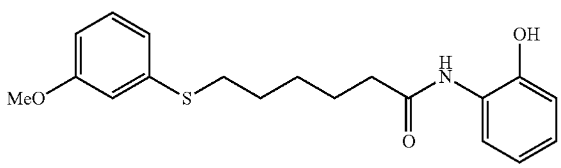 [SMILES: COc1cccc(SCCCCCC(=O)Nc2ccccc2O)c1] | UPHD-00123 | 345.4558 (Exact = 345.1399) | $C_{19}H_{23}NO_3S$ | 4.36 | N-(2-hydroxyphenyl)-6-[(3-methoxy-phenyl)sulfanyl]hexanamide |
| 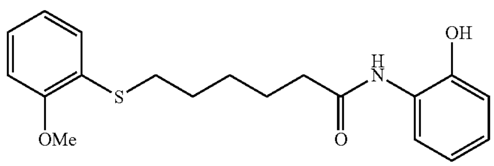 [SMILES: COc1ccccc1SCCCCCC(=O)Nc1ccccc1O] | UPHD-00121 | 345.4558 (Exact = 345.1399) | $C_{19}H_{23}NO_3S$ | 4.36 | N-(2-hydroxyphenyl)-6-[(2-methoxy-phenyl)sulfanyl]hexanamide |
| 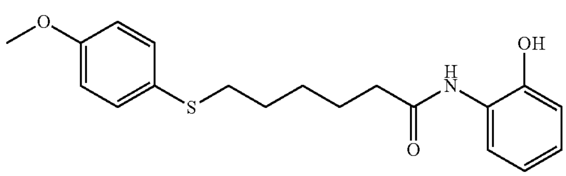 [SMILES: COc1ccc(SCCCCCC(=O)Nc2ccccc2O)cc1] | UPHD-00124 | 345.4558 (Exact = 345.1399) | $C_{19}H_{23}NO_3S$ | 4.36 | N-(2-hydroxyphenyl)-6-[(4-methoxy-phenyl)sulfanyl]hexanamide |
| 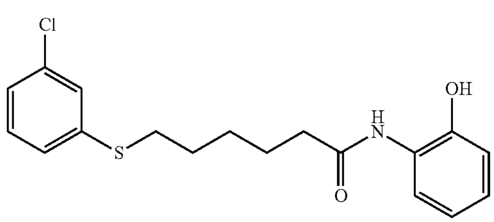 [SMILES: O=C(CCCCCSc1cccc(Cl)c1)Nc1ccccc1O] | UPHD-00138 | 349.8749 (Exact = 349.0903) | $C_{18}H_{20}ClNO_2S$ | 5.13 | 6-[(3-chlorophenyl)sulfanyl]-N-(2-hydroxy-phenyl)hexanamide |
| 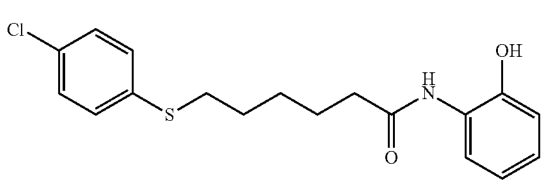 [SMILES: O=C(CCCCCSc1ccc(Cl)cc1)Nc1ccccc1O] | UPHD-00127 | 349.8749 (Exact = 349.0903) | $C_{18}H_{20}ClNO_2S$ | 5.13 | 6-[(4-chloro-phenyl)sulfanyl]-N-(2-hydroxyphenyl)hexanamide |
| 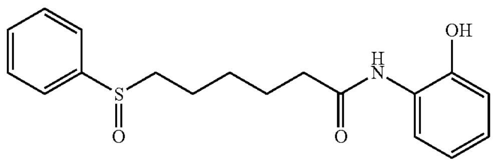 [SMILES: O=C(CCCCCS(=O)c1ccccc1)Nc1ccccc1O] | UPHD-00140 | 331.4292 (Exact = 331.1242) | $C_{18}H_{21}NO_3S$ | 2.88 | 6-(benzenesulfinyl)-N-(2-hydroxyphenyl)hexanamide |

TABLE 1-continued

| Compound structure | ID | MW | EF | LogP | Name |
|---|---|---|---|---|---|
| 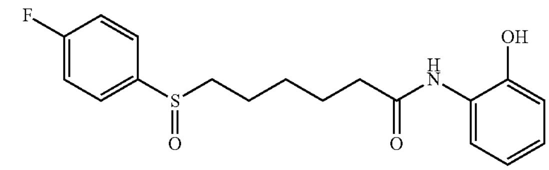 [SMILES: O=C(CCCCCS(=O)c1ccc(F)cc1)Nc1ccccc1O] | UPHD-00141 | 349.4197 (Exact = 349.1148) | $C_{18}H_{20}FNO_3S$ | | 6-(4-fluoro-benzenesulfinyl)-N-(2-hydroxyphenyl)hexanamide |
| 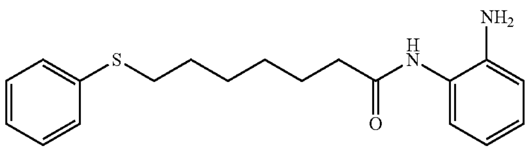 [SMILES: Nc1ccccc1NC(=O)CCCCCCSc1ccccc1] | UPHD-00044 | 328.4717 | $C_{19}H_{24}N_2OS$ | 4.44 | N-(2-aminophenyl)-7-(phenylsulfanyl)heptanamide |
| 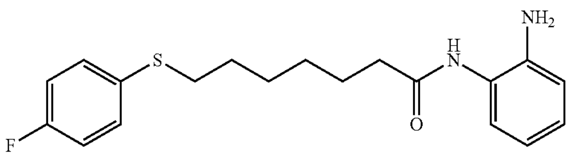 [SMILES: Nc1ccccc1NC(=O)CCCCCCSc1ccc(F)cc1] | UPHD-00043 | 346.4621 | $C_{19}H_{23}FN_2OS$ | 4.58 | N-(2-aminophenyl)-7-[(4-fluoro-phenyl)sulfanyl]heptanamide |
| 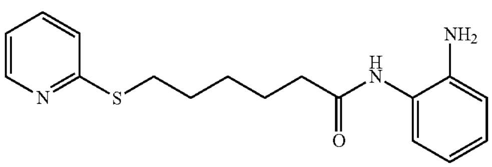 [SMILES: Nc1ccccc1NC(=O)CCCCCSc1ccccn1] | UPHD-00073 | 315.4331 (Exact = 315.1405) | $C_{17}H_{21}N_3OS$ | 3.37 | N-(2-aminophenyl)-6-(pyridin-2-ylsulfanyl)hexanamide |
| 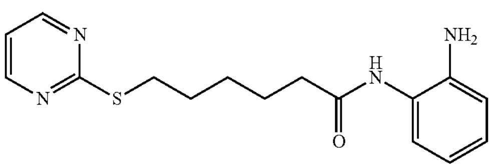 [SMILES: Nc1ccccc1NC(=O)CCCCCSc1ncccn1] | UPHD-00072 | 316.4212 (Exact = 316.1358) | $C_{16}H_{20}N_4OS$ | 2.75 | N-(2-aminophenyl)-6-(pyrimidin-2-ylsulfanyl)hexanamide |
| 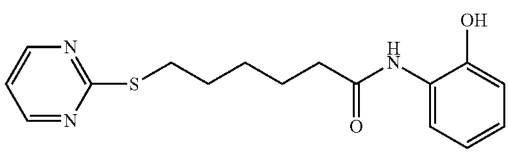 [SMILES: O=C(CCCCCSc1ncccn1)Nc1ccccc1O] | UPHD-00086 | 317.406 (Exact = 317.1198) | $C_{16}H_{19}N_3O_2S$ | 3.28 | N-(2-hydroxyphenyl)-6-(pyrimidin-2-ylsulfanyl)hexanamide |
| 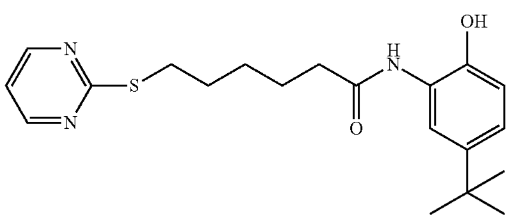 [SMILES: CC(C)(C)c1ccc(O)c(NC(=O)CCCCCSc2ncccn2)c1] | UPHD-00087 | 373.5123 (Exact = 373.1824) | $C_{20}H_{27}N_3O_2S$ | 4.82 | N-(5-tert-butyl-2-hydroxyphenyl)-6-(pyrimidin-2-ylsulfanyl)hexanamide |
| 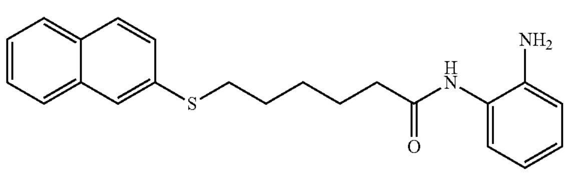 [SMILES: Nc1ccccc1NC(=O)CCCCCSc1ccc2ccccc2c1] | UPHD-00060 | 364.5038 (Exact = 364.1609) | $C_{22}H_{24}N_2OS$ | 4.99 | N-(2-aminophenyl)-6-(naphthalen-2-ylsulfanyl)hexanamide |
| 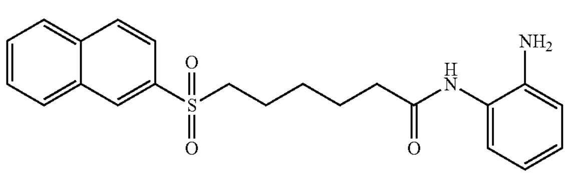 [SMILES: Nc1ccccc1NC(=O)CCCCCS(=O)(=O)c1ccc2ccccc2c1] | UPHD-00066 | 396.5026 (Exact = 396.1508) | $C_{22}H_{24}N_2O_3S$ | 3.45 | N-(2-aminophenyl)-6-(naphthalene-2-sulfonyl)hexanamide |

TABLE 1-continued

| Compound structure | ID | MW | EF | LogP | Name |
|---|---|---|---|---|---|
| 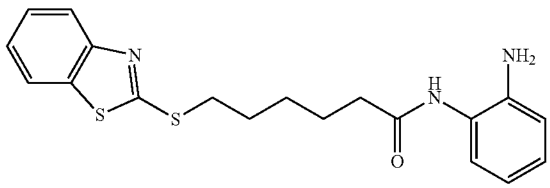 [SMILES: Nc1ccccc1NC(=O)CCCCCSc1nc2ccccc2s1] | UPHD-00071 | 371.5195 (Exact = 371.1126) | $C_{19}H_{21}N_3OS_2$ | 4.82 | N-(2-aminophenyl)-6-(1,3-benzothiazol-2-ylsulfanyl)hexanamide |
| 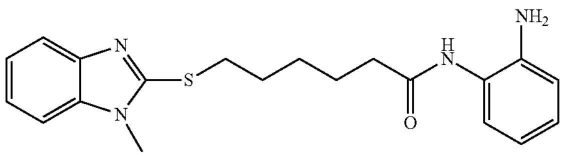 [SMILES: Cn1c(SCCCCCC(=O)Nc2ccccc2N)nc2ccccc21] | UPHD-00081 | 368.4958 (Exact = 368.1671) | $C_{20}H_{24}N_4OS$ | 4.19 | N-(2-aminophenyl)-6-[(1-methyl-1H-1,3-benzodiazol-2-yl)sulfanyl]hexanamide |
| 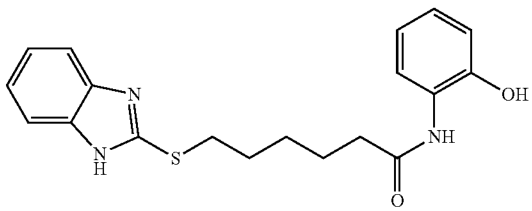 [SMILES: O=C(CCCCCSc1nc2ccccc2[nH]1)Nc1ccccc1O] | UPHD-00095 | 355.4539 (Exact = 355.1354) | $C_{19}H_{21}N_3O_2S$ | 4.49 | 6-(1H-1,3-benzodiazol-2-ylsulfanyl)-N-(2-hydroxyphenyl)hexanamide |
| 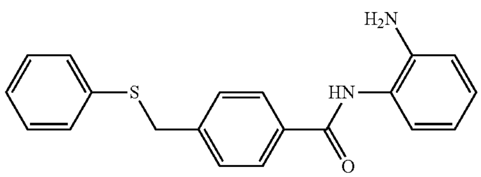 [SMILES: Nc1ccccc1NC(=O)c1ccc(CSc2ccccc2)cc1] | UPHD-00054 | 334.4347 (Exact = 334.114) | $C_{20}H_{18}N_2OS$ | 4.49 | N-(2-aminophenyl)-4-[(phenylsulfanyl)methyl]benzamide |
| 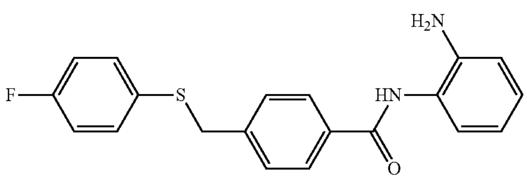 [SMILES: Nc1ccccc1NC(=O)c1ccc(CSc2ccc(F)cc2)cc1] | UPHD-00055 | 352.4252 (Exact = 352.1046) | $C_{20}H_{17}FN_2OS$ | 4.63 | N-(2-aminophenyl)-4-({[(4-fluorophenyl)sulfanyl]methyl})benzamide |
| 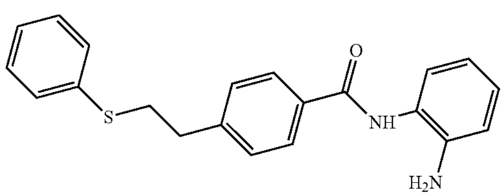 [SMILES: Nc1ccccc1NC(=O)c1ccc(CCSc2ccccc2)cc1] | UPHD-00064 | 348.4612 (Exact = 348.1296) | $C_{21}H_{20}N_2OS$ | 4.77 | N-(2-aminophenyl)-4-[2-(phenylsulfanyl)ethyl]benzamide |
| 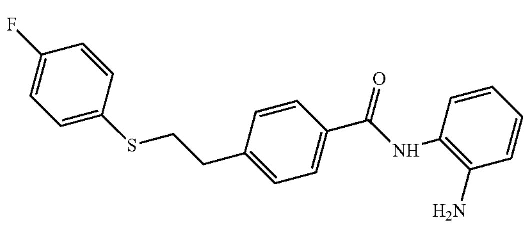 [SMILES: Nc1ccccc1NC(=O)c1ccc(CCSc2ccc(F)cc2)cc1] | UPHD-00068 | 366.4518 (Exact = 366.1202) | $C_{21}H_{19}FN_2OS$ | 4.92 | N-(2-aminophenyl)-4-{2-[(4-fluorophenyl)sulfanyl]ethyl}benzamide |
| 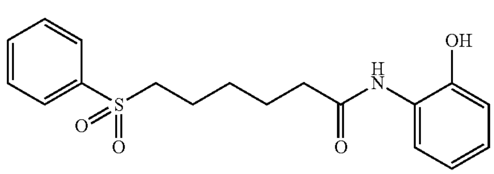 [SMILES: O=C(CCCCCS(=O)(=O)c1ccccc1)Nc1ccccc1O] | UPHD-00104 | 347.4286 (Exact = 347.1191) | $C_{18}H_{21}O_4S$ | 2.99 | N-(2-hydroxyphenyl)-6-(phenylsulfonyl)hexanamide |

TABLE 1-continued

| Compound structure | ID | MW | EF | LogP | Name |
|---|---|---|---|---|---|
| 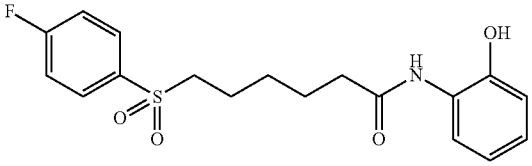 [SMILES: O=C(CCCCCS(=O)(=O)c1ccc(F)cc1)Nc1ccccc1O] | UPHD-00105 | 365.4191 (Exact = 365.1097) | $C_{18}H_{20}FNO_4S$ | 3.13 | 6-[(4-fluorophenyl)sulfonyl]-N-(2-hydroxyphenyl)hexanamide |
| 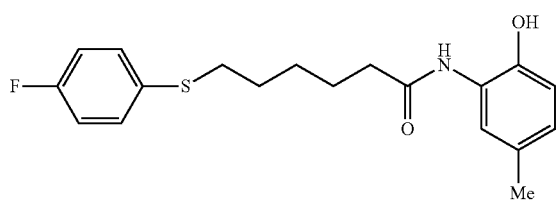 [SMILES: Cc1ccc(O)c(NC(=O)CCCCCSc2ccc(F)cc2)c1] | UPHD-00084 | 347.4469 (Exact = 347.1355) | $C_{19}H_{22}FNO_2S$ | 5.18 | 6-[(4-fluorophenyl)sulfanyl]-N-(2-hydroxy-5-methylphenyl)hexanamide |
| 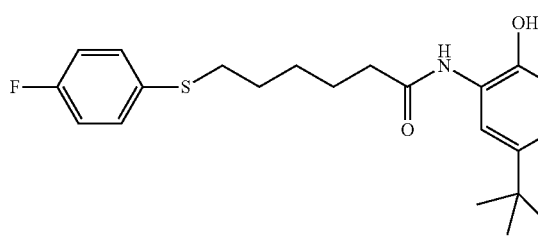 | UPHD-00083 | 389.5266 (Exact = 389.1825) | $C_{22}H_{28}FNO_2S$ | 6.21 | N-(5-tert-butyl-2-hydroxyphenyl)-6-[(4-fluorophenyl)sulfanyl]hexanamide |
| 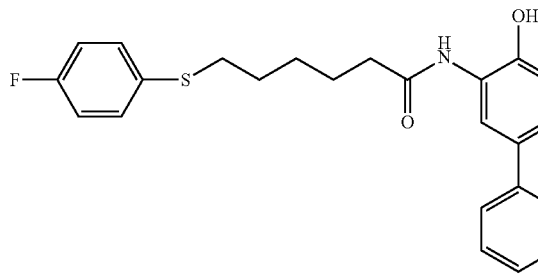 | UPHD-00082 | 406.5163 (Exact = 409.1512) | $C_{24}H_{24}FNO_2S$ | 6.31 | 6-[(4-fluorophenyl)sulfanyl]-N-(2-hydroxy-5-phenylphenyl)hexanamide |
| 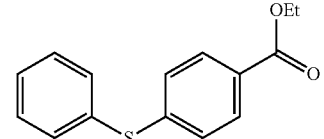 | UPHD-00056 | 258.3355 (Exact = 258.0715) | $C_{15}H_{14}O_2S$ | 4.52 | ethyl 4-(phenylsulfanyl)benzoate |
| 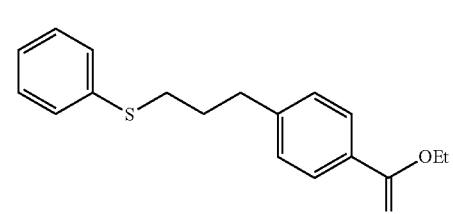 | UPHD-00096 | 300.4152 (Exact = 300.1184) | $C_{18}H_{20}O_2S$ | 5.32 | ethyl 4-[3-(phenylsulfanyl)propyl]benzoate |
| 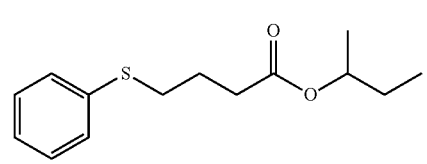 [SMILES: CCC(C)OC(=O)CCCSc1ccccc1] | VNK-I-154 | | | | (1-methylpropyl)-4-phenylsulfanyl)butanoate |
| 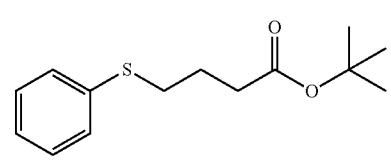 [SMILES: CC(C)(C)OC(=O)CCCSc1ccccc1] | VNK-I-157 | | | | n-butyl-4-(phenylsulfanyl)butanoate |

TABLE 1-continued

| Compound structure | ID | MW | EF | LogP | Name |
|---|---|---|---|---|---|
| 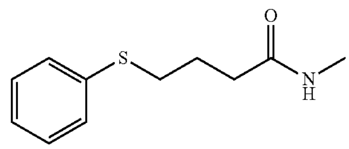 | VNK-I-259 | | | | 4-[phenylsulfanyl]-N-methylbutanamide |
| 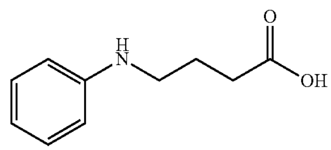 [SMILES: O=C(O)CCCNc1ccccc1] | VNK-I-300 | | | | 4-(phenylamino)butanoic acid |
| 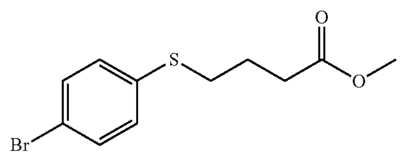 | VNK-I-290 | | | | methyl-4-(4-bromo-phenyl)sulfanyl)butanoate |
| 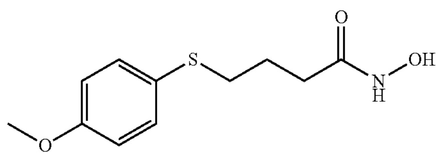 [SMILES: COc1ccc(SCCCC(=O)NO)cc1] | VNK-I-289 | | | | 4-[(4-methoxy-phenyl)sulfanyl]-N-hydroxybutanamide |
| 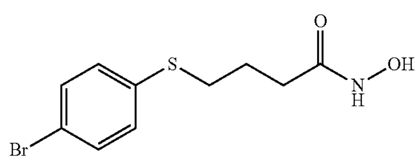 [SMILES: O=C(CCCSc1ccc(Br)cc1)NO] | VNK-I-292 | | | | 4-[(4-bromo-phenyl)sulfanyl]-N-hydroxybutanamide |
| 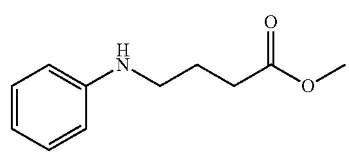 | VNK-I-298 | | | | methyl 4-(phenylamino)butanoate |

Pharmaceutically acceptable salts of any of the compounds described herein also may be used in the methods described herein. Pharmaceutically acceptable salt forms of the compounds described herein may be prepared by conventional methods known in the pharmaceutical arts, and include as a class veterinarily acceptable salts. For example and without limitation, where a compound comprises a carboxylic acid group, a suitable salt thereof may be formed by reacting the compound with an appropriate base to provide the corresponding base addition salt. Non-limiting examples include: alkali metal hydroxides, such as potassium hydroxide, sodium hydroxide and lithium hydroxide; alkaline earth metal hydroxides, such as barium hydroxide and calcium hydroxide; alkali metal alkoxides, such as potassium ethanolate and sodium propanolate; and various organic bases such as piperidine, diethanolamine, and N-methylglutamine.

Acid and base addition salts may be prepared by contacting the free base form with a sufficient amount of a desired acid or base to produce the salt in a manner known in the art. The free base may be regenerated by contacting the salt form with a base or acid (depending on the nature of the salt) and isolating the free base. The free base forms differ from their respective salt forms somewhat in certain physical properties such as solubility in polar solvents, but otherwise the salts are equivalent to their respective free base forms for purposes described herein.

Compounds comprising basic nitrogen-containing groups may be quaternized with such agents as $C_{1-4}$ alkyl halides, such as methyl, ethyl, iso-propyl and tert-butyl chlorides, bromides and iodides; $C_{1-4}$ alkyl sulfate such as dimethyl, diethyl and diamyl sulfates; $C_{10-18}$ alkyl halides, such as decyl, dodecyl, lauryl, myristyl and stearyl chlorides, bromides and iodides; and aryl-$C_{1-4}$ alkyl halides, such as benzyl chloride and phenethyl bromide. Such salts permit the preparation of both water-soluble and oil-soluble compounds.

Non-limiting examples of pharmaceutically-acceptable base salts include: aluminum, ammonium, calcium, copper, ferric, ferrous, lithium, magnesium, manganic, manganous, potassium, sodium, and zinc salts. Salts derived from pharmaceutically acceptable organic non-toxic bases include, without limitation: salts of primary, secondary, and tertiary amines, substituted amines including naturally occurring substituted amines, cyclic amines, and basic ion exchange resins, such as arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine, and tris-(hydroxymethyl)-methylamine (tromethamine).

Acid addition salts may be prepared by treating a compound with pharmaceutically acceptable organic and inorganic acids, including, without limitation: hydrohalides, such as hydrochloride, hydrobromide, hydroiodide; other mineral acids and their corresponding salts such as sulfates, nitrates, and phosphates; alkyl- and mono-arylsulfonates, such as ethanesulfonate, toluenesulfonate, and benzenesulfonate; and other organic acids and their corresponding salts, such as acetate, tartrate, maleate, succinate, citrate, benzoate, salicylate, and ascorbate.

Non-limiting examples of pharmaceutically-acceptable acid salts include: acetate, adipate, alginate, arginate, aspartate, benzoate, besylate (benzenesulfonate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate, galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate, and phthalate.

Multiple salts forms are also considered to be pharmaceutically-acceptable salts. Common, non-limiting examples of multiple salt forms include: bitartrate, diacetate, difumarate, dimeglumine, diphosphate, disodium, and trihydrochloride.

As such, "pharmaceutically acceptable salt" as used herein is intended to mean an active ingredient (drug) comprising a salt form of any compound as described herein. The salt form preferably confers to the improved and/or desirable pharmacokinetic/pharmodynamic properties of the compounds described herein.

In use, any compound described herein, including pharmaceutically acceptable salts thereof, may be admixed with any pharmaceutically acceptable carrier or carriers, such as water, saline, physiological salt solutions, Ringer's solution or any other carrier customarily used for administration of drugs to the subject in question (see, generally, Troy, D B, Editor, Remington: The Science and Practice of Pharmacy, 21st Ed., Lippincott Williams & Wilkins (2005), pp. 745-849 for descriptions of various compositions, solutions, and dosage forms useful for administration of the described compounds, as well as methods of making such compositions, solutions, and dosage forms).

According to one non-limiting example, the compounds described herein are formulated into a composition with one or more pharmaceutical vehicles or diluents for oral, intravenous or subcutaneous administration. The composition can be formulated in a classical manner using solid or liquid vehicles, diluents and additives appropriate to the desired mode of administration. Orally, the compounds can be administered in the form of tablets, capsules, granules, powders and the like.

In any case, as used herein, any agent or agents used for improving kidney function, inhibiting a histone deacylase in a cell, expanding a population of renal progenitor cells and/or stimulating kidney repair in cells in vitro, ex vivo or in vivo is administered in an amount effective to improve kidney function, to inhibit a histone deacylase in a cell, to expand renal progenitor cells and/or to stimulate kidney repair in cells in vitro, ex vivo or in vivo, namely in an amount and in a dosage regimen effective to improve kidney function, inhibit a histone deacylase in a cell, expand renal progenitor cells and/or stimulate kidney repair in cells in vitro, ex vivo or in vivo. According to one non-limiting embodiment, an effective dose ranges from 0.05 to 200 mg/kg/day, and in certain embodiments less than 100 mg/kg/day, including any increment or range therebetween, including 0.1 mg/kg/day, 0.5 mg/kg/day, 1 mg/kg/day, 5 mg/kg/day, 10 mg/kg/day, 20 mg/kg/day, 25 mg/kg/day, 50 mg/kg/day, 75 mg/kg/day, 100 mg/kg/day, etc. However, for each compound described herein, an effective dose or dose range is expected to vary from that of other compounds described herein for any number of reasons, including the molecular weight of the compound, bioavailability in the dosage form, route of administration, specific activity (e.g., $EC_{50}$), etc. In vitro (including ex vivo), the composition is used, for example, in culture medium. Exemplary and non-limiting effective ranges range from 100 nM to 25 µM, 200 nM to 3 µM, 200 nM to 1.5 µM, including all increments therebetween. Once again, the effective range and optimal concentration range depends on the specific activity (e.g., $EC_{50}$) of the composition, as well as a variety of other conditions. In any case, the effective range (e.g., the therapeutic window) between the minimally-effective dose, and maximum tolerable dose in a subject can be determined empirically by a person of skill in the art, with end points being determinable by in vitro and in vivo assays, such as those described herein and/or are acceptable in the pharmaceutical and medical arts for obtaining such information regarding agents, such as histone deacetylase inhibitors. Different concentrations of the agents described herein are expected to achieve similar results. The compounds can be administered orally one or more times daily, for example two to four times daily, once every two, three, four, five or more days, weekly, monthly, etc., including increments therebetween. In certain delivery methods, it is possible to deliver the drug continuously, or substantially continuously as in the case of, for example, intravenous or transdermal delivery routes. A person of ordinary skill in the pharmaceutical and medical arts will appreciate that it will be a matter of design choice and/or optimization to identify a suitable dosage regimen for improving kidney function, inhibiting a histone deacylase in a cell, expand renal progenitor cells and/or stimulating kidney repair in cells in vitro, ex vivo or in vivo.

The compounds described herein may be administered in any manner that is effective to improve kidney function, inhibit a histone deacylase in a cell, expand a renal progenitor cell population and/or stimulate kidney repair in cells in vitro, ex vivo or in vivo. Examples of delivery routes include, without limitation: topical, for example, epicutaneous, inhalational, enema, ocular, otic and intranasal delivery; enteral, for example, orally, by gastric feeding tube or swallowing, and rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal, with oral or inravenous approaches being preferred for improving kidney function, inhibiting a histone deacylase in a cell, expanding a population of renal progenitor cells and/or stimulating kidney repair in cells in vitro, ex vivo or in vivo.

Therapeutic/pharmaceutical compositions are prepared in accordance with acceptable pharmaceutical procedures, such as described in Remington: The science and Practice of Pharmacy, 21st edition, ed. Paul Beringer et al., Lippincott, Williams & Wilkins, Baltimore, Md. Easton, Pa. (2005) (see, e.g., Chapters 37, 39, 41, 42 and 45 for examples of powder, liquid, parenteral, intravenous and oral solid formulations and methods of making such formulations).

Any of the compounds described herein may be compounded or otherwise manufactured into a suitable composition for use, such as a pharmaceutical dosage form or drug product in which the compound is an active ingredient. According to one example, the drug product described herein is an oral tablet, capsule, caplet, liquid-filled or gel-filled capsule, etc. Compositions may comprise a pharmaceutically acceptable carrier, or excipient. An excipient is an inactive substance used as a carrier for the active ingredients of a medication. Although "inactive," excipients may facilitate and aid in increasing the delivery, stability or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

According to one non-limiting embodiment, the compounds described herein are complexed with a cyclodextrin. Cyclodextrins are compounds that have found substantial recognition as excipients (e.g., as carriers, vehicles, etc.) in the pharmaceutical field, for example in oral and intravenous dosage forms. Cyclodextrins are able form non-covalent inclusion complexes and/or aggregates in solution with poorly soluble drugs, for example, BCS Class II and IV drugs (high or low intestinal permeability, respectively, but low solubility in both instances). Cyclodextrins are cyclic oligosaccharides having a hydrophilic outer surface and a lipophilic central cavity. They consist of α-1,4-linked α-D-glucopyranose units. Naturally-occurring cyclodextrins include α-, β- and γ-cyclodextrins, with 6, 7 and 8 glucopyranose units, respectively. The natural cyclodextrins can be used orally or topically, but natural 3-cyclodextrin and γ-cyclodextrin cannot be used parenterally. A number of cyclodextrin derivatives have been formulated with various usefulness in different administrative routes. Common, non-limiting examples of cyclodextrin derivatives include hydroxypropyl-β-cyclodextrin (e.g., 2-hydroxypropyl-β-cyclodextrin), hydroxypropyl-γ-cyclodextrin (e.g., 2-hydroxypropyl-γ-cyclodextrin), hydroxyethyl-β-cyclodextrin, randomly methylated β-cyclodextrin, methyl-β-cyclodextrin, dimethyl-β-cyclodextrin, permethylated β-cyclodextrin, sulfobutylether β-cyclodextrin (e.g., sodium salt), sulfobutyl-γ-cyclodextrin, branched cyclodextrin (e.g., glucosyl-β-cyclodextrin or maltosyl-β-cyclodextrin, e.g., 6-O-maltosyl-β-cyclodextrin or glucosyl-β-cyclodextrin) and randomly-acetylated amorphous-β-cyclodextrin. Cyclodextrins may be complexed with a drug as inclusion complexes (included) in a solution in a 1:1 molar ratio, though increased or decreases relative amounts of the drug or cyclodextrin may be used during formulation in order to drive the reaction. Where the drug is aggregated instead of included within the cyclodextrin, an excess of cyclodextrin may be utilized. It should be recognized that the inclusion or aggregation process can be optimized, including manipulation of relative cyclodextrin-to-active ingredient ratios to obtain optimal solubility and bioavailability or other desirable features of the end-product.

A complete description of the state of the art of the uses of cyclodextrins as pharmaceutical excipients is beyond the scope of this document. To this end, see, Loftsson et al. "Self-Association of Cyclodextrins and Cyclodextrin Complexes" J. Pharm. Sci. 93(5):1091-1099 (2004); Loftsson et al. "Cyclodextrins in Drug Delivery" Expert. Opin. Drug Deliv. 2:335-351 (2005); Brewster et al. "Cyclodextrins as Pharmaceutical Solubilizers" Advanced Drug Delivery Reviews 59:645-666 (2007); and Rasheed et al., "Cyclodextrins as Drug Carrier Molecule: A review" Sci. Pharm. 76:567-598 (2008) for their description of cyclodextrins and uses thereof in the pharmaceutical arts. As used herein, "a cyclodextrin" or "cyclodextrins" refer not only to naturally-occurring α-, β- and γ-cyclodextrins, but to cyclodextrin derivatives, including but not limited to those mentioned above. Likewise "α-cyclodextrin(s)", "β-cyclodextrin(s)" and "γ-cyclodextrins" refer both to the naturally-occuring cyclodextrin and to cyclodextrin derivatives (e.g., "a β-cyclodextrin" includes both β-cyclodextrin and β-cyclodextrin derivatives, such as, without limitation, hydroxypropyl-β-cyclodextrin, hydroxyethyl-β-cyclodextrin, randomly methylated β-cyclodextrin, methyl-β-cyclodextrin, dimethyl-β-cyclodextrin, permethylated β-cyclodextrin, sulfobutylether β-cyclodextrin, branched β-cyclodextrin, etc.).

According to another non-limiting embodiment, the formulation is a liposome or multiphase (a liquid comprising more than one phase, such as oil in water, water in oil, liposomes or multi-lamellar structures) composition. Multiphase systems, including liposomes, are prevalent in the pharmaceutical arts. In the case of a liposome, the drug product might comprise a phospholipid, a non-ionic detergent, and a cationic lipid, such as a composition comprising a phosphatidyl choline, a non-ionic surfactant, and a quaternary ammonium salt of a lipid-substituted D or L glutamic acid or aspartic acid, and an aqueous solvent. The liposomes or multiphase liquids and the ingredients thereof are pharmaceutically acceptable. They are typically formulated using an aqueous solvent, such as water, normal saline or PBS.

Phospholipids include any natural or synthetic diacylglyceryl phospholiopid (such as phosphatidyl choline, phosphotidylethanolamine, phosphotidylserine, phosphatidylinositol, phosphatidylinositol phosphate, etc) and phosphosphingolipid that is capable of forming self-assembling liposomes. In one example the phospolipid is a phosphatidyl choline, a compound that comprises a choline head group, glycerophosphoric acid and fatty acid. Phosphatidyl choline can be obtained from eggs, soy or any suitable source and can be synthesized.

A nonionic surfactant is a surfactant containing no charged groups. Nonionic surfactants comprise a hydrophilic head group and a lipophilic tail group, such as a single- or double-lipophilic chain surfactant. Examples of lipophilic tail groups include lipophilic saturated or unsaturated alkyl groups (fatty acid groups), steroidal groups, such as cholesteryl, and vitamin E (e.g., tocopheryl) groups, such as a polysorbate (a polyoxyethylene sorbitan), for example Tween 20, 40, 60 or 80. More broadly, non-ionic surfactants include: glyceryl esters, including mono-, di- and tri-glycerides; fatty alcohols; and fatty acid esters of fatty alcohols or other alcohols, such as propylene glycol, polyethylene glycol, sorbitan, sucrose and cholesterol.

A cationic lipid is a compound having a cationic head and a lipophilic tail. Included are cationic lipids that are quaternary ammonium salts, such as quaternary ammonium salts of lipid-substituted D and L glutamic acid or aspartic acid, such as glutamic acid dialkyl amides, including for example L-glutamic acid-1,5,-dioleyl amide. Other commercially-available examples of cationic lipids (e.g., available from Avanti Polar Lipids) include DC-Cholesterol (3β-[N—(N', N'-dimethylaminoethane)-carbamoyl]cholesterol hydrochloride), DOTAP (e.g., 1,2-dioleoyl-3-trimethylammonium-propane (chloride salt)), DODAP (e.g., 1,2-dioleoyl-3-dimethylammonium-propane), DDAB (e.g., Dimethyldioctadecylammonium (Bromide Salt)), ethyl-PC (e.g., 1,2-dilauroyl-sn-glycero-3-ethylphosphocholine (chloride salt)) and DOTMA (e.g., 1,2-di-O-octadecenyl-3-trimethylammonium propane (chloride salt)).

The ratio of ingredients (phospholipid:nonionic surfactant:cationic lipid) can vary greatly, so long as a useful multilamellar structure is obtained that is able to deliver the active agents described herein. Further, each different combination of ingredients might have different optimal ratios. The ability to determine optimal ratios does not require undue experimentation because the ability of any formulation to deliver the active agent is readily tested as described herein, and as is generally known in the pharmaceutical arts. Liposome and multilamellar structures are common delivery vehicles for active agents and their manufacture, physical testing and biological assays to determine effectiveness are well-known. Useful phospholipid:nonionic surfactant:cationic lipid ratios include, for example: from 0.1-10:0.1-10: 0.1-10 (w/w), and in certain instances the nonionic surfactant:cationic lipid (w/w) ratio is approximately the same and/or the phospholipid constituent is from 2 to 10 times (w/w) that of the nonionic surfactant and cationic lipid.

In use, a compound having the formula, e.g., as described herein:

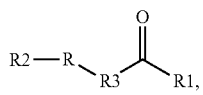

in which
R is S, S(O), S(O)$_2$ or NH,
R1 is —NHR4 where R4 is OH, aminophenyl, hydroxyphenyl, $C_{1-4}$ alkyl hydroxyphenyl or phenyl hydroxyphenyl, or —OR5 where R5 is H or $C_{1-4}$ alkyl,
R2 is phenyl, substituted phenyl,

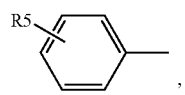

where R5 is halo; methyl; $C_{1-4}$ alkyl; methoxy, $C_{1-4}$ alkoxy; naphthyl, 1H-1,3-benzodiazol-2-yl, 1,3-benzothiazol-2-yl, pyrimidinyl, 1-methyl-1H-1,3benzodiazol-2-yl, pyridyl, methoxyphenyl, methylthiophenyl, and
R3 is from 0 to 5 methylene groups ((—CH$_2$—)$_{0-5}$) and 0 or 1 phenylene wherein at least one methylene or phenylene is present, or a pharmaceutically acceptable salt thereof, whether or not incorporated as a drug product, is useful and finds use in: methods of improving kidney function; methods of expanding renal progenitor cells in a kidney or in vitro, for example a damaged kidney (including damaged, injured, defective or otherwise deficient); and methods of inhibiting a histone deacetylase in a cell. In any such method, the compound or composition is used in an amount effective to achieve the stated goal, whether it is improving kidney function; expanding renal progenitor cells in a kidney or in vitro or inhibiting a histone deacetylase in a cell. Suitable end-points for each method are provided herein. Where the method is for improving kidney function in a patient, the method has an end point of improving one or more detectable parameters indicative of kidney function, for example and without limitation moving abnormal Blood Urea Nitrogen (BUN) levels in a patient towards normal levels, or expansion of renal progenitor cell populations in a kidney. Exemplary assays showing inhibition of histone acetylase are provided herein. Likewise, assays demonstrative of the ability of a compound to expand a renal progenitor cell population are provided herein.

Example 1—Identification of PTBA as a Lead Compound

A chemical screen of approximately 2000 small molecules in zebrafish embryos identified a compound that generated pericardial edema, suggesting aberrant renal development. Treatment with this compound, 4-(phenylthio) butanoic acid (PTBA), increased the size of the pronephric kidney in zebrafish. Earlier in development, PTBA expanded the expression of renal progenitor cell markers, including lhx1a, pax2a, and pax8. Blocking DNA synthesis with hydroxyurea and aphidicolin before PTBA treatment decreased its efficacy, suggesting that PTBA-mediated renal progenitor expansion is proliferation dependent. Structure-activity analysis revealed that PTBA was an analog of the known histone deacetylase inhibitors (HDACis) 4-phenylbutanoic acid (PBA) and trichostatin A (TSA). Like PTBA, PBA and TSA both demonstrated the ability to expand lhx1a expression in treated embryos. PTBA was subsequently confirmed to function as an HDACi both in vitro and in vivo. HDACis are hypothesized to stimulate retinoic acid (RA) signaling by decreasing the concentration of RA necessary to activate RA receptors (RARs) on target genes. Indeed, treatment with PTBA affected the expression of the RA-responsive genes, cyp26a1 and cmlc2, in a manner consistent with increased RA signaling. Furthermore, blocking the RA pathway with a dominant-negative RARα construct decreased PTBA efficiency. Therefore, PTBA appears to stimulate renal progenitor cell proliferation by activating the RA-signaling pathway. HDACis have been shown to improve renal recovery following acute kidney injury. Since PTBA increases renal progenitor cell proliferation, it may exert similar effects on the multipotent cells involved in regeneration. In an effort to improve PTBA efficacy for pharmacological applications, analogs were generated by modifying the key structural elements of the general HDACi pharmacophore. These were tested along with a panel of known HDACis for their ability to increase lhx1a expression in treated embryos. Several compounds were characterized that function at nanomolar concentrations and do not cause toxicity in kidney cell culture. These second generation PTBA analogs are excellent candidates for development as potential renal therapeutics.

A scan was performed using an unbiased chemical library on zebrafish embryos, seeking small molecules capable of generating edemic phenotypes. Since edema may reflect renal dysfunction, it was hoped to identify compounds capable of interfering with normal pronephric development (Drummond, I. A. Kidney development and disease in the zebrafish. J Am Soc Nephrol 16, 299-304, (2005)). Determining the mechanisms of such compounds would provide insight into the molecular events guiding the specification of renal progenitor cells. Of the almost 2000 compounds tested, only four caused embryos to develop edema by the 72 hours-post fertilization (hpf) endpoint. One of these, 4-(phenylthio)butanoic acid (PTBA), demonstrated the ability to increase the expression of renal progenitor cell markers. It is hypothesized herein that PTBA increases the number of renal progenitor cells, resulting in aberrant pronephric development.

Results

Figure 2:
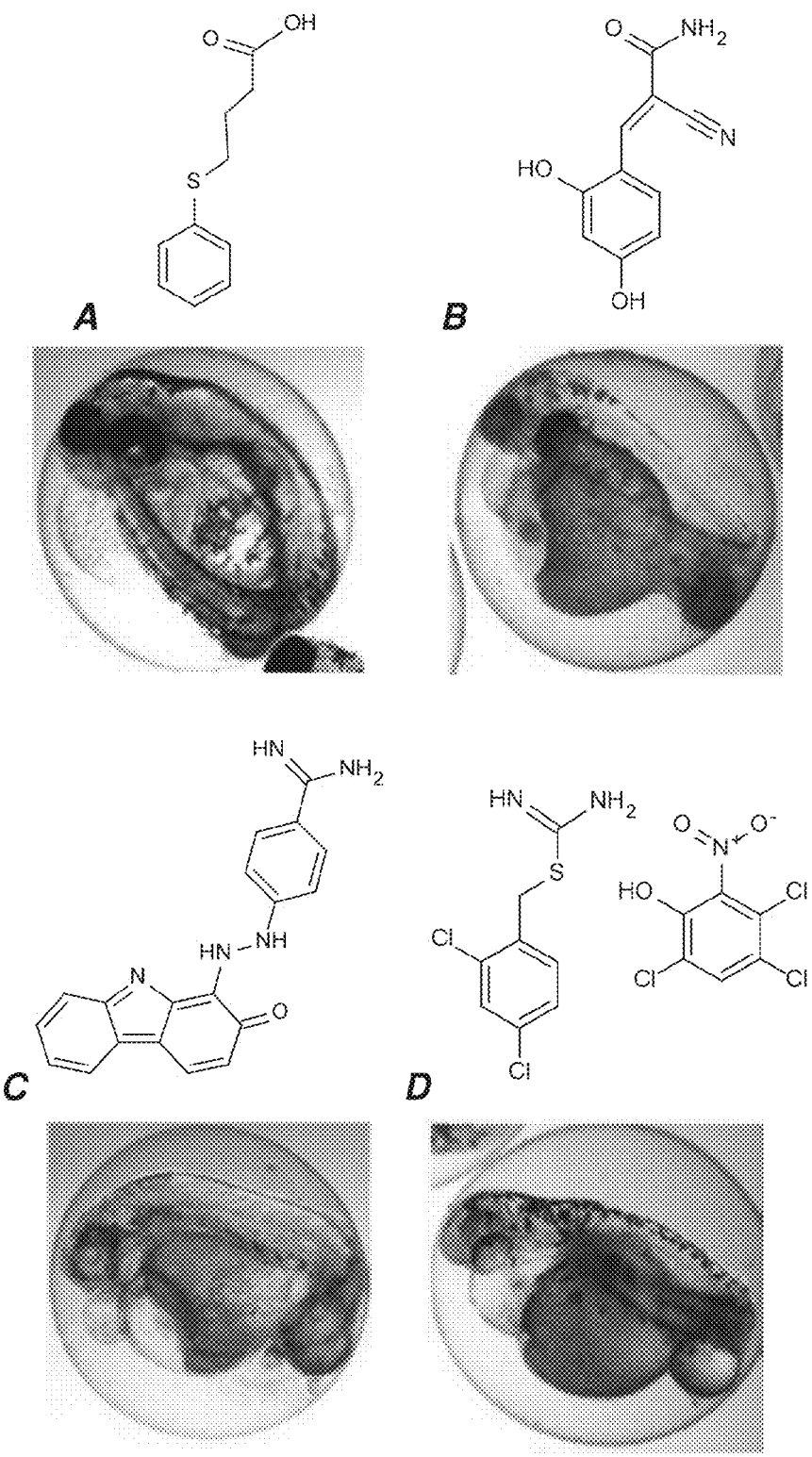
FIG. 2. Four compounds causing pericardial edema in the initial phenotypic screen. (A through D) Top panels: chemical structures of NSC115787 (A), NSC134664 (B), NSC357777 (C), or NSC35400 (D). Bottom panels: edemic phenotypes in 72 hours post-fertilization (hpf) larvae treated with the corresponding compounds at 10 µM.

PTBA Causes Edema in Zebrafish Larvae:

The initial chemical screen using a library of small molecules was performed with diverse structures. It was observed that 61 compounds (3%) were lethal and identified four compounds (NSC115787, NSC134664, NSC357777, and NSC35400, A-D in FIG. 2) that generated pericardial edema in treated zebrafish larvae at 72 hpf (FIG. 2, bottom panel).

In situ hybridization determined that treatment with NSC134664, NSC357777, or NSC35400 (a disconnected structure) did not affect the size of the kidney field (data not shown). However, it was observed that treatment with various concentrations of 4-(phenylthio) butanoic acid (PTBA, NSC115787) appeared to expand the expression of some renal markers during pronephric development (data not shown). PTBA was synthesized and purified for use in all subsequent studies.

Figure 3:
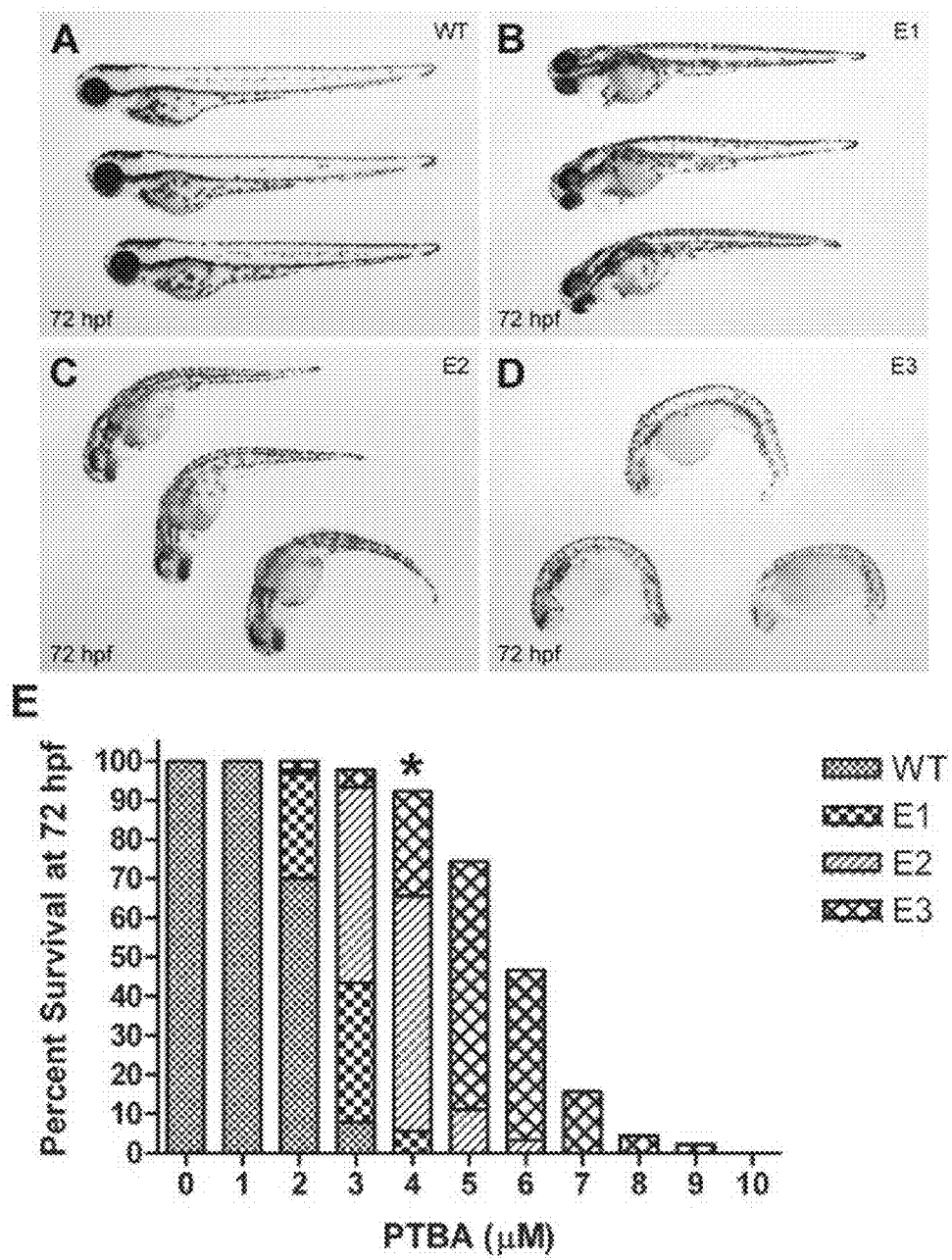
FIG. 3. PTBA elicits concentration-dependent effects on larval edema and survival. (A through D) Embryos were treated with 0 to 10 µM PTBA from 2 hpf, and larvae were scored at 72 hpf using a phenotype-based classification system (see Methods). (A) Wild-type (WT). (B) Edemic 1 (E1). (C) Edemic 2 (E2). (D) Edemic 3 (E3). (E) Graph of phenotypes after treatment with 0 to 10 µM PTBA (n=90 per concentration). Asterisk denotes lowest PTBA concentration that exhibits a significant effect ($p<0.05$) on survival.

PTBA Expands the Kidney Field:

To determine the concentration of PTBA that maximized efficacy, while minimizing toxicity, concentration-response experiments were performed. Treatment with 3 μM PTBA caused 92% (n=88) of the embryos to develop an edemic phenotype by 72 hpf without causing significant death (FIG. 3). Therefore, 3 μM PTBA was chosen as the working concentration. All embryos treated with 10 μM PTBA (n=90), the concentration used in the initial screen, died before 72 hpf (FIG. 3). This discrepancy probably reflects the concentration variability common in small molecule libraries.

Figure 4:
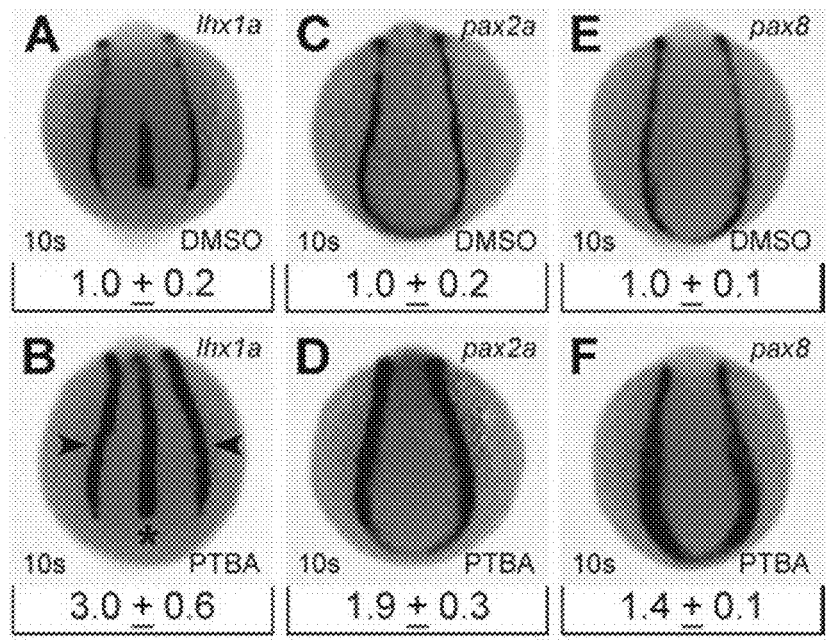
FIG. 4. PTBA treatment increases the expression of renal progenitor markers. (A through F) In situ hybridization for lhx1a (A and B), pax2a (C and D), or pax8 (E and F), in 10-somite embryos treated with 0.5% DMSO (A, C, and E) or 3 µM PTBA (B, D, and F). Arrowheads indicate renal progenitor cells, asterisk indicates notochord. Relative qPCR in the trunk region of 10-somite embryos (n=4, 60 embryos per group) is displayed under the corresponding in situ image. Data are mean expression with 95% confidence interval, determined as described below.

The edemic phenotypes elicited by PTBA treatment prompted examination of whether the compound affects renal progenitor cells. To address this, expression patterns and relative abundance of lhx1a, pax2a, and pax8 were determined at the 10-somite stage (14 hpf). This developmental stage occurs just after specification of the first renal progenitor cells. Lhx1a expression was expanded in 95% of embryos treated with PTBA (n=60) as compared with controls (n=60) (FIGS. 4, A and B). This represented a threefold increase in relative transcript as determined by quantitative real-time PCR (qPCR; FIGS. 4, A and B). Increased lhx1a expression appeared in the bilateral stripes of intermediate mesoderm that give rise to the pronephros (FIG. 4B, arrowheads), as well as in the axial mesoderm (notochord; FIG. 4B, asterisk).

Figure 5:
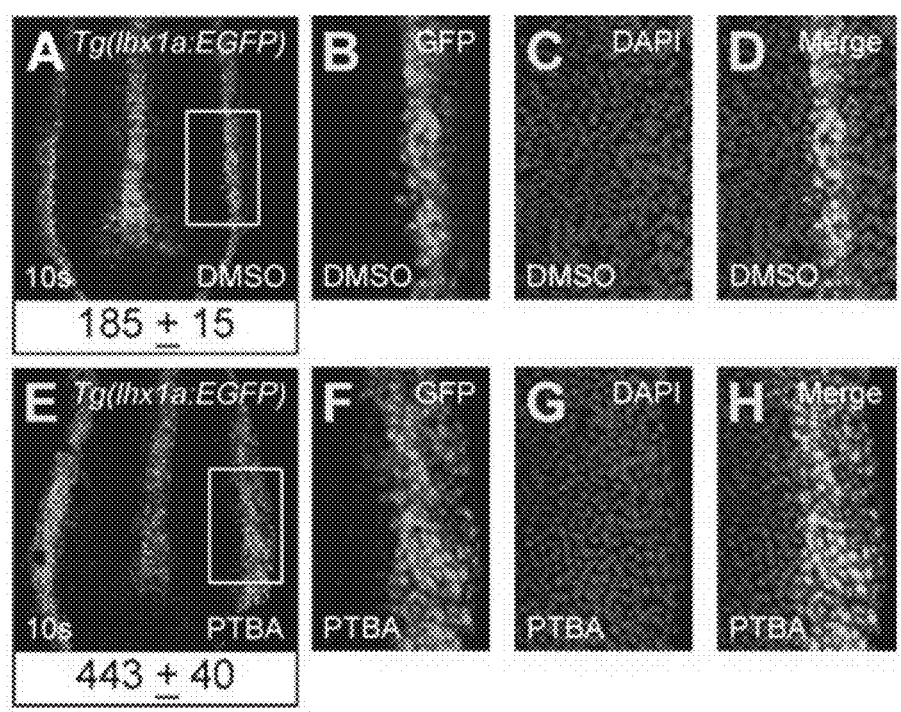
FIG. 5. PTBA treatment increases the number of renal progenitor cells. (A through H) Confocal projections of 10-somite Tg(lhx1a:EGFP)pt303 embryos treated with 0.5% DMSO (n=18 [A through D]) or 3 µM PTBA (n=21 [E through H]). Boxed areas (A and E) were counted for GFP- and DAPI-positive nuclei and are shown in B and F (GFP), C and G (DAPI), and D and H (merge). Cell counts are mean number of positive cells plus 95% confidence interval (A and E).

The expression domains of pax2a and pax8 were also expanded in 95% and 97% of treated embryos, respectively, (n=60, pax2a; n=59, pax8) as compared with controls (n=60, pax2a; n=59, pax8) (FIG. 4, C through F). This accounted for an almost two-fold increase in pax2a expression and a 50% increase in pax8 expression as determined by qPCR (FIG. 4, C through F). Although these studies demonstrated that PTBA treatment resulted in increased gene expression, they did not indicate whether there are more renal progenitor cells or simply higher expression levels per cell. To differentiate between these two possibilities, the Tg(lhx1a:EGFP) p$^{r33}$ reporter line (Swanhart, L. M. et al. Characterization of an lhx1a transgenic reporter in zebrafish. Int J Dev Biol 54, 731-736, (2010)) was treated with PTBA and counted the number of renal progenitor cells. As compared with control embryos, PTBA-treated embryos showed a 2.4-fold increase in the number of renal progenitor cells (FIG. 5, A through H).

Figure 6:
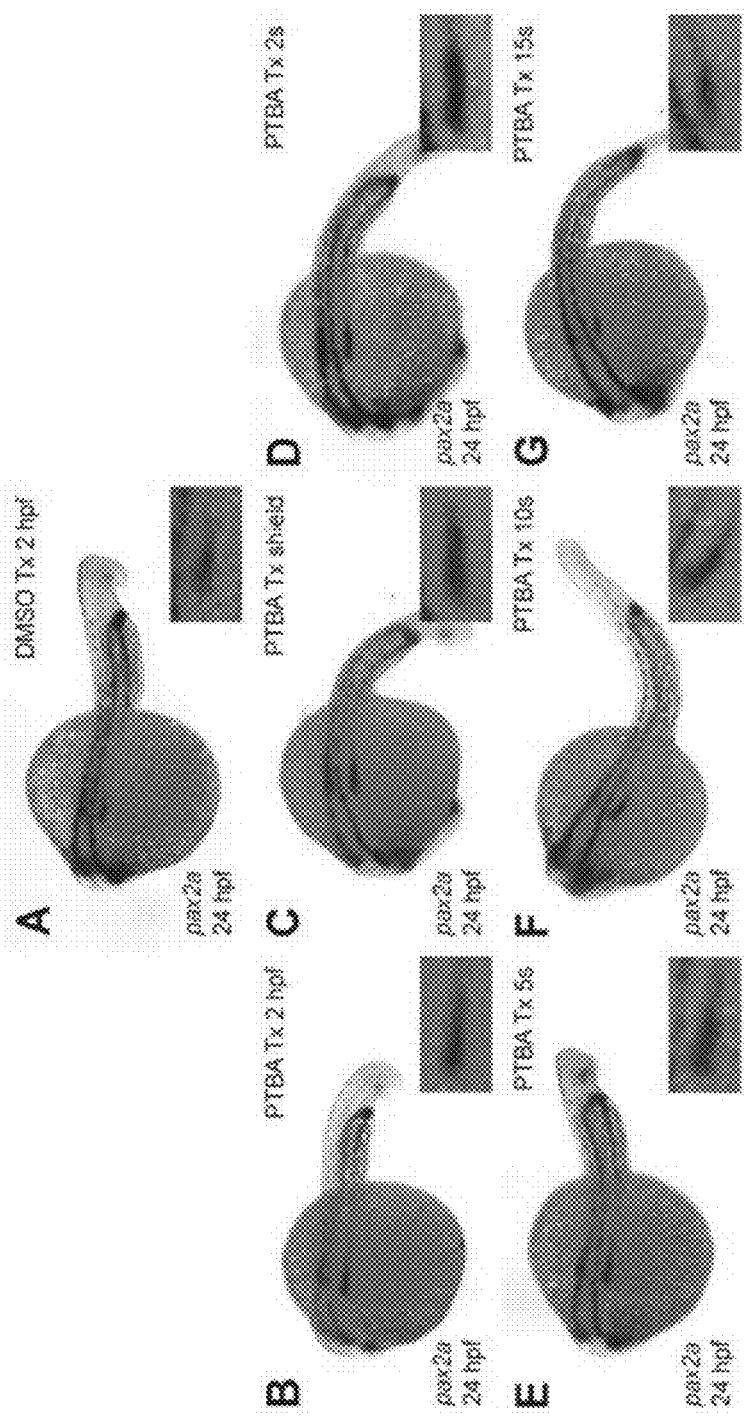
FIG. 6. PTBA is effective during renal progenitor cell specification. (A through G) In situ hybridization for pax2a in 24 hpf embryos treated with 0.5% DMSO from 2 hpf (A, n=132) or 3 µM PTBA from: 2 hpf (B, n=67), shield (C, 6 hpf, n=100), 2 somites (D, 10.7 hpf, n=71), 5 somites (E, 11.7 hpf, n=87), 10 somites (F, 14 hpf, n=89), or 15 somites (G, 16.5 hpf, n=72). Insets are pax2a enlargements (lower field).

PTBA is Effective During Specification:

Initiation of PTBA treatments between 2 hpf and 14 hpf (10 somites) resulted in expanded pax2a expression at 24 hpf (FIG. 6, A through F). However, beginning treatment at 16.5 hpf (15 somites) resulted in no kidney field expansion (FIG. 6G). It was later determined that initiating treatments at 15 somites or later did not affect the functional kidney as assayed by a lack of edema in 72 hpf larvae (n=90, data not shown). Thus, the effective temporal treatment window exhibited by PTBA coincides with the period when renal progenitor cells are specified.

Figure 7:
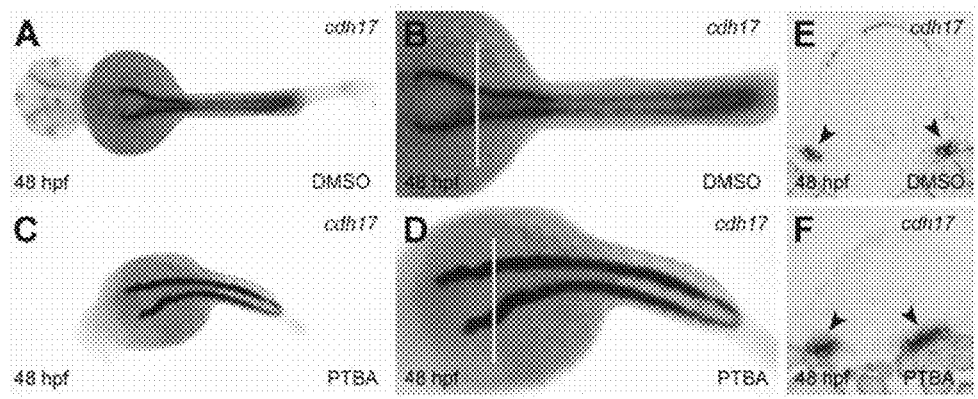
FIG. 7. PTBA treatment expands cdh17 expression. (A through D) In situ hybridization for cdh17 expression in 48 hpf embryos treated with 0.5% DMSO (A [magnified in B]) or 3 µM PTBA (C [magnified in D]). (E and F) Proximal tubule cross-sections (5 µm) taken from cdh17 in situ hybridizations of 48 hpf embryos treated with 0.5% DMSO (E) or 3 µM PTBA (F). Cross-sections were taken from the locations indicated in B and D by yellow lines.
Figure 8:
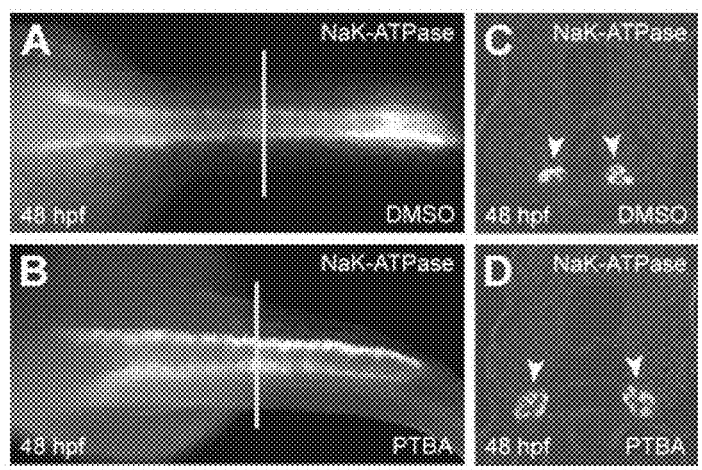
FIG. 8. PTBA treatment expands NaK-ATPase expression. (A and B) Whole-mount antibody staining for NaK-ATPase in 48 hpf embryos treated with 0.5% DMSO (A) or 3 µM PTBA (B). (C and D) Distal tubule cross-sections (5 µm) taken from NaK-ATPase antibodystained 48 hpf embryos treated with 0.5% DMSO (C) or 3 µM PTBA (D). White arrowheads indicate NaK-ATPase protein expression. Cross-sections were taken from the locations indicated in A and B by yellow lines.

PTBA Increases Pronephric Size:

To determine whether PTBA treatment resulted in a transient or persistent expansion of the kidney field, the kidney at 48 hpf was examined using markers of glomerulus and tubule. As compared with controls (n=54), 89% of PTBA-treated embryos (n=56) displayed an expansion of the pan-tubule marker cdh17 (FIG. 7, A through D). Cross-sections from the proximal region of the cdh17 expression domain confirmed the expansion (FIGS. 7, E and F). Pronephric expansion at the protein level was also assessed by examining the expression of NaK-ATPase, another pan-tubule marker (FIGS. 8, A and B). As compared with controls (n=10), 100% of PTBA-treated embryos (n=10) exhibit expansion of NaK-ATPase protein expression. Cross-sections taken from the distal region of the NaK-ATPase expression domain show an increase in tubular diameter consistent with that observed with cdh17. (FIGS. 8, C and D, compare with FIGS. 7, E and F).

Figure 9:
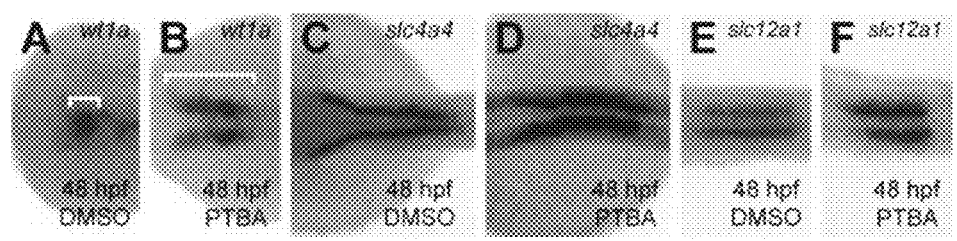

To determine if PTBA exhibits any segment-specific effects on the size of the pronephros, markers of podocytes (wt1a), proximal tubule (slc4a4), and distal tubule (slcl2a1) were examined. As compared with controls (n=57, 58, and 56, respectively), PTBA-treated embryos exhibited 74% expansion of wt1a (n=50), 92% expansion of slc4a4 (n=60), and 64% expansion of slcl2a1 (n=59) (FIG. 9). These results argue that PTBA treatment likely causes expansion of the entire pronephros. Furthermore, while the wt1a expression domains in control embryos have migrated to the midline by 48 hpf, the domains of PTBA-treated embryos remain separated (FIGS. 9, A and B). Since wt1a is essential for proper glomerular morphogenesis, this misexpression may contribute to a loss of kidney function. This observation could explain the edemic phenotypes associated with PTBA treatment.

Figure 10:
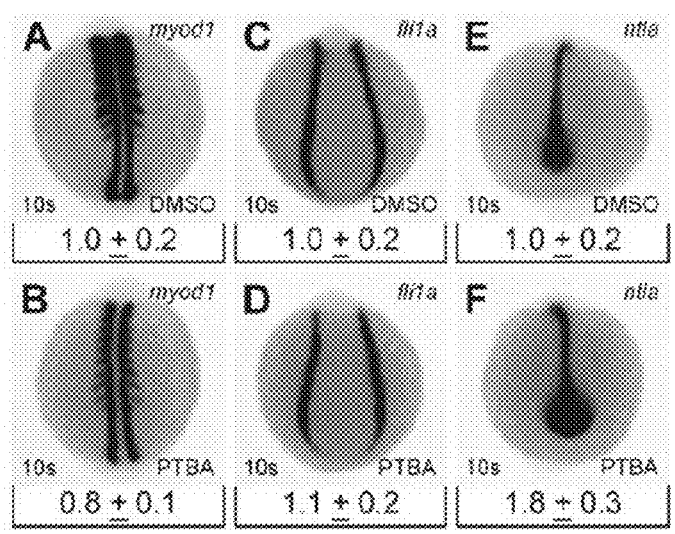
FIG. 10. PTBA treatment does not transform nearby tissues to a renal fate. (A through F) In situ hybridization for the mesodermal markers myod1 (A and B), fli1a (C and D), and ntla (E and F) in 10-somite embryos treated with 0.5% DMSO (A, C, and E) or 3 µM PTBA (B, D, and F). Relative mRNA abundance in the trunk region of 10-somite embryos (n=4, 60 embryos per group) is displayed under the corresponding in situ image. Data are mean expression with 95% confidence interval, determined as described below.

PTBA does not Transform Neighboring Tissues to a Kidney Fate:

The PTBA-mediated increase in kidney field size could result from the transformation of nonrenal cells to a renal progenitor fate. To assess this possibility, the effects of PTBA on markers of two mesodermal tissues juxtaposed to renal progenitor cells was examined: myod1 (somites) and fli1a (vasculature). By in situ hybridization, it was observed that myod1 expression was slightly decreased in 95% of PTBA-treated embryos (n=60) at the 10-somite stage, as compared with controls (n=60) (FIGS. 10, A and B). However, subsequent qPCR analysis did not confirm the significance of this observed decrease (FIGS. 10, A and B). Expression of fli1a remained unchanged in 97% of PTBA-treated embryos (n=60), as compared with controls (n=59), and as assayed by qPCR (FIGS. 10, C and D).

In addition to increased lhx1a expression in renal progenitor cells, increased lhx1a expression in the notochord (FIG. 4B, asterisk) was observed. To determine whether this expansion reflected an effect on notochord size or a general increase in lhx1a expression, the notochord-specific marker ntla was assayed. It was observed that ntla was increased in 88% of PTBA treated embryos (n=60), as compared with controls (n=59) (FIGS. 10, E and F). This represented an 80% increase in ntla expression by qPCR analysis (FIGS. 10, E and F). The minimal effect on juxtaposed tissues coupled with an increase in the size of the notochord suggests that these cell types are not being converted to renal progenitor cells. Therefore, PTBA treatment cannot be definitively linked to a fate-transformation event.

Figure 11:
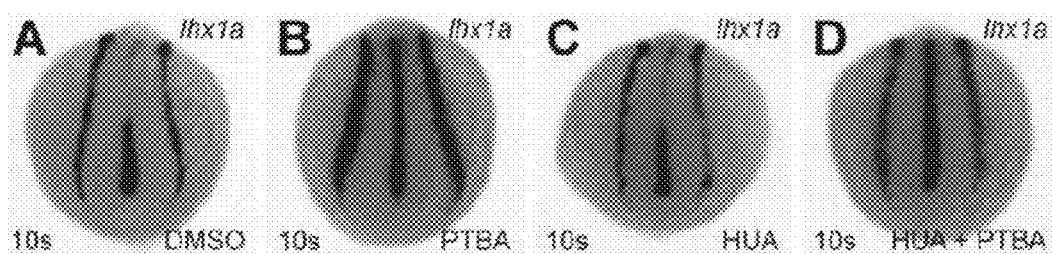
FIG. 11. PTBA requires proliferation for efficacy. (A through D) In situ hybridization for lhx1a expression in 10-somite embryos treated at 5 hpf with 0.5% DMSO (A and B) or HUA (C and D). At 8 hpf, treatment solutions were replaced with 0.5% DMSO (A), 3 µM PTBA (B), HUA (C), or 3 µM PTBA and HUA (D).

PTBA requires proliferation for efficacy: To examine the alternative possibility that PTBA-mediated renal progenitor cell expansion depends on cell proliferation, the efficacy of PTBA was tested in the presence of hydroxyurea and aphidicolin (HUA). HUA treatment has been previously shown to block cell division without affecting tissue specification (Harris, W. A. et al. Neuronal determination without cell division in *Xenopus* embryos. Neuron 6, 499-515, (1991)). As expected, 97% of PTBA-treated embryos (n=123) exhibited an expansion of lhx1a expression at 10 somites, as compared with controls (n=136), (FIGS. 11, A and B). HUA treatment alone did not affect lhx1a expression (FIG. 11C). However, treatment with both HUA and PTBA resulted in lhx1a expansion in only 13% of 10-somite embryos (n=104) (FIG. 11D). Furthermore, although lhx1a expression was decreased in the intermediate mesoderm, expression in the axial mesoderm still appeared to be increased in treated embryos (FIG. 11D). This result suggests that the PTBA-mediated lhx1a expansion in the axial region is proliferation independent. Since lhx1a expression in the axial mesoderm is gradually restricted to the tailbud during somitogenesis, the effect may reflect transcript perdurance.

Methods

Zebrafish Husbandry:

Zebrafish were maintained under standard conditions and staged as previously described (Kimmel, C. B., et al. Stages of embryonic development of the zebrafish. Dev Dyn 203, 253-310, (1995)). Embryos were collected from group matings of wild-type AB adults. All animal husbandry adhered to the National Institutes of Health Guide for the Care and Use of Laboratory Animals.

Small Molecule Screening:

The screen was performed in zebrafish embryos using the National Cancer Institute's Developmental Therapeutics Program (NCI/DTP) Diversity Set I. This library contains 1990 compounds selected by pharmacophore modeling to represent the more than 140,000 small molecules maintained in the NCI/DTP Open Repository. Compounds from the NCI/DTP Diversity Set I were diluted to 10 µM in E3 embryo medium (5 mM NaCl, 0.33 mM CaCl2, 0.33 mM MgSO4, and 0.17 mM KCl) in a final DMSO concentration of 0.5% and arrayed in 96-well plates. Beginning at approximately 2 hpf, embryos were transferred to each well in groups of five using a glass pipette. The plates were incubated at 28.5° C. for 70 hours. Individual wells were then scored for a dominant phenotype, representative of at least four of the five embryos. The primary objective was to identify compounds that caused edema in treated embryos at 72 hpf. Small molecules generating edema were retested once for verification, before obtaining additional compound from the NCI/DTP Open Repository.

Compound Sources and Treatments:

PTBA was synthesized as described below. Hydroxyurea and aphidicolin were obtained from Sigma-Aldrich. Groups of 20 to 30 chorionated 2 hpf embryos were arrayed in individual wells of 12-well plates. E3 medium was removed with a glass pipette and replaced with 1.5 ml treatment solutions containing 0.5% DMSO in E3 with or without compound at the reported concentrations. Treatments for all studies were initiated at 2 hpf, except for the temporal studies (FIG. 6) and the HUA studies (FIG. 11). HUA studies were performed as described previously (Zhang, L., et al. Cell cycle progression is required for zebrafish somite morphogenesis but not segmentation clock function. Development 135, 2065-2070, (2008)), with the following modifications. HUA in 0.5% DMSO was added at early gastrulation (5 hpf) and PTBA was subsequently added at late gastrulation (8 hpf) to allow for penetration of the proliferation inhibitors. All embryos were incubated at 28.5° C. until the required developmental stage.

Synthesis of PTBA:

Methyl 4-(phenylthio)butanoate (1) was prepared from thiophenol, potassium carbonate, and methyl 4-bromobutyrate in refluxing acetone as previously described (Minoru, U., et al. Substituted thiobutyric acid derivatives (assigned to Otsuka Pharmaceutical Co., Ltd., Japan). Jpn. Kokai Tokkyo Koho (1982), 9 pp. JP 57-058663(A) Publication date 1982 Apr. 8 Showa, see FIG. 12). 4-(phenylthio) butanoic acid (2) was prepared either in quantitative yield by saponification of 1 with aqueous KOH in MeOH overnight at room temperature followed by acidification with aqueous HCl, or in 97% yield from reaction of the sodium salt of thiophenol and γ-butyrolactone in refluxing EtOH and subsequent acidification with aqueous HCl as previously described (Traynelis, V. J., et al. Seven-membered heterocycles. I. Synthesis of benzo[b]thiepin 1,1-dioxide and 1-phenylsulfonyl-4-phenyl-1,3-butadiene. J Org Chem 26, 2728-2733, (1961)). All compounds gave $^1$H and $^{13}$C NMR (400/100 MHz and/or 600/150 MHz), mass spectra (GC-EI-MS, LC-ESI-MS, and high-resolution MALDI-TOF-MS), and melting points consistent with the literature and their structures. All spectral and melting point data suggested >99% purity.

Concentration-Response Studies:

Following 70 hours of treatment (as described above), edemic phenotypes in 72 hpf larvae were scored using a phenotype-based classification system. Wild type: no visible edema or developmental delay. Edemic 1: pericardial edema evident, may exhibit slight developmental delay, little or no axis curvature, axis length normal. Edemic 2: pericardial edema evident, slight to moderate developmental delay, axis curvature, axis length normal or slightly reduced. Edemic 3: pericardial edema evident, moderate to severe developmental delay, gross axis curvature frequently accompanied by tail kink, axis noticeably shortened. Significant effects (p<0.05) on survival were determined by two-tailed Fisher's exact test in comparison with the 0 µM PTBA treatment group.

In situ hybridization and immunocytochemistry: In situ hybridization was performed as previously described with some modifications.142 Hybridization temperature was 65° C. Embryos were blocked in 2% blocking reagent (Roche) with 5% sheep serum in MAB (100 mM maleic acid and 150 mM NaCl [pH 7.5]). Whole-mount immunocytochemistry with 1:25 mouse anti-α6F antibody (Developmental Studies Hybridoma Bank) and 1:100 Cy3 secondary antibody (Jackson ImmunoResearch) was performed as described previously.108 Embryos were embedded in JB-4 for sectioning per the manufacturer's instructions (Polysciences), sectioned at 5 µm, and mounted with Cytoseal 60 (Richard-Allan Scientific).

Relative qPCR.

Several of the genes analyzed by qPCR, including lhx1a and pax2a, show expression in anterior regions of the embryo as well as the IM. To focus more specifically on effects in the IM, cDNA samples taken from the trunks of treated and control embryos were examined. Samples for trunk RNA extraction were prepared by cutting embryos just above the first somite with microscissors and discarding the anterior portion. The trunk portions were homogenized with a plastic microcentrifuge pestle in 500 µL of TRI reagent (Ambion), and RNA was isolated using an RNeasy Micro Kit (QIAGEN) per the manufacturer's instructions. 1 µg RNA was heated to 75° C. for 5 min and then placed on ice. The following reagents were then added to a final volume of 29 µl: 1× Expand High-Fidelity PCR buffer without MgCl2 (Roche), 3 mM MgCl2, 500 µM dNTPs, 3.3 µM random hexamers, and 30 U Protector RNase Inhibitor (Roche). The mixture was preincubated to 42° C. for 5 min. 1 µl of 200 U/µl SuperScript II Reverse Transcriptase (RT) or RNase-free water was added for +RT or −RT reactions, respectively. Reactions were incubated at 42° C. for 1 hr and then stopped by heating to 95° C. for 5 min. Reaction products were stored at −20° C.

Primer sets were designed using NetPrimer and Beacon Designer (ver. 7.51) primer analysis software (PREMIER Biosoft). In each set, one primer was designed to span an exon boundary. In addition, at least one primer was confirmed to exhibit no significant cross-homology when compared against the NCBI zebrafish RefSeq mRNA library by BLAST search. Primer melting temperatures were maintained between 60° C. and 64° C. as determined by NetPrimer. Each primer set was observed to generate a single amplicon of expected length following qPCR. The reference gene primer sets have been previously described (Tang, R., Dodd, A., Lai, D., McNabb, W. C. & Love, D. R. Validation of zebrafish (Danio rerio) reference genes for quantitative real-time RT-PCR normalization. Acta Biochim Biophys Sin (Shanghai) 39, 384-390, (2007)) with one modification. The β-actin (F) sequence was changed to: CGTGCTGTCTTCCCATCCA (SEQ ID NO: 1). This corrects a one base discrepancy from the reported ENSDART accession number. The other primer sets included:

```
lhx1a (F):
                                        (SEQ ID NO: 2)
TTCATACTATGGAGATTATCAAAGCG, lhx1a (R):
                                        (SEQ ID NO: 3)
GGTCCTGATGAGGGAACAAAAG, pax2a (F):
                                        (SEQ ID NO: 4)
GTCCCTGGAAGCGACTTTTC, pax2a (R):
                                        (SEQ ID NO: 5)
TTGACTGGGCTGCGATGG, pax8 (F):
                                        (SEQ ID NO: 6)
GCTCCGCCGTCACTCCTC, pax8 (R):
                                        (SEQ ID NO: 7)
TCTCCTGGTCACTGTCATCGTG, ntla (F):
                                        (SEQ ID NO: 8)
CGCAGCACTACCACCAATAACTAC, ntla (R):
                                        (SEQ ID NO: 9)
GAGCCTGATGGGGTGAGAGTC, myod1 (F):
                                        (SEQ ID NO: 10)
TTCTGGAACATTACAGTGGAGACTC, myod1 (R):
                                        (SEQ ID NO: 11)
GTGCGTCAGCATTTGGTGTG, fli1a (F):
                                        (SEQ ID NO: 12)
CGGAAAAGGCTCTCCAACAG, fli1a (R):
                                        (SEQ ID NO: 13)
TGCTGGTGGGTCCTAATATCTG.
```

Relative qPCR was performed as described previously (Tang, R., et al. Acta Biochim Biophys Sin (Shanghai) 39, 384-390, (2007)) with some modifications. 25 µl reactions were prepared containing the following reagents: 12.5 µl 2×iQ SYBR Green Supermix (Bio-Rad), 5 µl 1 µM primer mix (1 µM each of forward and reverse primer), 5.5 µl RNase-free water, and 2 µl 1:10-diluted template (+RT or −RT product) or 2 µl RNase-free water (no template control). Each assay was performed in triplicate wells using an iQ5 Real-Time PCR Detection System (Bio-Rad). Thermal cycling was performed for 40 cycles, each consisting of 94° C. for 15 s, then 59° C. for 1 min. Following amplification, melt curve analysis was performed to assess non-specific amplification. Each primer set yielded a single peak, indicative of specific amplification. Reactions performed using −RT product or no template controls were observed to exhibit little or no amplification in comparison with their +RT counterparts.

Seven reference gene candidates [β-actin, β2 microglobulin, elongation factor 1 alpha, hypoxanthine guanine phosphoribosyl transferase 1, RNA polymerase subunit D, ribosomal protein L13a, and succinate dehydrogenase complex subunit A (SDHA)] (Tang, R., et al. Validation of zebrafish (Danio rerio) reference genes for quantitative real-time RT-PCR normalization. Acta Biochim Biophys Sin (Shanghai) 39, 384-390, (2007)) were screened to determine the gene(s) least affected by PTBA treatment. Relative qPCR experiments (n=3, 180 embryos) were performed using trunk cDNA obtained from 10-somite embryos treated from 2 hpf with either 0.5% DMSO or 3 µM PTBA. The results were analyzed using NormFinder software (ver. 0.953) to determine the most stable reference gene or combination of genes (Andersen, C. L., Jensen, J. L. & Orntoft, T. F. Normalization of real-time quantitative reverse transcription-PCR data: a model-based variance estimation approach to identify genes suited for normalization, applied to bladder and colon cancer data sets. Cancer Res 64, 5245-5250, (2004)). The combination of β-actin and SDHA was observed to exhibit the most stability, and was therefore used for normalization of all qPCR data.

Relative gene expression was calculated using iQ5 software (ver. 2.0, Bio-Rad) to determine normalized expression levels (ΔΔCt method). For comparison of fold-differences, the expression levels obtained from DMSO-treated controls were set to a value of 1.0. The amplification efficiency of each reaction was calculated using LinRegPCR software (ver. 11.4, Ruijter, J. M. et al. Amplification efficiency: linking baseline and bias in the analysis of quantitative PCR data. Nucleic Acids Res 37, e45, (2009)). The mean efficiencies of each tested primer set fell between 91% and 100%. Mean expression levels (normalized to the control group) and the corrected expression SD were used to generate 95% confidence intervals for each data set.

Cell Counting:

Tg(lhx1a:EGFP)$^{pt303}$ embryos were treated with 3 µM PTBA and then fixed in 4% paraformaldehyde in PBS for 8 hours at 4° C. Embryos were washed in PBS containing 0.1% TWEEN 20 (PBT) and incubated in 1 µg/ml DAPI in PBT for 30 minutes at room temperature. Embryos were flat-mounted on glass slides with Cytoseal 60 and imaged with either a Leica M205 FA epifluorescent microscope or an Olympus FluoView 1000 confocal microscope. Confocal projections contained stacks of six 3 µm images. A predefined box was positioned at the most posterior region of the notochord and included the most lateral GFP-positive cell in a kidney field. The cells that were positive for both GFP and DAPI within this box were counted manually with the aid of ImageJ. Variances of the control and PTBA-treated groups were compared by F test and found to be unequal. Therefore, a two-tailed t test with unequal variance was used to determine significance ($\alpha$=0.05).

Example 2—Mechanism of TBA Efficacy

Having established that PTBA stimulates renal progenitor cell proliferation, the mechanism responsible for this effect was then determined. Initial structure-activity relationship experiments demonstrated that certain structural motifs within PTBA modify its efficacy. While these results provided important leads for future analog development, they did not reveal any clues to the underlying mechanism. The breakthrough came when subsequent analysis revealed that PTBA is structurally similar to known histone deacetylase inhibitors (HDACis), including 4-phenylbutanoic acid (PBA) and trichostatin A (TSA). HDACis are thought to attenuate retinoic acid receptor-mediated inhibition of target genes, lowering the threshold of retinoic acid (RA) required to activate transcription. Since RA affects pronephric development, it was hypothesized that PTBA functions as an HDACi and its effects are mediated through the RA pathway.

Results

Figure 13:
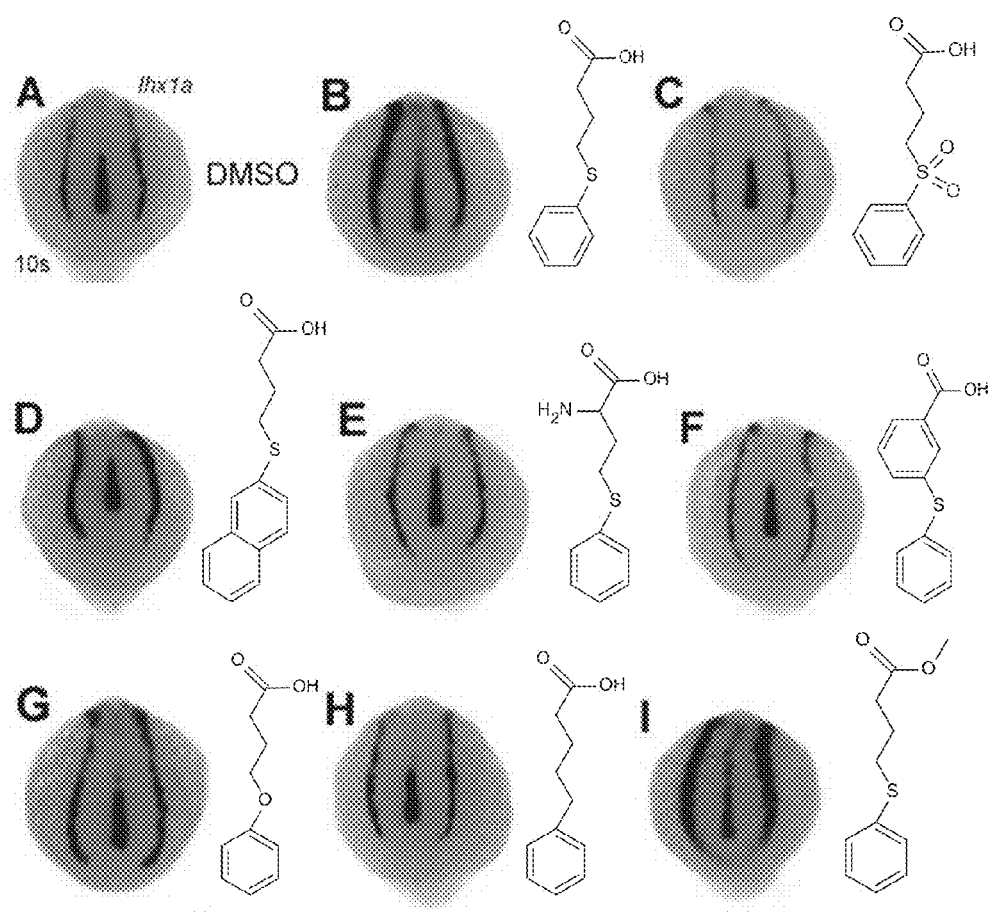
FIG. 13. Structure-activity relationship studies reveal essential moieties for PTBA efficacy. (A through I) In situ hybridization for lhx1a expression in 10-somite embryos treated with 0.5% DMSO (A) or 3 µM of the following compounds: PTBA (B), 4-(phenylsulfonyl)butanoic acid (PSOBA) (C), 4-(naphthalen-2-ylthio)butanoic acid (D), 2-amino-PTBA (E), 3-(phenylthio)benzoic acid (F), 4-phenoxybutanoic acid (G), 5-phenylpentanoic acid (H), and methyl-4-(phenylthio)butanoate (I).

PTBA Structure-Activity Studies Reveal Critical Motifs:

Structure-activity analyses was performed using a series of seven analogs (FIG. 13). In situ hybridization for lhx1a was performed on 10-somite embryos treated with each analog at 3 µM. The results were compared with control (no expansion, n=53) (FIG. 13A) and PTBA-treated embryos (100% expansion, n=52) (FIG. 13B). Replacement of the phenylthio ether with a phenylsulfonyl linkage stripped the compound of its effects on renal progenitor cells (no expansion, n=54) (FIG. 13C). Therefore, the oxidation state of the sulfur atom is an activity determinant. However, 4-(naphthalen-2-yl thio)butanoic acid, an analog carrying a naphthalene ring in place of the phenyl moiety of PTBA, still expands lhx1a expression to some extent (33% expansion, n=39) (FIG. 13D). Thus, modifications of the ring structure are tolerated and suggest a site for future analog development. Two analogs containing substitutions of the butanoic acid backbone, 2-amino-PTBA and 3-(phenylthio)benzoic acid had no effect on lhx1a expression (no expansion, n=64 and n=53, respectively) (FIGS. 13, E and F), suggesting a requirement for a flexible hydrocarbon backbone for biological activity. 4-phenoxybutanoic acid and 5-phenylpentanoic acid, which contain oxygen and carbon substitutions for the sulfur atom, respectively were examined. 4-Phenoxybutanoic acid exhibited reduced activity compared with the parent compound (13% expansion, n=56) (FIG. 13G), while 5-phenylpentanoic acid was inactive (no expansion, n=55) (FIG. 13H). These results suggest that compound efficacy is improved when an atom with a nonbonding electron pair(s) occupies this position. Finally, the esterified analog methyl-4-(phenylthio)butanoate exhibited equal potency to PTBA (100% expansion, n=41) (FIG. 13I).

Figure 14:
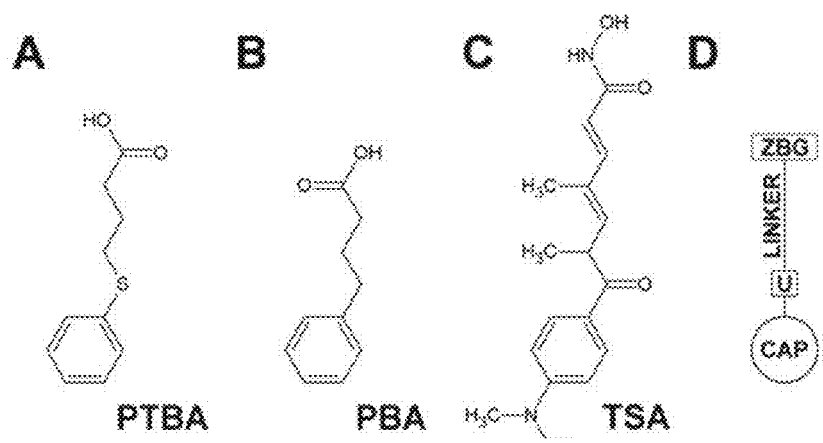
FIG. 14. PTBA exhibits structural similarity to HDACis. (A through D) Structures of PTBA (A), PBA (B), TSA (C), and the general HDACi pharmacophore (D) containing a cap (CAP), connecting unit (U), hydrophobic linker (LINKER), and zinc-binding group (ZBG).

HDACis Mimic the Effects of PTBA:

Subsequent structural analysis revealed that PTBA is a close analog of 4-phenylbutanoic acid (PBA), a known HDACi (FIGS. 14, A and B), and that both compounds exhibit some similarity to the HDACi trichostatin A (TSA) (FIG. 14C). Indeed, all three structures contain the elements of the HDACi pharmacophore, a general representation of the functional domains within this class of compounds (FIG. 14D). These include an aliphatic or aromatic cap, connecting unit, hydrophobic linker, and zinc-binding group.

Figure 15:
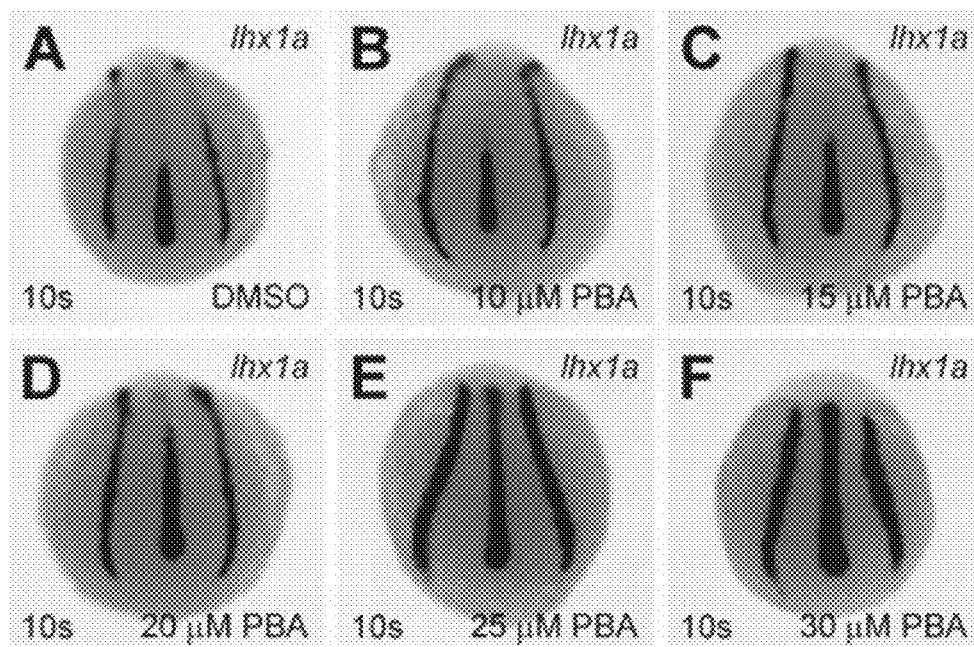
FIG. 15. Treatment with the HDACi PBA expands the kidney field. (A through F) In situ hybridization for lhx1a in 10-somite embryos treated from 2 hpf with: 0.5% DMSO (A, n=59), 10 µM PBA (B, n=58), 15 µM PBA (C, n=60), 20 µM PBA (D, n=59), 25 µM PBA (E, n=58), or 30 µM PBA (F, n=53).
Figure 16:
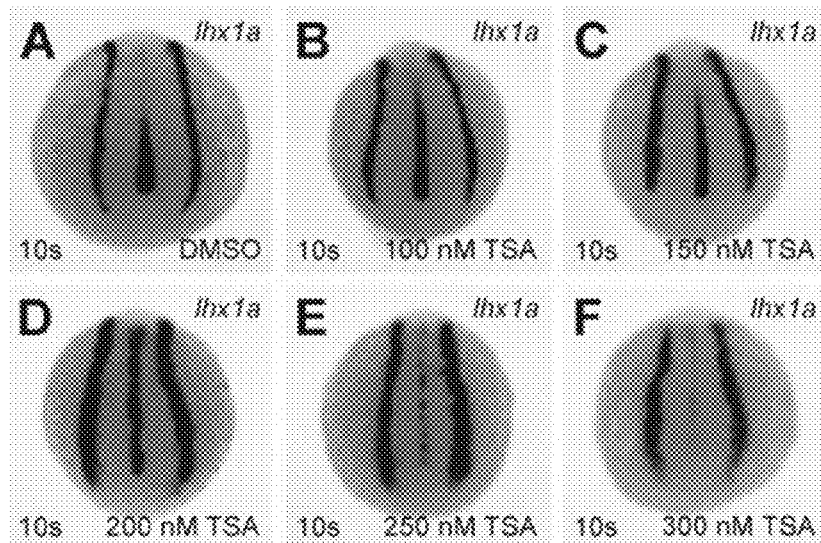
FIG. 16. Treatment with the HDACi TSA expands the kidney field. (A through F) In situ hybridization for lhx1a in 10-somite embryos treated from 2 hpf with: 0.5% DMSO (A, n=60), 100 nM TSA (B, n=57), 150 nM TSA (C, n=57), 200 nM TSA (D, n=52), 250 nM TSA (E, n=42), or 300 nM TSA (F, n=40).

Because PBA and TSA are structurally analogous to PTBA, it was determined whether they shared the same ability to expand renal progenitor cells. Concentration-response experiments were performed to determine the concentrations of PBA or TSA necessary to elicit lhx1a expansion, if any (FIGS. 15 and 16).

It was determined that treatment with 25 µM PBA or 200 nM TSA produced an expansion of lhx1a expression consistent with that elicited by 3 µM PTBA (FIGS. 15E and 16D compared with FIG. 4B). Therefore, at least two known HDACis mimic the effects of PTBA, supporting the idea that PTBA likewise functions as an HDACi.

Figure 17:
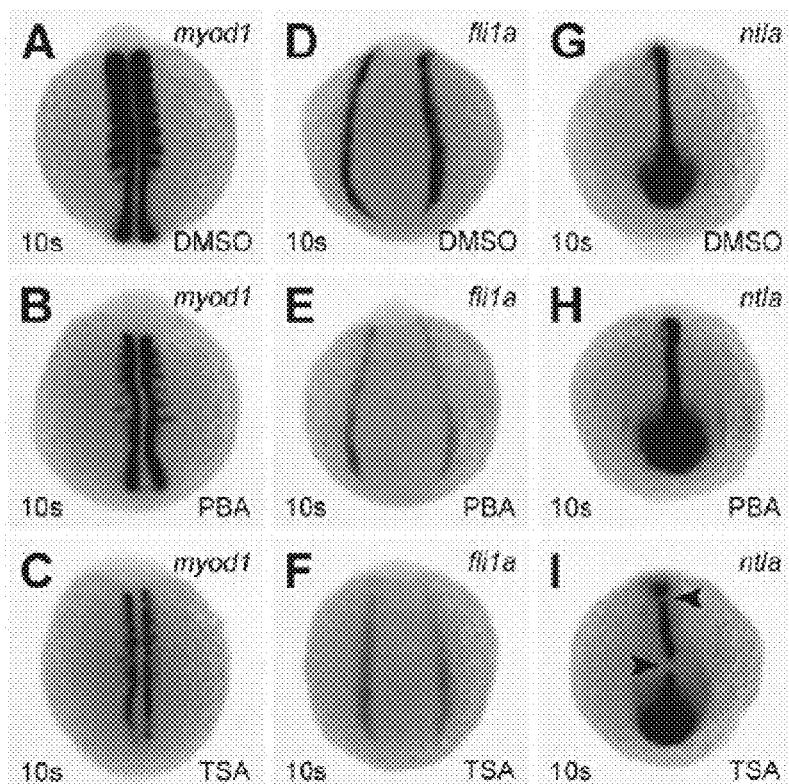
FIG. 17. Treatment with PBA or TSA affects nearby tissues. (A through I) In situ hybridization for myod1 (A through C), fli1a (D through F), or ntla (G through I) in 10-somite embryos treated with 0.5% DMSO (A, D, and G), 25 µM PBA (B, E, and H), or 200 nM TSA (C, F, and I). Arrowheads indicate breaks in ntla expression.

PBA and TSA Exhibit Greater Toxicity than PTBA:

How trunk mesoderm juxtaposed to the kidney field is affected by PBA and TSA treatments was then examined. PTBA treatment does not significantly affect the expression of somitic or vascular markers (FIG. 10, A through D) Furthermore, although PTBA increased ntla expression, the general structure of the notochord remained relatively unchanged (FIGS. 10, E and F). However, TSA is a broad-spectrum HDACi that causes disruption of multiple tissues in zebrafish and demonstrates renal toxicity in cell culture. Therefore, embryos were treated with 25 µM PBA or 200 nM TSA and the expression of myod1, fli1a, and ntla was compared with that of control embryos. Expression of myod1 was decreased in 57% of PBA-treated embryos (n=53) and 100% of TSA-treated embryos, as compared to controls (n=54) (FIG. 17, A through C). Furthermore, TSA treatment caused an almost complete loss of the somitic blocks (FIG. 17C). As compared with controls (n=54), fli1a expression decreased in 78% of PBA-treated embryos (n=54) and 95% of TSA-treated embryos (n=55) (FIG. 17, D through F). PBA increased ntla expression in 87% of treated embryos (n=52), as compared to controls (n=55) (FIGS. 17, G and H). This effect appears similar to the expanded ntla expression observed following PTBA treatment (FIG. 10F). In contrast, TSA disrupted normal ntla expression in 86% of treated embryos (n=56), as compared with controls (FIGS. 17, G and I). This resulted in breaks in the ntla expression pattern (FIG. 17I, arrowheads).

Figure 18:
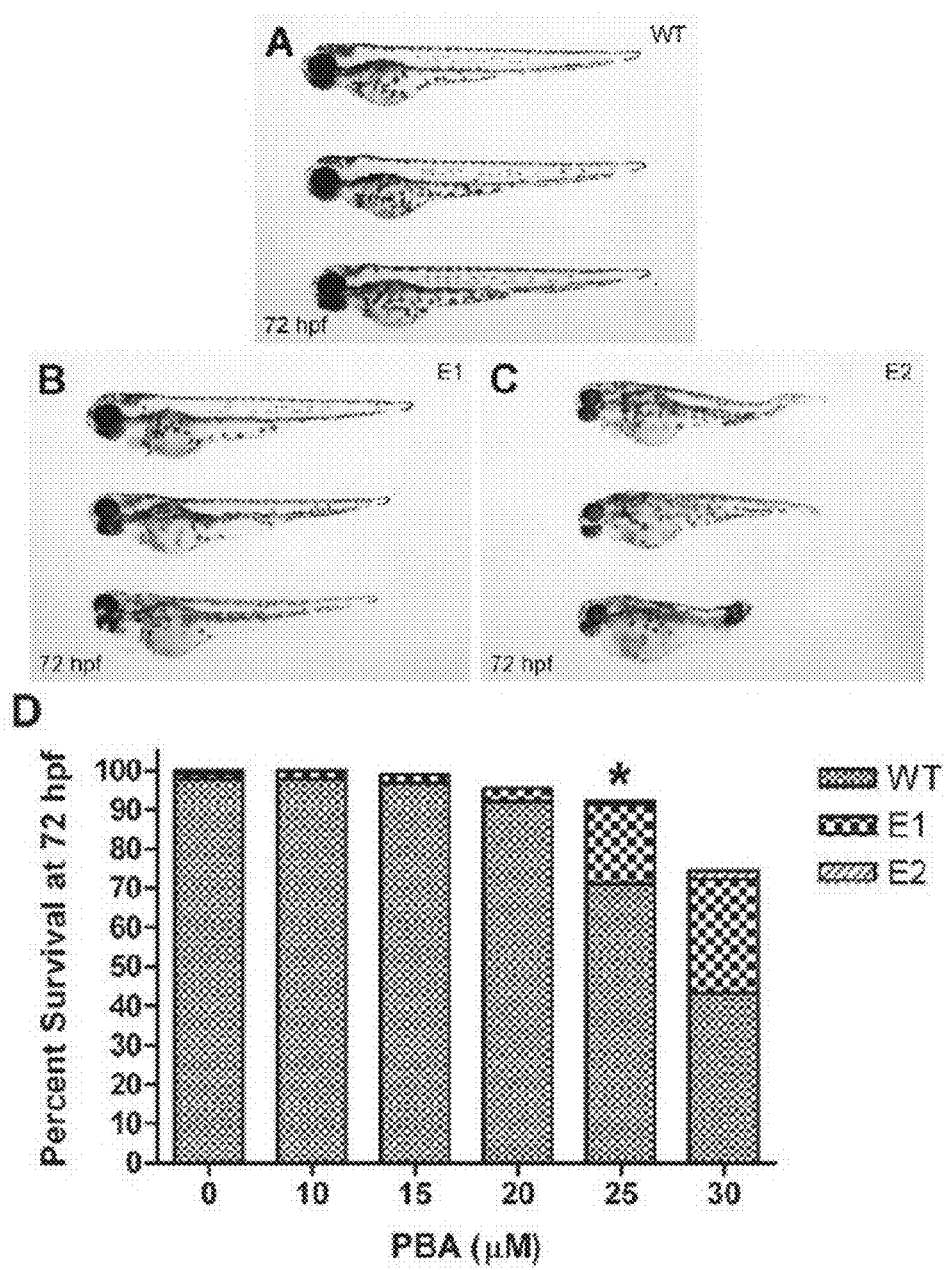
FIG. 18. PBA elicits concentration-dependent effects on larval edema and survival. (A through D) Embryos were treated with 0 to 30 µM PBA from 2 hpf, and larvae were scored at 72 hpf using a phenotype-based classification system described herein. (A) Wildtype (WT). (B) Edemic 1 (E1). (C) Edemic 2 (E2). (D) Graph of phenotypes after treatment with 0 to 30 µM PBA (n=90 per concentration). Asterisk denotes lowest PBA concentration that exhibits a significant effect (p<0.05) on survival.
Figure 19:
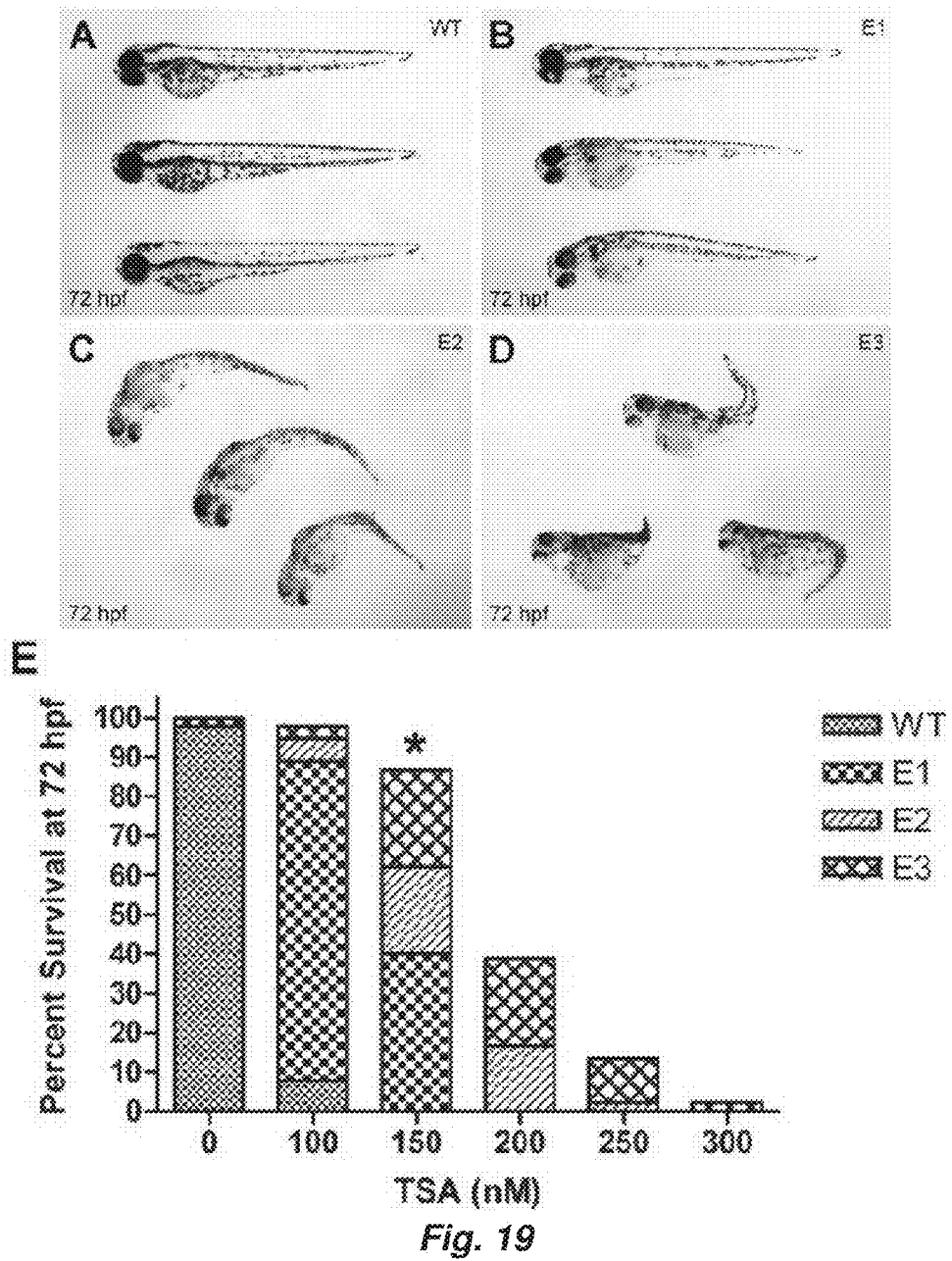
FIG. 19. TSA elicits concentration-dependent effects on larval edema and survival. (A through D) Embryos were treated with 0 to 300 nM TSA from 2 hpf, and larvae were scored at 72 hpf using a phenotype-based classification system described herein. (A) Wildtype (WT). (B) Edemic 1 (E1). (C) Edemic 2 (E2). (D) Edemic 3 (E3). (E) Graph of phenotypes after treatment with 0 to 300 nM PBA (n=90 per concentration). Asterisk denotes lowest TSA concentration that exhibits a significant effect (p<0.05) on survival.

To determine the toxicity of PBA and TSA relative to PTBA, phenotypic concentration-response experiments were again performed. 72 hpf larvae were assessed for the development of edemic phenotypes over the same concentration range used to test for expansion of the kidney field. Pericardial edema was evident in 23% of larvae treated with 25 µM PBA (n=83) and 100% of larvae treated with 200 nM TSA (n=35) (FIGS. 18 and 19). In addition, 25 µM PBA caused minimal, but significant death (8%, n=90), while treatment with 200 nM TSA resulted in high lethality (61%, n=90) (FIGS. 18 and 19).

Figure 20:
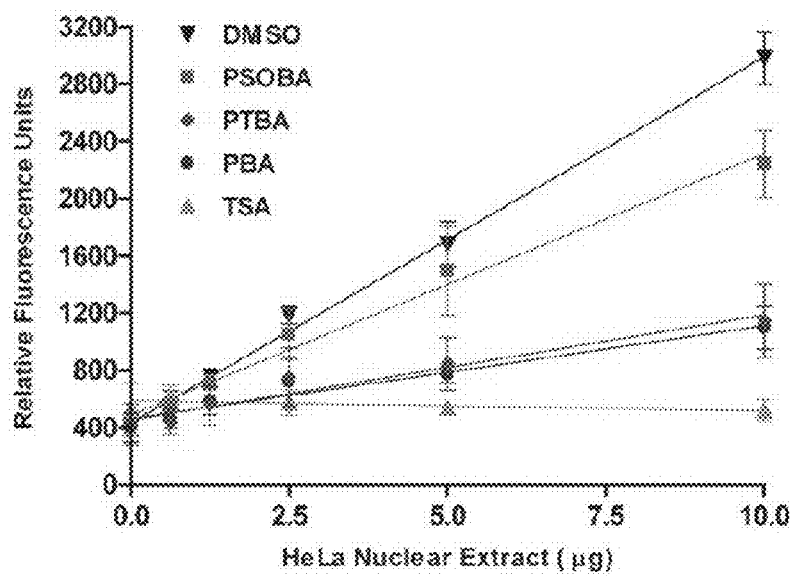
FIG. 20. PTBA functions as an HDACi in vitro. Fluorescence histone deacetylation assay performed in the presence of 5 mM PTBA, 5 mM PBA, 5 mM PSOBA, 1 µM TSA, or 5% DMSO. At a given amount of nuclear extract, less fluorescence indicates less HDAC activity. Error bars represent the 95% confidence intervals for each data point.

PTBA Functions as an HDACi In Vitro:

Because PBA and TSA mimic the ability of PTBA to expand renal progenitor cells, it was determined whether PTBA functions as an HDACi. To evaluate this in vitro, the deacetylation of a fluorescent peptide substrate was measured in the presence of human HDACs. HDAC activity increased in direct proportion to the amount of HeLa cell nuclear extract added to the assay (FIG. 20, black triangle). Addition of TSA completely blocked activity at all input levels of nuclear extract (FIG. 20, gray triangle). Previous work showed that 5 mM PBA decreased HDAC activity in DSI9 mouse erythroleukemia cells to 19% of the control value (Lea, M. A. & Tulsyan, N. Discordant effects of butyrate analogues on erythroleukemia cell proliferation, differentiation and histone deacetylase. Anticancer Res 15, 879-883, (1995)). To determine whether PTBA inhibited HDACs to a similar extent as PBA, both compounds were evaluated at 5 mM. PTBA and PBA showed similar potency, reducing the HDAC activity elicited by 10 µg HeLa extract to 30% of the control value (FIG. 20, diamond and circle, respectively). Previously, the PTBA analog, 4-(phenylsulfonyl)butanoic acid (PSOBA), demonstrated no ability to expand renal progenitor cells (FIG. 13C). Therefore, it was hypothesized that it would function poorly in vitro as an HDACi. As expected, 5 mM PSOBA decreased the HDAC activity elicited by 10 µg HeLa extract to only 70% of the control value (FIG. 20, square).

Figure 21:
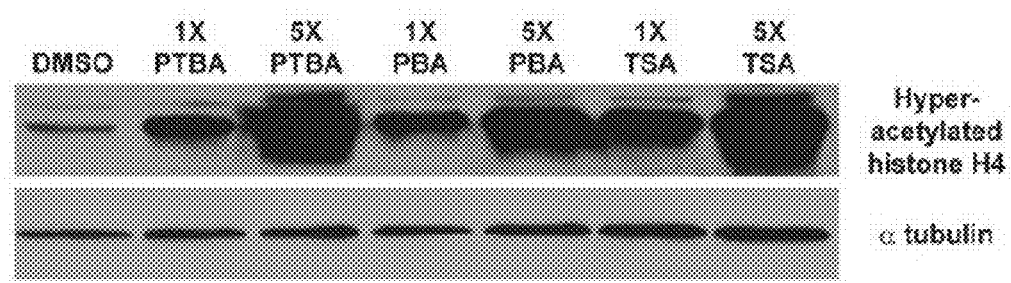
FIG. 21. PTBA functions as an HDACi in vivo. Western blot examining the acetylation state of histone H4 isolated from embryos at 30 hpf that had been treated for 6 hours with 0.5% DMSO, 3 µM (1×) or 15 µM (5×) PTBA, 25 µM (1×) or 125 µM (5×) PBA, and 200 nM (1×) or 1 µM (5×) TSA. Western blot for α-tubulin demonstrates equal loading.

PTBA Functions as an HDACi In Vivo:

It was next determined whether the HDACi function of PTBA was quantifiable in vivo. 24 hpf embryos were treated with 3 µM PTBA, 25 µM PBA, or 200 nM TSA for 6 hours. Protein extracts were prepared and immunoblotted with an anti-hyperacetylated histone H4 antibody. Histone H4 hyperacetylation was observed following treatment with all three compounds at their tested concentrations, as compared with the control (FIG. 21). Furthermore, increasing the compound concentration caused a corresponding increase in hyperacetylation (FIG. 21). Therefore, both in vitro and in vivo results confirm that PTBA functions as an HDACi.

Figure 22:
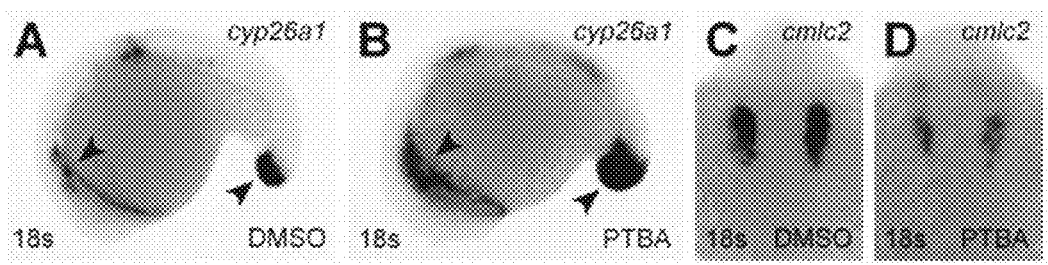
FIG. 22. PTBA affects the expression of RA-responsive genes. (A through D) In situ hybridization for cyp26a1 (A and B) and cmlc2 (C and D) in 18-somite embryos treated with 0.5% DMSO (A and C) or 3 µM PTBA (B and D). Arrowheads highlight cyp26a1 expression domains.

PTBA Affects Retinoic Acid Signaling:

HDACis are believed to lower the threshold of RA necessary to activate transcription. If PTBA treatment facilitates activation of the RA pathway, then expression of genes responsive to RA signaling should change. Consequently, two genes were focused on: cyp26a1, which is directly activated by RA signaling, and the cardiac gene cmlc2, whose expression in the heart field size is reduced by RA treatments. In a previous study, cmlc2 expression was assessed for RAdependent effects in 18-somite embryos (Keegan, B. R., Feldman, J. L., Begemann, G., Ingham, P. W. & Yelon, D. Retinoic acid signaling restricts the cardiac progenitor pool. Science 307, 247-249, (2005)), therefore embryos were collected at the 18-somite stage for continuity. As compared to controls (n=58), expression of cyp26a1 was increased in 100% of PTBA-treated embryos (n=57) (FIGS. 22, A and B). In agreement with this result, cmlc2 expression was decreased in 100% of PTBA-treated embryos (n=58), as compared to controls (n=57) (FIGS. 22, C and D).

Figure 23:
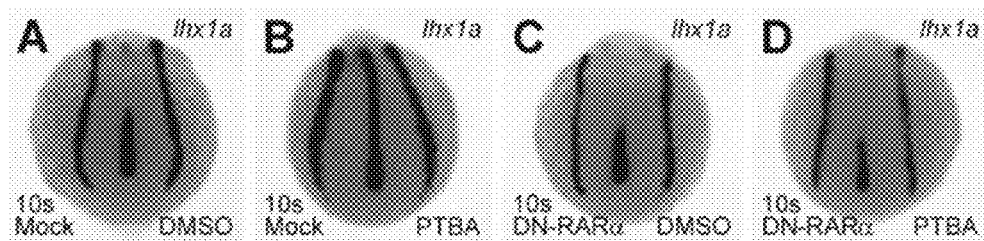
FIG. 23. RA signaling mediates PTBA efficacy. (A through D) In situ hybridization in 10-somite embryos mock-injected with 1% fluorescein dextran (A and B) or injected with 200 pg of DN-RARα mRNA and 1% fluorescein dextran (C and D). At 5 hpf, embryos were treated with 0.5% DMSO (A and C) or 3 µM PTBA (B and D).

To provide a stronger link between PTBA treatment and RA signaling, mRNA encoding a dominant-negative RARα construct (DN-RARα), which is known to block RA signaling (Blumberg, B. et al. An essential role for retinoid signaling in anteroposterior neural patterning. Development 124, 373-379, (1997)), was injected prior to PTBA treatment. In situ hybridization was performed to determine the maximum amount of DN-RARα mRNA that could be injected at the one-cell stage without affecting lhx1a expression. In the tested range of 0 to 400 ng, embryos injected with 200 ng DNRARα mRNA or less showed normal lhx1a expression, while higher doses caused aberrant or decreased expression (data not shown). Therefore, 200 ng DN-RARα mRNA was injected to assess the relationship between PTBA and the RA pathway. As compared with controls (n=80), an expansion of lhx1a expression was observed in 90% of the mock-injected PTBA-treated embryos at the 10-somite stage (n=78) (FIGS. 23, A and B). Expression of lhx1a appeared normal in 92% of embryos injected with 200 pg DN-RARα mRNA (n=125) (FIG. 23C). However, only 19% of the embryos injected with 200 pg DN-RARα mRNA and subsequently treated with PTBA showed expanded lhx1a expression (n=125) (FIG. 23D). Therefore, these data suggest that PTBA-mediated expansion of renal progenitor cells is dependent on the retinoic acid pathway.

Methods

Zebrafish husbandry and in situ hybridization were performed as described above.

Compound Sources and Treatments:

PTBA and methyl-4-(phenylthio)butanoate were synthesized as described above. 4-(Naphthalen-2-ylthio)butanoic acid (NSC2733), 3-(phenylthio)benzoic acid (NSC113994), and 2-amino-PTBA (NSC140113) were obtained from the NCI/DTP Open Repository. PBA, TSA, 4-phenoxybutanoic acid, and 5-phenylpentanoic acid were obtained from Sigma-Aldrich. PSOBA was obtained from Matrix Scientific. Treatments were performed as described above, except for the in vivo hyperacetylation assays and DN-RARα experiments (see below).

Histone Hyperacetylation Assays:

SDS-PAGE and Western blotting were performed as described previously with some modifications (Noel, E. S. et al. Organ-specific requirements for Hdac1 in liver and pancreas formation. Dev Biol 322, 237-250, (2008)). Proteins were separated on 18% SDS-PAGE gels. Membranes were incubated at 4° C. overnight with 1:1000 anti-hyperacetylated histone H4 antibody (06-946, Millipore) or 1:1000 anti-α-tubulin antibody (Sigma-Aldrich) in PBT containing 5% nonfat milk.

Fluorescence HDAC Assays:

In vitro HDAC activity assays were performed using a fluorescence HDAC assay kit (Active Motif) according to the manufacturer's instructions. For maintaining compound solubility at 5 mM, the final DMSO concentration in all assay wells was increased to 5%. Fluorescence was detected using an M5 Plate Reader (Molecular Dynamics)

mRNA Synthesis and Microinjections:

Synthetic mRNA was generated from the XRARα1$^{405}$/pCD61 construct (Blumberg, B. et al. An essential role for retinoid signaling in anteroposterior neural patterning. Development 124, 373-379, (1997), NotI digested) using a T7 mMessage mMachine kit (Ambion). Zebrafish embryos were injected at the one-cell stage either with 200 pg of synthetic mRNA and 1% fluorescein dextran (Sigma-Aldrich) or with 1% fluorescein dextran alone (mock) and allowed to develop in E3 culture medium at 28.5° C. At the 256-cell stage, only fluorescein-dextran positive embryos were selected for PTBA treatment, which occurred at 5 hpf.

Example 3—Development of PTBA Analogs

Determining that treating zebrafish embryos with PTBA, a novel HDACi, increased the number of renal progenitor cells leading to a corresponding increase in pronephric size suggested that these cells are capable of contributing to nephrogenesis. As early as 1989, Bacallo and Fine proposed that kidney regeneration follows the same pattern of differentiation events that lead to nephrogenesis (Molecular events in the organization of renal tubular epithelium: from nephrogenesis to regeneration. Am J Physiol 257, F913-924, (1989)). Both processes begin with the proliferation of renal progenitor cells to provide the raw material necessary for subsequent differentiation into kidney tissue. Since PTBA stimulates renal progenitor cell proliferation during pronephric development, it may function similarly during kidney regeneration. However, developing PTBA into a potential therapeutic requires the consideration of both its efficacy and toxicity. Furthermore, expanding the structure-activity relationship study to a wider selection of small molecules may yield better candidates for future in vivo studies. Therefore, a panel of structural and functional analogs of PTBA was evaluated to identify compounds exhibiting nanomolar efficacy and low toxicity in kidney cell culture. It was hypothesized that modifying the key structural elements that determine the HDACi activity of PTBA would improve its ability to expand renal progenitor cells.

Results

Figure 24:
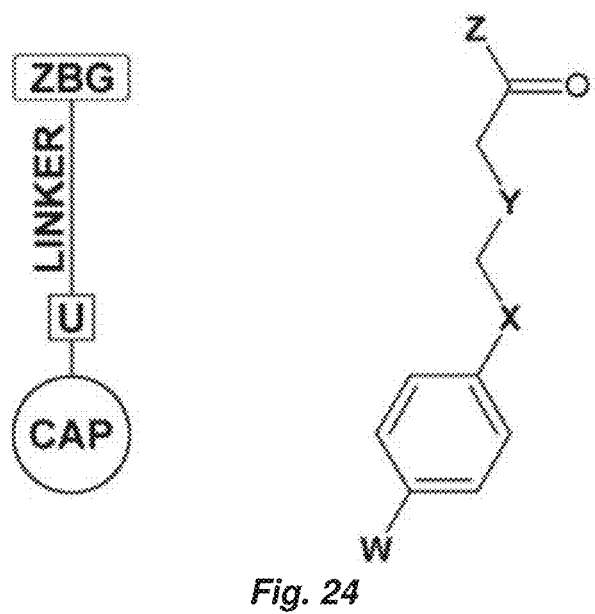
FIG. 24 General structure of a PTBA analog containing functional group substitutions as described in Table 2.

Phenotypic Screening of PTBA Analogs:

As shown above, treating zebrafish embryos with 3 µM PTBA generates pericardial edema by 72 hpf (FIG. 3). This PTBA concentration also stimulates the proliferation of renal progenitor cells during pronephric development (FIGS. 5 and 11). Furthermore, by 48 hpf, embryos treated with 3 µM PTBA exhibit wider pronephric tubules and a failure of wt1a convergence at the dorsal midline (FIGS. 7, 8, and 9) Therefore, it is reasonable to hypothesize that the edemic phenotype reflects aberrant kidney morphogenesis resulting from an overabundance of renal progenitor cells. Consequently, a phenotypic screen was performed on a panel of PTBA analogs at 3 µM to identify potentially effective compounds. Each of the compounds chosen for analysis represents either a structural or functional analog of the lead compound, PTBA. The structural analogs contain functional group additions or substitutions in one of four elements of the PTBA structure. These modify the key determinants of HDACi activity as predicted by the general pharmacophore: the aliphatic cap, connecting unit, hydrophobic linker, and zinc-binding group (FIGS. 14D and 24). The structural analogs selected for the panel each contain one or more of these modifications (Table 2). Several functional group choices were based on previous structure-activity relationship studies of PTBA. For example, methylating the zinc-binding group of PTBA generated a compound equally capable of expanding lhx1a expression in treated embryos (FIG. 13I). Therefore, the efficacy of several alkylated analogs was assessed.

TABLE 2

Structural analogs of PTBA (See, FIG. 24).

| Compound Name | Aliphatic Cap (W) | Connecting Unit (X) | Fatty Acid Linker (V) | Zinc-Binding Group (Z) |
|---|---|---|---|---|
| 4-(phenylthio)butanoic acid (PTBA) | H | S | $CH_2$ | OH |
| 4-(naphthalen-2-ylthio)butanoic acid | $C_6H_6$ | S | $CH_2$ | OH |
| 4-(phenylsulfonyl)butanoic acid | H | $SO_2$ | $CH_2$ | OH |
| 4-phenoxybutanoic acid | H | O | $CH_2$ | OH |
| 4-(phenylamino)butanoic acid | H | NH | $CH_2$ | OH |
| 5-phenylpentanoic acid | H | $CH_2$ | $CH_2$ | OH |
| 3-(phenylthio)benzoic acid | H | S | $C_6H_6$ | OH |
| methyl 4-(phenylthio)butanoate | H | S | $CH_2$ | $OCH_3$ |
| propyl 4-(phenylthio)butanoate | H | S | $CH_2$ | $O(CH_2)_2CH_3$ |
| butan-2-yl 4-(phenylthio)butanoate | H | S | $CH_2$ | $OCH(CH_3)CH_2CH_2$ |
| tert-butyl 4-(phenylthio)butanoate | H | S | $CH_2$ | $OC(CH_3)_3$ |
| N-hydroxy-4-(phenylthio)butanamide | H | S | $CH_2$ | NHOH |
| methyl 4-[(4-methylphenyl)thio]butanoate | $CH_3$ | S | $CH_2$ | $OCH_3$ |
| methyl 4-[(4-methoxyphenyl)thio]butanoate | $OCH_3$ | S | $CH_2$ | $OCH_3$ |
| methyl 4-[(4-fluorophenyl)thio]butanoate | F | S | $CH_2$ | $OCH_3$ |
| methyl 4-[(4-chlorophenyl)thio]butanoate | Cl | S | $CH_2$ | $OCH_3$ |
| methyl 4-[(4-bromophenyl)thio]butanoate | Br | S | $CH_2$ | $OCH_3$ |
| N-hydroxy-4-[(4-methylphenyl)thio]butanamide | $CH_3$ | S | $CH_2$ | NHOH |
| N-hydroxy-4-[(4-methoxyphenyl)thio]butanamide | $OCH_3$ | S | $CH_2$ | NHOH |
| 4-[(4-fluorophenyl)thio]-N-hydroxybutanamide | F | S | $CH_2$ | NHOH |
| 4-[(4-chlorophenyl)thio]-N-hydroxybutanamide | Cl | S | $CH_2$ | NHOH |
| 4-[(4-bromophenyl)thio]-N-hydroxybutanamide | Br | S | $CH_2$ | NHOH |

Figure 25:
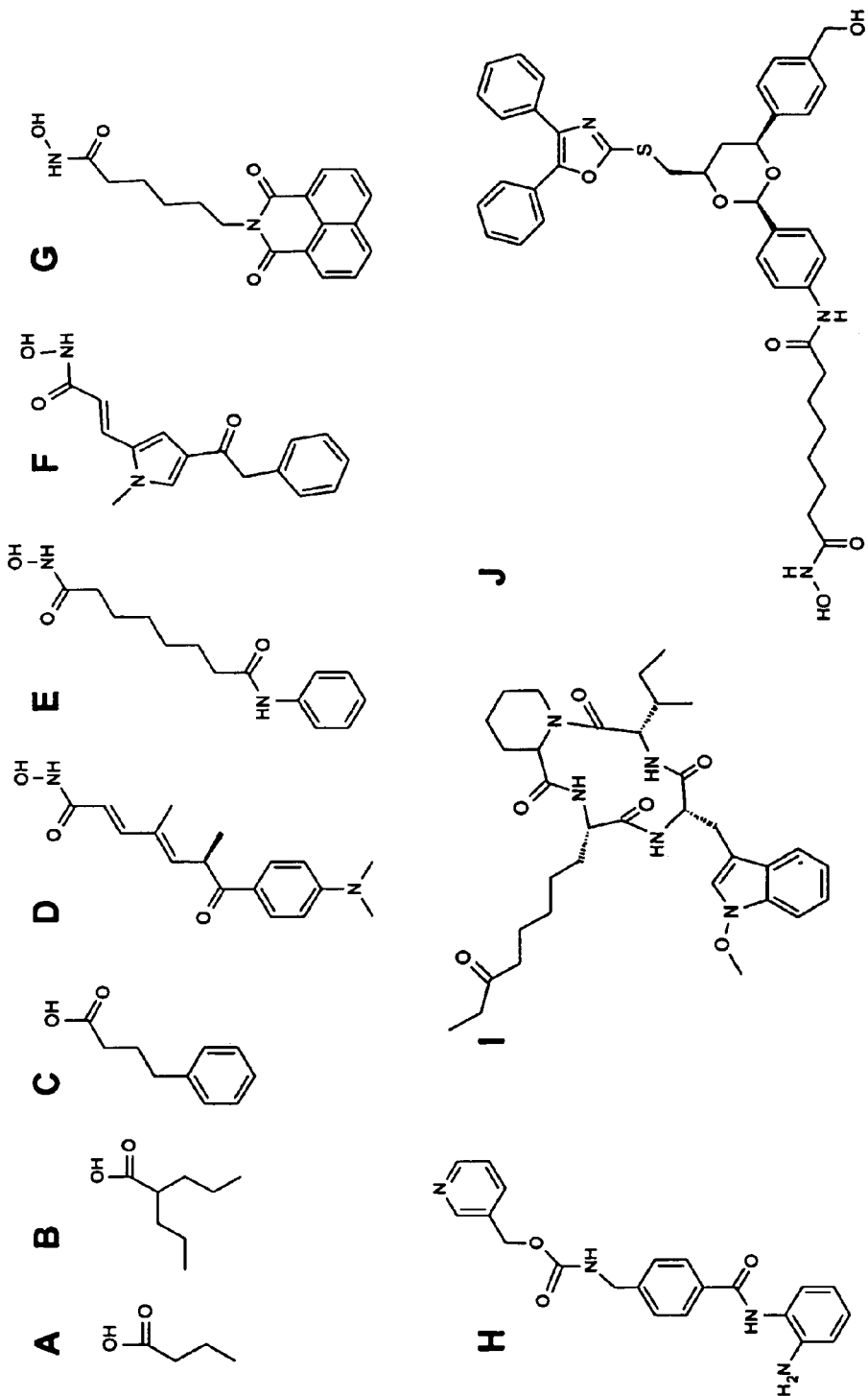
FIG. 25. Functional analogs of PTBA. (A through J) Structures of the HDACis butanoic acid (A), valproic acid (B), 4-phenylbutanoic acid (PBA, C), trichostatin A (TSA, D), SAHA (E), APHA compound 8 (F), Scriptaid (G), MS-275 (H), apicidin (I), and tubacin (J).

In addition, it was observed that the hydroxamic acid HDACi, trichostatin A (TSA), exhibited high efficacy, increasing lhx1a expression at 200 nM. (FIG. 16D). Hydroxamic acids, which form two coordinate bonds with the active site zinc, are generally stronger than carboxylic acids, including PTBA, which form only one (Jacobsen, F. E., Lewis, J. A. & Cohen, S. M. The design of inhibitors for medicinally relevant metalloproteins. ChemMedChem 2, 152-171, (2007)). Thus, several of the analogs tested contained hydroxamate moieties on the zinc-binding group. Ten functional analogs were also chosen to represent a subset of known HDACis of several different classes (FIG. 25). These include inhibitors derived from carboxylic acids, hydroxamic acids, benzamides, and natural products (Villar-Garea, A. & Esteller, M. Histone deacetylase inhibitors: understanding a new wave of anticancer agents. Int J Cancer 112, 171-178, (2004)). With the exception of butanoic acid, all of the chosen compounds have predicted octanol-water partition coefficients (Log Ps) greater than 1 (Table 3).

TABLE 3

Predicted octanol-water partition coefficients (XLogPs) of the PTBA analogs. XLogP values were calculated from the chemical structures using XLOGP3 (ver. 3.2.2), a web-based application.

| Compound Name | XLogP |
|---|---|
| butanoic acid | 0.79 |
| 4-(phenylsulfonyl)butanoic acid | 1.01 |
| 4-(phenylamino)butanoic acid | 1.41 |
| N-hydroxy-4-[(4-methoxyphenyl)thio]butanamide | 1.52 |
| APHA compound 8 | 1.52 |
| N-hydroxy-4-(phenylthio)butanamide | 1.55 |
| 4-[(4-fluorophenyl)thio]-N-hydroxybutanamide | 1.65 |
| SAHA | 1.86 |
| N-hydroxy-4-[(4-methylphenyl)thio]butanamide | 1.91 |
| MS-275 | 2.02 |
| 4-phenoxybutanoic acid | 2.14 |
| 4-[(4-chlorophenyl)thio]-N-hydroxybutanamide | 2.18 |
| Scriptaid | 2.18 |
| 4-[(4-bromophenyl)thio]-N-hydroxybutanamide | 2.24 |
| 4-(phenylthio)butanoic acid (PTBA) | 2.29 |
| 4-phenylbutanoic acid (PBA) | 2.42 |
| methyl 4-[(4-methoxyphenyl)thio]butanoate | 2.59 |
| methyl 4-(phenylthio)butanoate | 2.61 |
| 5-phenylpentanoic acid | 2.70 |
| methyl 4-[(4-fluorophenyl)thio]butanoate | 2.71 |
| valproic acid | 2.75 |
| trichostatin A (TSA) | 2.75 |
| methyl 4-[(4-methylphenyl)thio]butanoate | 2.98 |
| methyl 4-[(4-chlorophenyl)thio]butanoate | 3.24 |
| methyl 4-[(4-bromophenyl)thio]butanoate | 3.31 |
| propyl 4-(phenylthio)butanoate | 3.51 |
| 4-(naphthalen-2-ylthio)butanoic acid | 3.54 |
| tert-butyl 4-(phenylthio)butanoate | 3.60 |
| butan-2-yl 4-(phenylthio)butanoate | 3.94 |
| apicidin | 4.41 |
| 3-(phenylthio)benzoic acid | 4.45 |
| tubacin | 6.34 |

Log P indicates the hydrophobicity of a given molecule, with lipophilic compounds exhibiting higher values (Lipinski, C. A., et al. Experimental and computational approaches to estimate solubility and permeability in drug discovery and development settings. Adv Drug Deliv Rev 46, 3-26, (2001) and Testa, B., et al. Lipophilicity in molecular modeling. Pharm Res 13, 335-343, (1996)). Previous work determined that zebrafish embryos absorb compounds with log P values between 1 and 12 from embryo medium. The 32 compounds and a DMSO control were examined for their ability to generate pericardial edema in zebrafish larvae by 72 hpf (Table 2). Treatment with 12 compounds did not cause a statistically-significant decrease in the number of wild-type larval phenotypes, as compared with controls. This group included the four compounds containing connecting unit substitutions, seven of the known HDACis, and one alkylated analog, tert-butyl 4-(phenylthio)butanoate. Treatment with each of the remaining analogs generated edemic and/or lethal phenotypes that were scored using the phenotype-based classification system described above. Three of these compounds, TSA, valproic acid, and apicidin, are known HDAC inhibitors. The lethality of 3 µM TSA was expected, since it was previously demonstrated that 300 nM TSA killed greater than 90% of treated 72 hpf larvae (FIG. 19).

Table 4. Phenotypes observed in larvae treated with PTBA analogs. Embryos were treated with each compound at 3 µM from 2 hpf, and larvae were scored at 72 hpf using a phenotype-based classification system described above). Compounds below the indicated line exhibit a significant decrease (p <0.05) in the occurrence of wild-type phenotypes as determined by Fisher's exact test.

TABLE 4

Phenotypes observed in larvae treated with PTBA analogs. Embryos were treated with each compound at 3 µM from 2 hpf, and larvae were scored at 72 hpf using a phenotype- based classification system described above). Compounds below the indicated line exhibit a significant decrease (p < 0.05) in the occurrence of wild-type phenotypes as determined by Fisher's exact text.

| Compound Name | Wild-type (WT) | Edemic 1 (E1) | Edemic 2 (E2) | Edemic 3 (E3) | Dead |
|---|---|---|---|---|---|
| 0.5% DMSO | 36 | 0 | 0 | 0 | 0 |
| 4-phenoxybutanoic acid | 36 | 0 | 0 | 0 | 0 |
| 4-(phenylsulfonyl)butanoic acid | 36 | 0 | 0 | 0 | 0 |
| 5-phenylpentanoic acid | 36 | 0 | 0 | 0 | 0 |
| APHA compound 8 | 36 | 0 | 0 | 0 | 0 |
| MS-275 | 36 | 0 | 0 | 0 | 0 |
| PBA | 36 | 0 | 0 | 0 | 0 |
| SAHA | 36 | 0 | 0 | 0 | 0 |
| tubacin | 36 | 0 | 0 | 0 | 0 |
| 4-(phenylamlno)butanoic acid | 35 | 1 | 0 | 0 | 0 |
| Scriptaid | 35 | 1 | 0 | 0 | 0 |
| butanoic acid | 35 | 0 | 0 | 0 | 1 |
| tert-butyl 4-(phenylthio)butanoate | 33 | 3 | 0 | 0 | 0 |
| The compounds below this line cause significant decreases in wild-type larval phenotypes at 3 µM (p > 0.05) | | | | | |
| valproic acid | 25 | 11 | 0 | 0 | 0 |
| 4-(naphthalen-2-ylthlo)butanoic acid | 25 | 9 | 0 | 0 | 2 |
| N-hydroxy-4-[(4-methoxyphenyl)thio]butanamide | 16 | 20 | 0 | 0 | 0 |
| methyl 4-[(4-bromophenyl)thio]butanoate | 8 | 27 | 1 | 0 | 0 |
| 3-(phenylthio)benzoic acid | 2 | 34 | 0 | 0 | 0 |
| 4-[(4-bromophenyl)thio]-N-hydroxybutanamide | 1 | 23 | 12 | 0 | 0 |
| butan-2-yl 4-(phenylthio)butanoate | 2 | 19 | 12 | 2 | 1 |
| PTBA | 0 | 13 | 17 | 5 | 1 |
| methyl 4-[(4-chlorophanyl)thio]butanoate | 0 | 10 | 6 | 19 | 1 |
| methyl 4-[(4-methoxyphenyl)thio]butanoate | 0 | 2 | 24 | 9 | 1 |
| N-hydroxy-4-(phenylthio)butanamide | 0 | 3 | 20 | 13 | 0 |
| propyl 4-(phenylthio)butanoate | 0 | 7 | 8 | 15 | 6 |
| methyl 4-(phenylthio)butanoate | 0 | 0 | 2 | 26 | 8 |

TABLE 4-continued

Phenotypes observed in larvae treated with PTBA analogs. Embryos were treated with each compound at 3 μM from 2 hpf, and larvae were scored at 72 hpf using a phenotype-based classification system described above). Compounds below the indicated line exhibit a significant decrease (p < 0.05) in the occurrence of wild-type phenotypes as determined by Fisher's exact text.

| Compound Name | Wild-type (WT) | Edemic 1 (E1) | Edemic 2 (E2) | Edemic 3 (E3) | Dead |
|---|---|---|---|---|---|
| methyl 4-[(4-methylphenyl)thio]butanoate | 0 | 0 | 2 | 23 | 11 |
| 4-[(4-chlorophenyl)thio]-N-hydroxybutanamide | 0 | 0 | 0 | 22 | 14 |
| N-hydroxy-4-[(4-methylphenyl)thio]butanamide | 0 | 0 | 0 | 14 | 22 |
| 4-[(4-fluorophenyl]thio]-N-hydroxybutanamide | 0 | 0 | 0 | 8 | 28 |
| methyl 4-[(4-fluorophenyl)thio]butanoate | 0 | 0 | 0 | 0 | 36 |
| apicidin | 0 | 0 | 0 | 0 | 36 |
| TSA | 0 | 0 | 0 | 0 | 36 |

Furthermore, with the exception of apicidin, all of the compounds that cause more severe phenotypes than PTBA contain either hydroxamic or alkylated zinc-binding groups. Taken together, these results suggest that modifications of PTBA anticipated to alter its underlying HDACi function may affect compound efficacy during pronephric development. However, pericardial edema can develop as a result of organ dysfunction unrelated to the kidney. Therefore, the effect of each of these compounds, if any, on renal progenitor cells was determined. To accomplish this, lhx1a expression was examined in treated embryos at the 10-somite stage. In situ hybridizations was performed on embryos treated with decreasing concentrations of compound, beginning at 3 μM (Table 5). The results were categorized relative to the efficacy of PTBA at a given concentration and are detailed below.

Table 5. Lhx1a expansion caused by analog treatment. In situ hybridization for lhx1a expression in 10-somite embryos treated from 2 hpf with each compound at the listed concentration. Analogs were classified according to their ability to increase lhx1a expression as effective (+), partially effective (+/−), or ineffective (−). Analogs that killed all embryos at a given concentration before reaching 10 somites are listed as XX. If the efficacy of a compound was not determined at a given concentration it is listed as ND. Note1: embryos surviving treatment with 800 nM apicidin (31%, n=36) displayed general toxicity precluding efficacy scoring.

TABLE 5

Lhx1a expansion caused by analog treatment. In situ hybridization for lhx1a expression in 10-somite embryos treated from 2 hpf with each compound at the listed concentration. Analogs were classified according to their ability to increase lhx1a expression as effective (+), partially effective (+/−), or ineffective (−). Analogs that killed all embryos at a given concentration before reaching 10 somites are listed as XX. If the efficacy of a compound was not determined at a given concentration it is listed as ND.

| Compound Name | 3 μM | 1.5 μM | 800 nM | 400 nM | 200 nM | 100 nM |
|---|---|---|---|---|---|---|
| 0.5% DMSO | − | − | − | − | − | − |
| 4-phenoxybutanoic acid | − | ND | ND | ND | ND | ND |
| 4-(phenylsulfonyl)butanoic acid | − | ND | ND | ND | ND | ND |
| 5-phenylpentanoic acid | − | ND | ND | ND | ND | ND |
| APHA compound 8 | − | ND | ND | ND | ND | ND |
| MS-275 | − | ND | ND | ND | ND | ND |
| PBA | − | ND | ND | ND | ND | ND |
| SAHA | − | ND | ND | ND | ND | ND |
| tubacin | − | ND | ND | ND | ND | ND |
| 4-(phenylamino)butenoic acid | − | ND | ND | ND | ND | ND |
| Scriptoid | +/− | ND | ND | ND | ND | ND |
| butanoic acid | − | ND | ND | ND | ND | ND |
| tert-butyl 4-(phenylthio)butanoate | +/− | ND | ND | ND | ND | ND |
| valproic acid | +/− | ND | ND | ND | ND | ND |
| 4-(naphthalen-2-ylthio)butenoic acid | − | ND | ND | ND | ND | ND |
| N-hydroxy-4-[(4-methoxyphenyl)thio]butanamide | +/− | ND | ND | ND | ND | ND |
| methyl 4-[(4-bromophenyl)thio]butanoate | +/− | ND | ND | ND | ND | ND |
| 3-(phenylthio)benzoic acid | − | ND | ND | ND | ND | ND |
| 4-[(4-bromophenyl)thio]-N-hydroxybutanamide | + | +/− | ND | ND | ND | ND |
| butan-2-yl 4-(phenylthio)butanoate | + | + | +/− | ND | ND | ND |
| PTBA | + | + | +/− | ND | ND | ND |
| methyl 4-[(4-chlorophenyl)thio]butanoate | + | +/− | ND | ND | ND | ND |
| methyl 4-[(4-methoxyphenyl)thio]butanoate | + | + | + | +/− | − | ND |
| N-hydroxy-4-(phenylthio)butanamide | + | + | +/− | ND | ND | ND |
| propyl 4-(phenylthio)butanoate | + | + | +/− | ND | ND | ND |
| methyl 4-(phenylthio)butanoate | + | + | +/− | ND | ND | ND |
| methyl 4-[[4-methylphenyl]thio]butenoate | + | + | + | − | − | ND |
| 4-[(4-chlorophenyl)thio]-N-hydroxybutanamide | + | + | +/− | ND | ND | ND |
| N-hydroxy-4-[(4-methylphenyl)thio]butenamide | + | + | + | − | − | ND |
| 4-[(4-fluorophenyl)thio]-N-hydroxybutanamide | + | + | + | +/− | − | ND |
| methyl 4-[(4-(tuorophenyl)thio]butanoato | XX | + | + | +/− | +/− | ND |

TABLE 5-continued

Lhx1a expansion caused by analog treatment. In situ hybridization for lhx1a expression in 10-somite embryos treated from 2 hpf with each compound at the listed concentration. Analogs were classified according to their ability to increase lhx1a expression as effective (+), partially effective (+/−), or ineffective (−). Analogs that killed all embryos at a given concentration before reaching 10 somites are listed as XX. If the efficacy of a compound was not determined at a given concentration it is listed as ND.

| Compound Name | 3 µM | 1.5 µM | 800 nM | 400 nM | 200 nM | 100 nM |
|---|---|---|---|---|---|---|
| apicidin | XX | XX | XX[1] | +/− | − | ND |
| TSA | XX | XX | XX | XX | + | + |

Note[1]:
embryos surviving treatment with 800 nM apicidin (31%, n = 36) displayed general toxicity precluding efficacy scoring.

Figure 26:
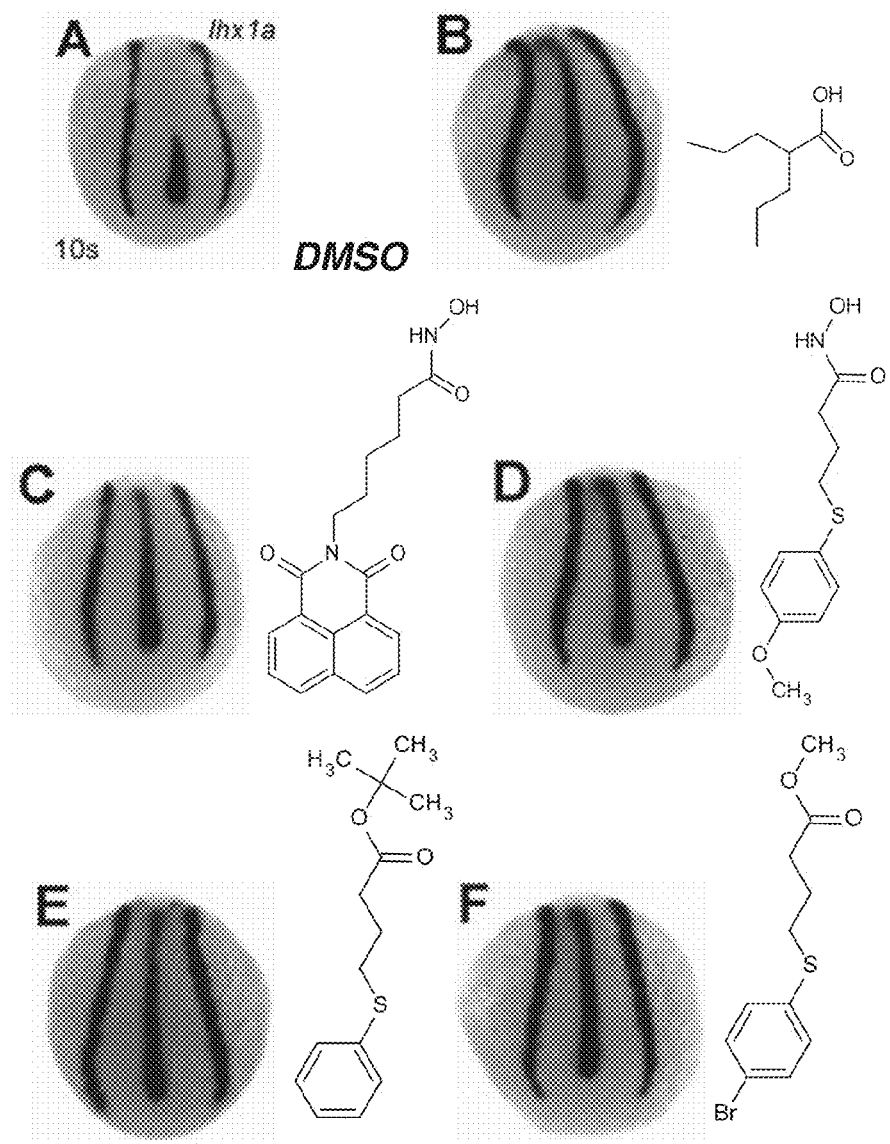
FIG. 26. PTBA analogs exhibiting partial efficacy at 3 µM. (A through F) In situ hybridization for lhx1a expression in 10-somite embryos treated from 2 hpf with 0.5% DMSO (A) or 3 µM of the following compounds: valproic acid (20% expansion) (B), Scriptaid (25% expansion) (C), N-hydroxy-4-[(4-methoxyphenyl)thio]butanamide (31% expansion) (D), tert-butyl 4-(phenylthio)butanoate (39% expansion) (E), and methyl 4-[(bromophenyl)thio]butanoate (74% expansion) (F).

PTBA Analog Efficacy in Renal Progenitor Cells at 3 µM:

Of the 12 compounds that exhibited no significant effect on larval phenotype, 10 compounds did not expand lhx1a expression as compared with controls (no expansion, n=36) (Tables 4 and 5). This group includes HDACis, such as SAHA and tubacin, which exhibit similar potency to TSA in vitro (Bradner, J. E. et al. Chemical phylogenetics of histone deacetylases. Nat Chem Biol 6, 238-243, (2010)). However, treatment with 3 µM Scriptaid or tert-butyl 4-(phenylthio)butanoate increased lhx1a expression in 39% and 25% of the tested embryos (n=36 each), respectively, as compared with controls (no expansion, n=36) (FIGS. 26, A, C, and E). Therefore, the failure to develop pericardial edema following treatment is a predictive, but not absolute, indicator of an ineffective analog.

Lhx1a expression analysis separated the 20 compounds, including PTBA, which caused edemic or lethal phenotypes into four groups. The first group, consisting of 4-(napthalen-2-ylthio)butanoic acid and 3-(phenylthio) benzoic acid, caused no expansion of lhx1a in the treated embryos (Table 5). Therefore, their edemic phenotypes probably result from non-kidney related effects during embryonic development. The second group, consisting of three compounds, expanded lhx1a expression in less than 75% of the treated embryos in comparison to controls (FIG. 26A). This group included valproic acid, a known HDACi, (20% expansion, n=35), N-hydroxy-4-[(4-methoxyphenyl)thio] butanamide (31% expansion, n=35), and methyl 4-[(bromophenyl)thio]butanoate (74% expansion, n=35) (FIGS. 26, B, D, and F). The third group consisted of 12 effective compounds, including PTBA, which expanded lhx1a expression in greater than 90% of the treated embryos as compared with controls (Table 3). The eleven PTBA analogs all contained either hydroxamic or alkylated zinc-binding groups. Compounds with these structural motifs also caused the most edema and lethality in the phenotypic screen (Table 2). Furthermore, all compounds showing greater than 90% efficacy by in situ hybridization demonstrate phenotypic effects similar to or more severe than those caused by PTBA (Tables 2 and 3). Therefore, the severity of edemic phenotypes does appear to correlate with the ability of a given PTBA analog to expand renal progenitor cells with some exceptions as previously noted. These compounds were subsequently tested to determine their efficacies at sequentially lower concentrations. The final group, consisting of methyl 4-[(4-fluorophenyl)thio)]butanoate, apicidin, and trichostatin A, killed all treated embryos before they reached the 10-somite stage (Table 3). Toxicity of these compounds at 3 µM does not preclude them from expanding renal progenitor cells at lower concentrations. Indeed, treating embryos with 200 nM TSA expands lhx1a expression in a manner similar to 3 µM PTBA (FIG. 16D compared with FIG. 4B). Therefore, the efficacy of these compounds at concentrations below 3 µM was assessed along with the previous group.

Figure 27A:
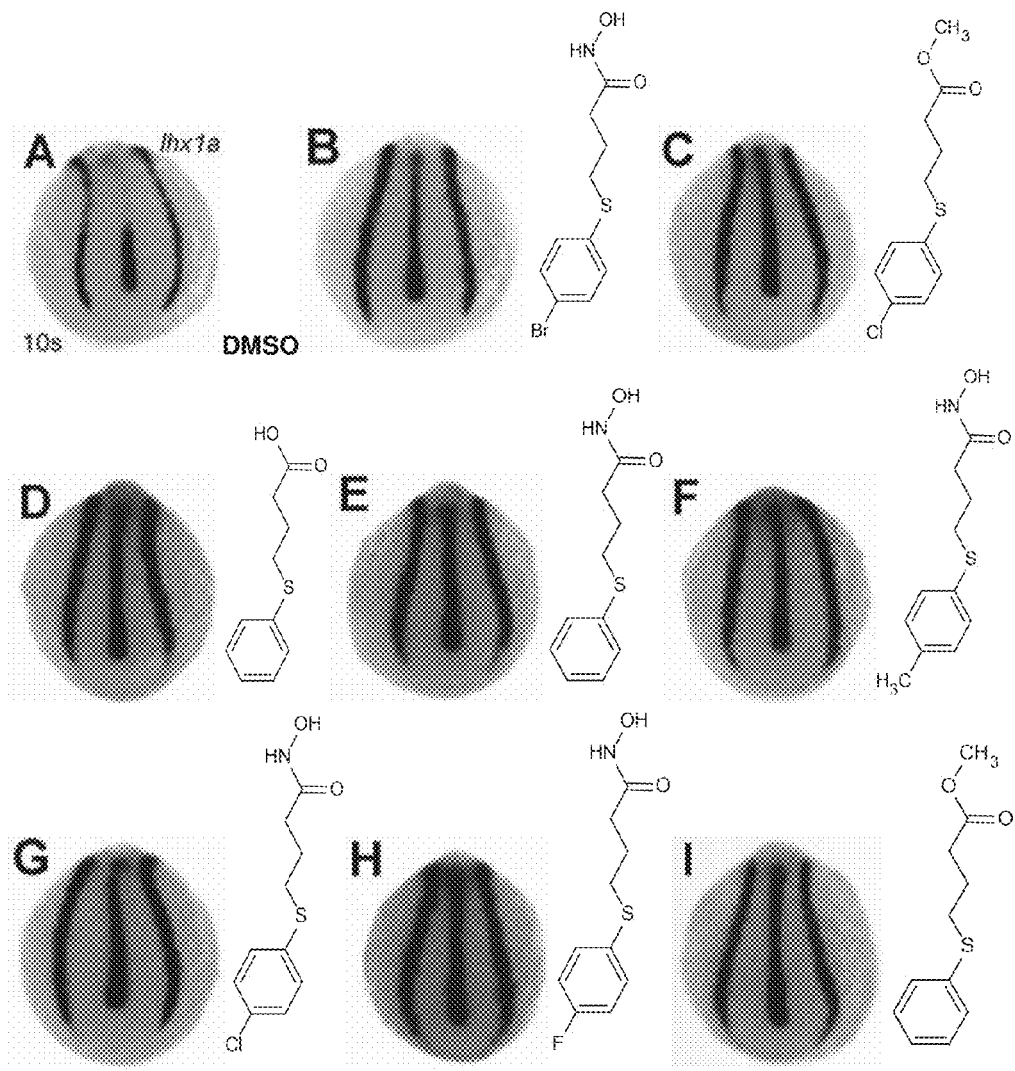
FIG. 27. PTBA analogs exhibiting efficacy at 1.5 µM. (A through N) In situ hybridization for lhx1a expression in 10-somite embryos treated from 2 hpf with 0.5% DMSO (A) or 1.5 µM of the following compounds: 4-[(bromophenyl)thio]-N-hydroxybutanamide (47% expansion) (B), 4-[(4-chlorophenyl)thio]butanoate (72% expansion) (C), PTBA (83% expansion) (D), N-hydroxy-4-(phenylthio)butanamide (92% expansion) (E), N-hydroxy-4-[(4-methylphenyl)thio]butanamide (97% expansion) (F), 4-[(4-chlorophenyl)thio]-Nhydroxybutanamide (97% expansion) (G), 4-[(4-fluorophenyl)thio]-N-hydroxybutanamide (100% expansion, n=36) (H), methyl-4-(phenylthio)butanoate (89% expansion) (I), methyl 4-[(4-methoxyphenyl)thio]butanoate (91% expansion) (J), methyl 4-[(4-methylphenyl)thio] butanoate (100% expansion) (K), methyl 4-[(4-fluorophenyl)thio]butanoate (100% expansion) (L), propyl 4-(phenylthio)butanoate (89% expansion) (M), and butan-2-yl 4-(phenylthio) butanoate (89% expansion) (N).
Figure 27B:
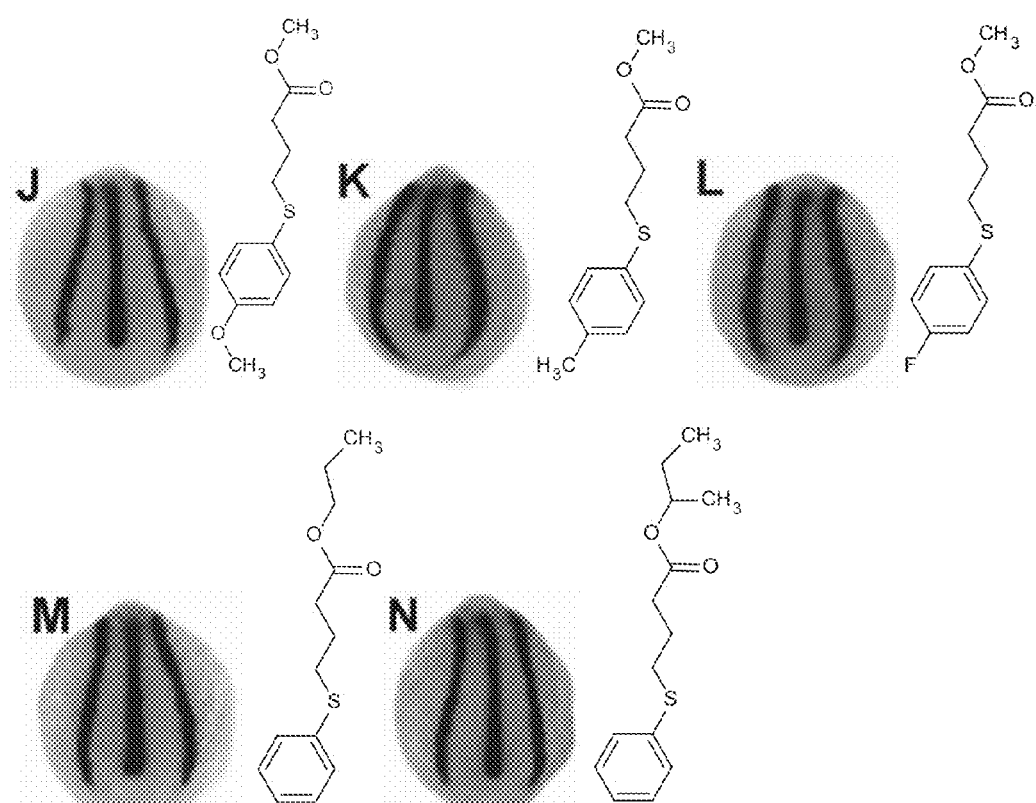

PTBA analog efficacy in renal progenitor cells at 1.5 µM: Two compounds, apicidin and TSA, were lethal at 1.5 µM, while 13 others demonstrated some ability to expand lhx1a expression in 10-somite embryos. Two of these were partially effective, expanding less than 75% of the treated embryos when compared with controls (no expansion, n=36) (FIG. 27A). These were 4-[(bromophenyl)thio]-N-hydroxybutanamide (47% expansion, n=36) and methyl 4-[(4-chlorophenyl)thio]butanoate (72% expansion, n=36) (FIGS. 27, B and C). Because they lacked the efficacy of the remaining analogs, these compounds were not evaluated further. Eleven compounds, including PTBA (83% expansion, n=35) (FIG. 27D), showed efficacy in greater than 80% of the treated embryos. Four contained hydroxamic zinc-binding groups, with three of these also carrying a substituted aliphatic cap: N-hydroxy-4-(phenylthio)butanamide (92% expansion, n=36), N-hydroxy-4-[(4-methylphenyl)thio] butanamide (97% expansion, n=33), 4-[(4-chlorophenyl)thio]-N-hydroxybutanamide (97% expansion, n=36), and 4-[(4-fluorophenyl)thio]-N-hydroxybutanamide (100% expansion, n=36) (FIG. 27, E through H).

Four analogs had methylated zinc-binding groups, with three of these also including aliphatic cap substitutions: methyl-4-(phenylthio)butanoate (89% expansion, n=36), methyl 4-[(4-methoxyphenyl)thio]butanoate (91% expansion, n=35), methyl 4-[(4-methylphenyl)thio] butanoate (100% expansion, n=36), and methyl 4-[(4-fluorophenyl) thio]butanoate (100% expansion, n=30) (FIG. 27, I through L). The remaining two analogs demonstrating over 80% efficacy carried propyl- and sec-butyl substitutions, respectively, on their zinc-binding groups: propyl 4-(phenylthio) butanoate (89% expansion, n=36) and butan-2-yl 4-(phenylthio)butanoate (89% expansion, n=35) (FIGS. 27, M and N). Because each of these 10 PTBA analogs exhibited efficacy above that of PTBA, these data support the approach of targeting motifs important in HDACi activity.

PTBA Analog Efficacy on Renal Progenitor Cells at 800 nM:

Treatments at 800 nM revealed two distinct groups of analogs based on efficacy. The partially effective compounds, consisting of PTBA and five analogs, expanded lhx1a expression in less than 25% of treated 10-somite embryos as compared with controls (Table 3). With the exception of 4-[(4-chlorophenyl)thio]-N-hydroxybutanamide, none of these compounds carried a substituted aliphatic cap. Because of their already limited efficacy at 800 nM, these compounds were not tested at lower concentrations. The five members of the more effective second group increased lhx1a expression in greater than 45% of treated embryos as compared with controls (no expansion, n=36)

(FIG. 28A). This group of analogs included methyl 4-[(methylphenyl)thio]butanoate (49% expansion, n=35), methyl 4-[(methoxyphenyl)thio] butanoate (57% expansion, n=35), 4-[(4-fluorophenyl)thio]-N-hydroxybutanamide (60% expansion, n=35), N-hydroxy-4[(methylphenyl)thio] butanamide (61% expansion, n=36) and methyl 4-[(4-fluorophenyl)thio]butanoate (64% expansion, n=36) (FIG. 28, B through F).

Each of these compounds contained substitutions in both the zinc-binding group and aliphatic cap. These substitutions represented only a limited selection of functional groups. The zincbinding groups contained either hydroxamic acids or methylated carboxylic acids, while the aliphatic caps carried either methyl-, methoxy-, or fluoro-substitutions. These results suggest that certain structural motifs impart improved efficacy to the PTBA backbone.

Treatment with 800 nM apicidin killed 69% of the treated embryos (n=36) (Table 3). Surviving embryos exhibited general toxicity that precluded the scoring of lhx1a expansion (data not shown). TSA treatment at 800 nM was lethal (Table 3). The five analogs exhibiting greater than 45% efficacy, apicidin, and TSA were retested at 400 nM.

PTBA Analog Efficacy on Renal Progenitor Cells at 400 nM or Below:

Three of the five remaining structural analogs of PTBA and apicidin exhibited a partial ability to expand lhx1a expression at 400 nM in comparison to controls (n=35) (FIG. 29A). Of these, 400 nM 4-[(4-fluorophenyl)thio]-N-hydroxybutanamide expanded 35% of treated embryos (n=34), the highest percentage of any tested PTBA structural analog at this concentration (FIG. 29B). Two others, methyl 4-[(methoxyphenyl)thio]butanoate (29% expansion, n=35) (FIG. 29C) and methyl 4-[(4-fluorophenyl)thio]butanoate (26% expansion, n=35), increased lhx1a expression in over 25% of treated embryos. Furthermore, methyl 4-[(4-fluorophenyl)thio]butanoate also caused partial lhx1a expansion at 200 nM (22% expansion, n=32) (FIG. 29D), while the other two structural analogs were ineffective (Table 3). This represents the lowest observed concentration of a structural PTBA analog capable of expanding renal progenitor cells.

Treatment with 400 nM apicidin expanded 22% of treated embryos (n=36) (FIG. 29E), but was ineffective at 200 nM. All embryos treated with 400 nM trichostatin A died before reaching 10 somites (Table 3). However, treatment with 200 nM TSA caused lhx1a expansion in 100% of treated embryos as compared with controls (n=29) (Table 3). This observation is in agreement with my previous results (FIG. 16D). Treatment with 100 nM TSA was also effective (97% expansion, n=35), marking the lowest tested concentration of any PTBA analog, structural or functional, affecting renal progenitor cells (FIG. 29F).

Toxicity Assays:

The cytotoxicity of the 15 compounds exhibiting efficacy or lethality at 3 μM was tested in a conditionally-immortalized mouse podocyte cell line. Podocytes are polarized epithelial cells located on the glomerular basement membrane that contribute to the integrity of the filtration barrier. For the purposes of these experiments, they function as an indicator of renal toxicity. Following 72 hours of treatment with each compound concentrations ranging from 30 μM to 3 nM, podocyte viability was assessed by measuring residual metabolic activity (FIG. 30). From these data, the concentration where 50% of the exposed podocytes remained viable ($E_{50}$) was calculated. Of the 15 analogs tested, only two, TSA and apicidin, caused sufficient cytotoxicity to allow the calculation of an $E_{50}$ value. Over the course of three experiments, TSA exhibited a mean $E_{50}$ of 96 nM (s=51 nM), while the mean $E_{50}$ for apicidin was 152 nM (s=54 nM). Treatment with PTBA or each of 12 structural analogs never decreased podocyte viability below the 50% threshold, even when tested at 30 μM (FIG. 30). In fact, over three experiments, podocyte viability never dropped 75 below 80% following treatment with any of these compounds. Therefore PTBA analogs, carrying cap and/or zinc-binding group modifications, do not increase the toxicity of the compound relative to PTBA. These results suggest that the efficacy of PTBA can be improved through analog development without causing a corresponding increase in compound toxicity.

Methods

Zebrafish husbandry was performed as described above

Compound Sources and Treatments:

PTBA and methyl-4-(phenylthio)butanoate were synthesized as described above. 4-(Naphthalen-2-ylthio)butanoic acid (NSC2733) and 3-(phenylthio)benzoic acid (NSC113994), were obtained from the NCI/DTP Open Repository. APHA compound 8, Apicidin, butanoic acid, PBA, 4-phenoxybutanoic acid, 5-phenylpentanoic acid, Scriptaid, TSA, and valproic acid were obtained from Sigma-Aldrich. MS-275 and SAHA were obtained from Cayman Chemical Co. 4-(phenylsulfonyl)butanoic acid was obtained from Matrix Scientific. Tubacin was a gift of Dr. Ralph Mazitschek of the Broad Institute (Cambridge, Mass.). The remaining PTBA analogs were synthesized. Three independent groups of 12 chorionated 2 hpf embryos were arrayed in individual wells of 24-well plates. E3 medium was removed with a glass pipette and replaced with 800 μl treatment solutions containing 0.5% DMSO in E3 with or without compound at the reported concentrations.

In Situ Hybridization:

In situ hybridization for lhx1a was performed as described above. Embryos were considered expanded if they exhibited lhx1a expression consistent with that resulting from treatment with 3 μM PTBA. Compounds were classified as effective, partially-effective or ineffective based on comparison to the effects of PTBA at a given concentration.

Phenotypic Screening:

Phenotypic screening of PTBA analogs was performed identically to the concentration-response experiments detailed above. Embryos were treated with each PTBA analog from 2 to 72 hpf as described above.

Podocyte Cytotoxicity Assays:

The isolation and characterization of conditionally-immortalized mouse podocyte cell line have been previously described (Mundel, P. et al. Rearrangements of the cytoskeleton and cell contacts induce process formation during differentiation of conditionally immortalized mouse podocyte cell lines. *Exp Cell Res* 236, 248-258, (1997) and Schwartz, E. J. et al. Human immunodeficiency virus-1 induces loss of contact inhibition in podocytes. *J Am Soc Nephrol* 12, 1677-1684, (2001)). Mouse podocytes were plated at a density of 6,000 cells per 200 μl in 96-well plates to elicit log-phase growth. The indicated PTBA analogs were added at 30 μM, 10 μM, 1 μM, 300 nM, 100 nM, 30 nM, or 3 nM and incubated at 33° C. for 72 hours. The final DMSO concentration was maintained at 0.2% in all treatments except 30 μM (0.6%). After incubation, cytotoxicity was analyzed using the Cell Titer-Blue Cell Viability Assay (Promega) per manufacturer's instructions. Reagent (20 μl) was added to 100 μl of cells and plates were incubated for 2 hours at 37° C. Fluorescence was read at 79 560Ex/590Em on a Gemini SpectramaxXS (Molecular Devices) plate reader. Viability was calculated as a percentage of the DMSO control, which was considered 100% viability. Data represent the results of three independent experiments using duplicate wells for each condition. E50 values were determined from the transformed and normalized data by non-linear regression.

Discussion

From a screen of almost 2000 small molecules, we identified a compound, PTBA, that had not been previously reported as a "hit" in 136 previous chemical library screens (NCBI—PubChem). The success of our screen validates the use of an edemic phenotype as an indicator of aberrant kidney development. Furthermore, it emphasizes the importance of sound experimental design in determining the desired outcome. Many factors should be considered before beginning to interrogate libraries containing thousands of small molecules. Indeed, depending on the predetermined goals and parameters of the screen, investigators can generate completely different data sets using the same compound library. To illustrate this point, chemical screens performed by two labs (de Groh, E. D. et al. Inhibition of histone deacetylase expands the renal progenitor cell population. J Am Soc Nephrol 21, 794-802, (2010) and Molina, G. et al. Zebrafish chemical screening reveals an inhibitor of Dusp6 that expands cardiac cell lineages. Nat Chem Biol 5, 680-687, (2009)). Both groups tested zebrafish embryos at 10 µM using NCI/DTP Diversity Set compounds drawn from daughter plates derived from the same DMSO stocks. Furthermore, each lab identified a compound, PTBA or BCI, which expanded progenitor cells, leading to increased kidney or heart size, respectively. However, the differing experimental approaches utilized by the two groups masked the effects of the other small molecule. BCI was identified by treating transgenic embryos carrying a fluorescent FGF-signaling reporter from 24 to 32 hpf. Since PTBA loses efficacy at about 15 hpf and edema typically does not develop until at least 48 hpf, PTBA-treated embryos would appear wild-type. Therefore, even if they had recorded interesting secondary phenotypes beyond those involved in FGF signaling, PTBA would have been missed using that approach. Likewise, BCI-treated 72 hpf larvae were scored as wild-type in our phenotypic screen, even though they almost certainly contained enlarged hearts. Although both screens were ultimately successful, their unique observations depended on the selection of treatment windows and phenotypes appropriate for the research. Without these considerations, the effects of interesting small molecules can be easily overlooked.

Another important factor contributing to the discovery of PTBA was the concentration chosen for the screen. In this, we were very fortunate. All compounds were ostensibly tested at 10 µM in embryo medium. Had this truly been the case, the data suggest that PTBA treatment would have killed all the embryos before reaching 72 hpf. Since we performed no further characterization on compounds found to be lethal at the screening concentration, PTBA might never have been characterized. Luckily, compound concentrations in DMSO stocks can vary several fold from the reported value in small molecule libraries (Popa-Burke, I. G. et al. Streamlined system for purifying and quantifying a diverse library of compounds and the effect of compound concentration measurements on the accurate interpretation of biological assay results. Anal Chem 76, 7278-7287, (2004)). Thus, the concentration in the PTBA-containing well was probably much closer to 3-5 µM, allowing edema formation and generating a positive hit. Furthermore, had we decided to screen at a lower concentration, the larvae may have appeared wild-type, again precluding any further testing. This exposes a flaw in the way many small molecule screens are performed: very few involve screening at multiple concentrations. It could be argued that repeated screening of a library is a waste of time and effort, especially if hits have been identified. However, small molecule libraries generally already represent a significant investment of resources, and follow-up screens at different concentrations merit consideration. At the very least, compounds observed to be lethal in the initial screen could be retested at lower concentrations in search of relevant phenotypes.

Treating zebrafish embryos with PTBA stimulates RA signaling, as evidenced by its effects on the RA-responsive genes cyp26a1 and cmlc2. Consequently, blocking RA signaling at the receptor level with dominant-negative RARα greatly reduced PTBA efficacy. Therefore, PTBA likely interacts with some elements of the RA signaling pathway in order to stimulate renal progenitor cell proliferation during pronephric development. The characterization of PTBA as a novel HDACi suggests that the targets are most likely the HDACs controlling the repression of RA-responsive genes.

In the absence of RA, an RAR/RXR dimer binds the RARE in regulated promoters and recruits complexes of corepressor proteins, including an HDAC (FIG. 31A). The HDAC deacetylates nearby nucleosomes, causing chromatin condensation which inhibits gene transcription. When RA binds the RAR/RXR dimer, it elicits a conformational change that removes the HDAC from close proximity to the nucleosomes (FIG. 31B). This facilitates the activity of coactivators, such as histone acetyltransferases, which decondense the chromatin and allow transcription to occur. By inhibiting the corepressor HDAC, HDACis have been hypothesized to lower the RA concentration necessary to activate the RAR/RXR dimer (FIG. 31C). In this way, PTBA could stimulate RA signaling at the receptor level without affecting the endogenous RA concentration.

The downstream target of RA-signaling that mediates the effects of PTBA on renal progenitor cells remains unknown. Since my results argue that PTBA treatment stimulates renal progenitor cell proliferation without significantly transforming juxtaposed tissues, the effect is probably local. Therefore, PTBA may enhance RA signaling directly within renal progenitor cells, leading to increased proliferation. Because attenuation does not require the synthesis of protein intermediates, this hypothesis is compatible with the previous work of Cartry and coworkers (Cartry, J. et al. Retinoic acid signalling is required for specification of pronephric cell fate. Dev Biol 299, 35-51, (2006)). They observed that treating Xenopus embryos with RA caused lhx1a expansion even in the presence of the protein synthesis inhibitor, cycloheximide. Furthermore, treating kidney epithelial cell lines with RA increased both thymidine uptake and the proportion of cells in S-phase (Anderson, R. J., et al. Retinoic acid regulation of renal tubular epithelial and vascular smooth muscle cell function. J Am Soc Nephrol 9, 773-781, (1998) and Argiles, A., et al. Retinoic acid affects the cell cycle and increases total protein content in epithelial cells. Kidney Int 36, 954-959, (1989)). Therefore, it is possible that the proliferative machinery in renal progenitor cells may respond to RA-signaling in a similar manner.

Therapeutic Potential of PTBA.

In many respects, the process of kidney regeneration mimics that of nephrogenesis. In both cases, a multipotent cell first proliferates to provide the necessary raw material and then differentiates into the required tissue type. Several hypotheses have been proposed to explain the source of the multipotent cells involved in regeneration. The first, and most generally accepted, suggests that these cells arise from tissue dedifferentiation near the site of damage. Other groups argue that the multipotent cells are actually stem cells of intrarenal or extrarenal origin. In any case, it is reasonable to assume that these cells share elements in common with renal progenitor cells. Therefore, it was hypothesized that they may also exhibit similar proliferation in response to PTBA treatment. This hypothesis may explain the observations made by other groups regarding the relationship between HDAC inhibition and renal regeneration. In one study, Imai and coworkers demonstrated that treating mice with daily injections of TSA attenuated renal damage following injury (Imai, N. et al. Inhibition of histone deacetylase activates side population cells in kidney and partially reverses chronic renal injury. Stem Cells 25, 2469-2475, (2007)). Since PTBA and TSA both function as HDACis and expand renal progenitor cells, they may also act similarly in facilitating renal regeneration. In another study, Marumo and coworkers demonstrated that the expression of Hdac5 was significantly decreased following acute ischemic damage in mouse kidneys (Marumo, T., et al. Epigenetic regulation of BMP7 in the regenerative response to ischemia. J Am Soc Nephrol 19, 1311-1320, (2008)). This suggests that the reduction of HDAC activity may serve as an important part of the regeneration process. Therefore, at least some evidence supports the idea that PTBA may function as a useful therapeutic following acute kidney injury.

To test this hypothesis, we used a transgenic mouse model of acute kidney injury using diphtheria toxin (DT) as a nephrotoxic agent. Unlike humans, mice are normally resistant to DT exposure. This resistance arises from several amino acid differences in the protein acting as the DT receptor, heparin-binding EGF-like growth factor (Hbegf) (Mitamura, T., et al. Diphtheria toxin binds to the epidermal growth factor (EGF)-like domain of human heparin-binding EGF-like growth factor/diphtheria toxin receptor and inhibits specifically its mitogenic activity. J Biol Chem 270, 1015-1019, (1995)). Transgenic mice (PTC-DTR) express human HBEGF in their proximal tubules, creating the conditions for an acute and specific damage event. Since blood is a buffered solution, testing PTBA would have been a poor choice. At neutral pH, the zinc-binding group would be deprotonated and the resulting polar charge would greatly decrease its absorption through cell membranes. Instead we tested an effective structural analog carrying a methylated zinc-binding group, methyl 4-(phenylthio)butanoate (MPTB). PTC-DTR mice were injected with DT and damage was allowed to accrue for one day. At this time, mice were given daily injections of MPTB or a DMSO control for the next six days. Preliminary data from a single group of mice suggest that MPTB treatment significantly increases the rate of renal recovery by approximately 30% (FIG. 32). Therefore, PTBA analogs demonstrate some promise as renal therapeutics following acute kidney injury.

Toxicity is also an important consideration during the development of any drug. At its effective concentration, PTBA exhibited much milder effects on juxtaposed mesodermal tissues in comparison to TSA. Furthermore, structural PTBA analogs, even when administered at 30 µM, demonstrated little effect on podocyte cell viability in cell culture assays. However, the data above suggests that treating podocytes with 100 nM TSA would be expected to kill at least 50% of the cells within 72 hours. There are at least two possible explanations for this difference in toxicity, each reflecting different considerations of HDAC-HDACi binding. Crystallography studies have revealed how several HDACis block substrate access by interacting with the $Zn^{2+}$ in the catalytic site of an HDAC. Therefore, most HDACis, including carboxylic and hydroxamic acids, function as competitive inhibitors of HDACs, although noncompetitive HDACis, such as Trapoxin A, have been characterized. In this example, taken from the Protein Data Bank, TSA occupies the binding site of human HDAC7 by coordinating its hydroxamic acid motif with the catalytic $Zn^{2+}$ (FIG. 33). In general, hydroxamic HDACis bind HDACs much more strongly than HDACis containing carboxylic acid zinc-binding groups, such as PTBA (Jacobsen, F. E., et al. ChemMedChem 2, 152-171, (2007)). This is because PTBA should form only one coordinate bond with the active site zinc, an arrangement known as monodentate binding. In contrast, the hydroxamic acid of TSA binds in a bidentate fashion, forming two coordinate bonds with the active site zinc. This difference is reflected in the results of our in vitro HDAC analysis. TSA is observed to inhibit all HDAC activity at micromolar concentrations, while PTBA reduced HDAC activity by only 70% at millimolar concentrations. However, this large efficacy difference is not evident in vivo. PTBA and TSA were found to generate similar increases in histone hyperacetylation at concentrations within about one log of each other. These data suggest that additional factors may be involved in determining compound efficacy in the context of a whole organism.

The difference in HDAC isoform specificity between carboxylic and hydroxamic acids may provide a possible explanation for these observations. HDAC isoforms are separated into four classes based on their size, homology, cellular localization, and catalytic activity (FIG. 34). For example, Class I isoforms generally exhibit nuclear localization, while Class II HDACs are primarily cytoplasmic (Balasubramanian, S., et al. Isoform-specific histone deacetylase inhibitors: the next step?Cancer Lett 280, 211-221, (2009)). Carboxylic acid HDACis are considered to be specific inhibitors of Class I and IIa HDACs, while hydroxamic acids target Class I, II, and IV isoforms (FIG. 34, Bieliauskas, A. V. et al. Isoform-selective histone deacetylase inhibitors. Chem Soc Rev 37, 1402-1413, (2008); Bolden, J. E., et al. Anticancer activities of histone deacetylase inhibitors. Nat Rev Drug Discov 5, 769-784, (2006); Butler, K. V. et al. Chemical origins of isoform selectivity in histone deacetylase inhibitors. Curr Pharm Des 14, 505-528, (2008); and Khan, N. et al. Determination of the class and isoform selectivity of small-molecule histone deacetylase inhibitors. Biochem J 409, 581-589, (2008)). Meanwhile, the Class III HDACs (sirtuins), utilize an NAD+-dependent catalysis mechanism that remains unaffected by carboxylic or hydroxamic HDACis (FIG. 34). Although the class specificity of PTBA has not yet been confirmed, it can be hypothesized to function as a Class I/IIa-specific inhibitor like other carboxylic acids.

Several inferences can be made from these isoform specificities. First, if PTBA efficacy in zebrafish embryos does indeed require the inhibition of one or more HDAC isoforms, then hdacs 6, 10, and 11 are probably not targeted. Therefore, it is possible that the increased toxicity observed in TSA-treated embryos may result from its effect on these hdacs. Of particular interest is HDAC6, which functions as a microtubule-associated deacetylase (Hubbert, C. et al. HDAC6 is a microtubule-associated deacetylase. Nature 417, 455-458, (2002)). Affecting the posttranslational modifications of the microtubule network causes broad effects on cell signaling and the maintenance of homeostasis. However, embryos treated with tubacin, an HDAC6-specific HDACi (Haggarty, S. J., et al. Domain-selective small-molecule inhibitor of histone deacetylase 6 (HDAC6)-mediated tubulin deacetylation. Proc Natl Acad Sci USA 100, 4389-4394, (2003)), appeared wild-type in my phenotypic screens. It is possible that tubacin's Log P of 6.34, the highest of any tested PTBA analog, may prevent efficient compound absorption and could account for the lack of phenotype. Furthermore, the broad specificity of hydroxamic HDACis suggested that hydroxamic PTBA analogs would demonstrate greater efficacy at the expense of increased toxicity. Indeed, several hydroxamic analogs increased lhx1a expression in treated embryos at concentrations equal to or less than PTBA. However, the ata from zebrafish embryos and podocyte culture suggest that this modification has little to no effect on compound toxicity. This may imply that the hydroxamic analogs remain weak inhibitors despite the improved strength of the zinc-binding group. Accordingly, their HDACi activity should be determined empirically in future in vitro assays. Alternatively, the products generated from the metabolism of TSA may cause the deleterious effects observed in treated embryos. Indeed, some evidence suggests that the N-demethylated byproducts of TSA remain pharmacologically active and persist in the circulation for at least an hour following administration (Sanderson, L. et al. Plasma pharmacokinetics and metabolism of the histone deacetylase inhibitor trichostatin after intraperitoneal administration to mice. Drug Metab Dispos 32, 1132-1138, (2004)). However, it is currently unknown if these metabolic waste products affect normal cellular processes.

Previous clinical studies with known HDACis suggest that structural analogs of PTBA may function as viable therapeutics. Indeed, both trichostatin A (Vorinostat) and valproic acid have received U.S. Food and Drug Administration (FDA) approval for oral administration to treat T-cell lymphoma and epilepsy, respectively. Importantly, the sodium salt of PBA (Buphenyl), one of the closest structural analogs of PTBA, also received FDA approval in 1996 for the treatment of urea cycle disorders. To date, Buphenyl remains the only FDA-approved treatment for chronic management of the excess blood ammonia (hyperammonemia) generated by enzymatic deficiencies in urea metabolism. Prescribed daily doses of Buphenyl as an oral medication often reach gram quantities, with some patients taking as much as 20 g/day. Thus, it may be possible to safely administer other PTBA analogs at similarly high doses. In addition, Buphenyl exhibits good bioavailability of about 80% when taken orally. Unfortunately, Buphenyl has a short half-life ($t_{1/2}$~1 hr) following administration, as it is rapidly converted to phenylacetic acid. However, this limitation can be easily overcome by prescribing multiple daily dosings. Therefore, the favorable pharmacological properties of sodium PBA support the future development of other PTBA analogs for clinical use.

Certain questions remain open from this study. Although, the zebrafish pronephros serves as an excellent model of individual metanephric nephrons, metanephroi are complex organs consisting of millions of nephrons. It is unknown how accurately simple pronephric models reflect conditions within the broader context of general metanephric kidney function. Future experiments with PTBA analogs in mouse models of kidney injury may help to address this. Furthermore, while my data suggest that PTBA treatment affects normal pronephric function, thus causing the edemic phenotype, this was not determined empirically. Although the pronephros is almost certainly nonfunctional at 48 hpf because the glomerulus has not yet formed, fluorescent dextran injections could provide further confirmation. Indeed, it would be interesting to determine if PTBA-treated embryos manage to form functional pronephroi later in development. This research has provided some insight into the mechanism of PTBA efficacy, revealing the involvement of the RA signaling pathway and HDAC inhibition. However, the specific target of PTBA activity remains unknown. Ostensibly, this should be an HDAC isoform or isoforms, perhaps representing a specific HDAC class. However, it is important to note that HDACis modify many non-histone proteins in their capacity as lysine deacetylases (Buchwald, M., et al. HDACi—targets beyond chromatin. Cancer Lett 280, 160-167, (2009)). These targets include hormone receptors, signal transducers, transcriptions factors, structural proteins, and chaperones. Therefore, target identification may not be a straightforward prospect. However, an investigation of possible HDAC targets still represents the best place to start. These preliminary results suggest that the expression patterns of individual HDAC isoforms remain relatively ubiquitous in 24 hpf zebrafish embryos (data not shown). It may be helpful to determine if any of these become compartmentalized in the pronephric region later in development. These isoforms would be good candidates as potential PTBA effectors. Furthermore, like other carboxylic acid HDACis, PTBA would be expected to exhibit some Class I/IIa specificity. If this characteristic is confirmed in future investigations, then isoforms of these classes should also merit some interest. Morpholino knockdown of these candidates in an effort to recapitulate lhx1a expansion in the IM would provide an excellent approach for target validation. When developing potential human therapeutics using zebrafish, consideration should be given to the variation in HDAC orthologs across species. Although zebrafish hdacs, such as hdac1, share a large degree of amino acid identity with the HDACs of other vertebrates, discrepancies remain (FIG. 35). These differences could alter the efficacy of PTBA or its analogs when applied in other model systems or in humans. Encouragingly, PTBA demonstrated the ability to function in vitro as an HDACi using human HDAC isoforms derived from HeLa cell extracts. However, this result does not eliminate the possibility of differing efficacies when assessing individual HDAC orthologs.

In addition to the points raised above, several other open questions remain unanswered. Potent HDACis, such as SAHA and MS-275, showed no effect on zebrafish embryos when they were treated at 3 µM. This was an unexpected result which could reflect poor absorption of the compounds into the embryos, short half-lives, or a zebrafish-specific effect. Hyperacetylation assays could be performed to determine if the compounds are indeed able to exert a physiological effect on embryos, despite the lack of edemic phenotype. Furthermore, exploring the downstream effects of HDAC inhibition, such as the stimulation of coactivators, would provide further confirmation of the mechanism of PTBA efficacy. For example, pharmacologically inhibiting the activity of histone acetyltransferases (HATs) would be expected to block PTBA efficacy by interfering with its signaling. One final point of interest is better understanding the differences in PTBA efficacy when compared to TSA in the in vitro and in vivo assays. In vitro, TSA is thousands of times more effective than PTBA in inhibiting HDAC activity, while in vivo the difference is greatly reduced. Of course, the varying HDAC class specificities of the two compounds may play a role in this effect. However, the structural elements of PTBA, particularly the thiol group, is suspected to provide the compound with unique in vivo pharmacokinetics.

These results demonstrate that several PTBA analogs exhibit improved efficacy with little to no increase in toxicity. These second generation compounds are excellent candidates to improve renal recovery in future animal studies. However, this work marks only the first steps in the development of this family of compounds. Using only simple functional group substitutions, we were able to identify PTBA structural analogs that were only several times less effective than TSA. However, these same analogs exhibit several hundred times less toxicity than TSA in podocyte cell culture. This represents the key benefit offered by this class of "weak" inhibitors. It is true that almost all of the effective PTBA analogs cause some degree of edemic and/or lethal phenotypes during zebrafish development. However, these teratogenic effects should not be an issue when treating an adult, whose tissues primarily consist of differentiated cells. Indeed, as shown below, PTC-DTR mice treated with m4PTB exhibit no overt signs of toxicity (data not shown). Because the second generation PTBA analogs exhibit little toxicity, there is still ample room for further efficacy improvements. The results of my research offer some guidelines for this process. In general, substitutions of the aliphatic cap region increased compound efficacy. Adding functional groups to the phenyl ring represents a simple way to increase the Log P value of the base compound, which may aid absorption through biological membranes. Alternatively, the cap substitutions may interact with amino acids in the binding pocket of the HDAC, improving the affinity of the compound. Interestingly, even halogenated groups, which are often metabolized into toxic byproducts (Pohl, L. R. et al. Electrophilic halogens as potentially toxic metabolites of halogenated compounds. *Trends Pharmacol Sci* 5, 61-64, (1984)), appear to be tolerable. The sulfur atom forming the connecting unit of PTBA also appears to be an activity determinant. In comparison to its substituted analogs, only PTBA exhibited significant efficacy. Since the Log P values of PTBA and the analogs carrying connecting unit substitutions are similar, it is doubtful that improved absorption plays a role. More likely, the sulfur atom forms unique interactions within the HDAC binding pocket. This may include serving as a hydrogen bond acceptor due to the presence of an unbound electron pair.

Unfortunately, only one analog carrying a linker group was available for testing. Adding a bulky ring structure to the linker decreased the analog's efficacy relative to PTBA. The increased rigidity of the normally flexible hydrophobic chain may explain this effect. It is believed that increasing the length of the linker region remains an untapped opportunity to generate a better analog. Indeed, the linkers of the more potent HDACis, including TSA and SAHA, contain seven and eight carbons respectively. Finally, analogs carrying methylated or hydroxamic zinc-binding groups exhibit improved efficacy. Adding alkyl groups to the zinc-binding group might be expected to interfere with the formation of coordinate bonds with the active site zinc. However, it is likely that the ubiquitous esterases found in target cells hydrolyze and remove the alkyl groups upon absorption. Furthermore, since alkylation prevents deprotonization of the carboxylic acid, these analogs would be expected to be more effective in buffered solutions. The hydroxamic analogs of PTBA also demonstrated improved efficacy, although perhaps not as much as expected. Although they possess stronger zinc-binding groups, they suffer from increased polarity as evidenced by lower Log P values. Therefore, the expected increase in binding affinity may be counterbalanced by decreased absorption. Importantly, the hydroxamic PTBA analogs demonstrate none of the toxicity of TSA in cell culture experiments. Further modifications of these structures, perhaps incorporating some elements of the TSA structure, may yield a family of highly potent compounds.

Example 4

Initial studies, above, used a phenotypic marker of the ability to expand the renal progenitor cell field in larval zebrafish, and identified the first member of a novel class of HDAC inhibitors, PTBA as well as a few structural and functional analogs. These findings form the basis for further study. However, this technology is limited as it is dependent on subjective interpretation of a subtle phenotypic change in the fish. Therefore, in order to develop a more objective and higher content screen, we developed an image-based high-content screen using transgenic zebrafish (Vogt A, et al. Automated image-based phenotypic analysis in zebrafish embryos. Dev Dyn. 2009; 238(3):656-63). For this we first generated transgenic cad17:EGFP zebrafish which express GFP in renal tubular epithelium. By treating zebrafish embryos and allowing them to develop into larvae, we can use Tg(Cad17:EGFP) zebrafish to identify expansion of the renal field. Tg(Cad17:EGFP) zebrafish is a transgenic line that was prepared by isolation of an approximately 5 kb (5066 bp) promoter element and approximately 3 kb (3221 bp) first intron element from the cadherin 17 locus, cloning it into a plasmid along with the enchanced GFP open reading frame and injecting if into zebrafish embryos to established transgenic lines using the meganuclease transgenesis method (Soroldoni et al., Simple and efficient transgenesis with meganuclease constructs in zebrafish, Methods Mol Bio 2009; 546: 117-30.).

Exploiting an object-oriented image analysis methodology that models human cognitive processes, termed Cognition Network Technology (CNT) (Vogt A, et al. Dev Dyn. 2009; 238(3):656-63 and Vogt A, et al. High-content analysis of cancer-cell-specific apoptosis and inhibition of in vivo angiogenesis by synthetic (−)-pironetin and analogs. Chem Biol Drug Des. 2009; 74(4):358-68), we have been able to quantify the size of the fluorescently labeled kidney field in embryos treated with our lead PTBA analogue, m4PTB (FIG. 36). Structure assignment is achieved by detection of regions within the image based on features such as brightness, size, and shape. What permits the identification of biologically meaningful domains (head, tail, yolk, tubules) from those initial features is that a human observer immediately assigns context-specific information to objects based on their knowledge of larval morphology. CNT provides this context by permitting users to assign relational information to image objects through context-dependent classification and segmentation to produce a network of objects and relationships. The method is independent of imaging platform, image format, and phenotype.

Primary and Secondary Zebrafish Screens:

The goal of these studies is to evaluate PTBA analogues with improved activity/toxicity characteristics. Since the lead compound, PTBA, is a carboxylic acid, there are potential stability issues in buffered environments such as blood. It is also desirable to utilize compounds that have effective dose ranges in the nano-molar range, as these are more likely to be useful in vivo. As described above, several PTBA analogs were synthesized, including methyl, n-propyl, and sec-butyl PTBA. The methyl PTBA (m4PTB) analogue, demonstrated an effective dose for the renal progenitor assay in the 800 nM range, and it is shown to be effective in accelerating functional recovery from AKI (see FIG. 39). The efficacy of the new PTBA derivatives relative to that of m4PTB is being evaluated, and those compounds with equal or greater activity of m4PTB can be used in a next phase of the screen.

Considerations in Designing and Synthesizing New PTBA Analogues:

Esterified compounds, such as m4PTB offer desirable characteristics for absorption and distribution in mammals, providing a first avenue of pursuit in analog building. Commercially available thiophenols (i.e., substituted on the phenyl or naphthyl rings) are prepared in order to determine the constraints of electron density and bulk on the aromatic region. A short series of esters designed to extend the biological lifetime of PTBA are prepared (i.e., ethyl, n-propyl, iso-propyl, n-butyl, sec-butyl and tert-butyl). All of these are easily achievable at the gram scale. Two mixed esters of PTBA (and any active phenyl-substituted or naphthyl analogues) are prepared. For the reverse ester, valproic acid ethyl ester is reduced to its alcohol, which is then used to esterify PTBA. Some of these esters contain a chiral carbon in the alcohol-derived portion of the compound (e.g., sec-butyl, valproyl and valproate). Those esters with such chirality, if active, are separated into their enantiomers by HPLC or supercritical fluid chromatography (SFC) using standard techniques and the enatiomers tested for activity. Finally, the free acid forms of PTBA and its phenyl ring-substituted/expanded analogues are converted to their hydroxamide forms via activation of the acid moiety and reaction with hydroxylamine. Based on this combinatorial chemistry, we expect to generate ~200 PTBA analogues for screening using the zebrafish reporter assay. Compounds that prove effective are scaled up for the mouse studies.

Considerations in Screening New Analogues for Renal Progenitor Cell Expansion:

For all second-generation compounds, the cad17:EGFP transgene is used as the primary readout to assay for expansion of kidney field (FIG. 36). PTBA analogues that expand cad17:EGFP expression are subjected to a secondary screen. The secondary screen utilizes two lines, Tg(lhx1a: EGFP) (Swanhart et al., 2010 Characterization of an lhx1a transgenic reporter in zebrafish, Int J Dev Biol 54(4): 731-6) and Tg(pax2a:GFP)(Picker et al., A novel positive transcriptional feedback loop in midbrain-hindbrain boundary development is revealed through analysis of the zebrafish pax2.1 promoter in transgenic lines, Development 2002 129 (13): 3227-39). The lhx1a:EGFP and pax2a:GFP transgenic lines are expressed in renal progenitor cells (see above), and allows confirmation that expansion of the nephric field seen with cad17:EGFP is the result of expansion of renal progenitor cells. The described analog families are expected to result in more than 200 new compounds. While we can handle all the compound dose curves in the lhx1a:EGFP and pax2a:GFP reporter assay, we can employ the Topliss approach for analogue synthesis to initially narrow our focus (Martin Y C, et al. Examination of the utility of the Topliss schemes for analog synthesis. J Med Chem. 1973; 16(5): 578-9). Dosage curves for each new compound are added to Tg(cad17:EGFP) embryos starting an 3 uM as the high dose and using a semi-log curve (1 uM, 600 nM, 300 nM, 60 nM, 30 nM) and assayed for expansion of the nephric mesoderm. Since m4PTB is responsive in the 800 nM range, we focus on second-generation compounds that have lower effective dose. Such compounds are assessed in target efficacy and toxicity assays.

Efficacy and Toxicity Studies in Mice:

Candidate PTBA analogues are subjected to general toxicity and efficacy studies in mice.

Efficacy Studies:

PTBA analogues are soluble in 1% DMSO/water, are administered subcutaneously as a single injection in adult CD1 mice, and kidneys harvested at 12, 24 and 48 hours to evaluate histone acetylation (which should increase with HDACi). PTBA analogs are used at a dose range determined from comparative dose efficacy with m4PTB in the secondary zebrafish screen. Acetylated Histone H3 K9 (Ac—H3 K9) is evaluated, as this is most easily detected by Western blot in nuclear extracts from mouse renal tissues. Preliminary studies compared the effect of Trichostatin A (an established, but toxic HDACi) at an effective dose in the zebrafish screen (0.2 mM) with an equivalent dose of m4PTB (0.8 mM), and then x2 and x4 dose increments (molar concentration in vivo based on estimate uniform distribution relative to body mass of water). 3.4 mg/kg (4×) m4PTB induced maximal expression of Ac—H3 K9 after 24 hours (FIG. 37). This effect was increased compared with TSA or lower doses of m4PTB, so we elected to use this dose of m4PTB (3.4 mg/kg) for AKI studies in mice. For definitive studies, we can compare 1×, 2× and 4× equivalent doses of each new PTBA analogue with 3.4 mg/kg m4PTB, and evaluate renal Ac—H3 K9 at the indicated time points. Studies may be performed on 3 mice/group.

Toxicity Studies:

Having established an effective dose regimen for the PTBA analogue, cumulative toxicity studies are performed in mice over a 7-day period (the duration of treatment). Compound dosages are based on efficacy studies, and only those compounds behaving as well or better than m4PTB are evaluated. Vehicle controls are compared with 3 doses of the compound given at the indicated time intervals (log scale, first dose based on efficacy studies). Mice are sacrificed after 7 days and undergo necropsy and tissue analysis for histological evidence of organ toxicity. In addition renal function (BUN and creatinine), liver function (AST, ALT, ALP, Bilirubin and Albumin) and CBC (WBC, Hb and platelets) from terminal blood samples are evaluated. LFT and CBC are performed through a commercial lab. Studies are performed in 7 mice per treatment limb. Only those compounds showing little to no evidence of toxicity within a log of their effective dosage are further evaluated.

Example 5—The Effect of Second-Generation HDACi on Functional Recovery from AKI in Mice PTC-DTR Model of AKI:

We have developed a mouse model of AKI that is ideally suited for our primary screening studies. Our experience with the more established models (ischemia/reperfusion, HgCl$_2$ and cisplatin) has shown that there is significant variability between mice such that functional studies have to be performed with 10-15 mice per group. Transgenic mice express the diphtheria toxin (DT) receptor, human HB-EGF, in proximal tubular epithelial cells (PTC) using a 2.2 kb fragment of the proximal gGT-1 promotor. Characterization of transgene expression indicates that hHB-EGF is only expressed in PTCs (>95% of cells, data not shown). A single IP injection of DT causes AKI in transgenic but not wild type mice, with dose-dependent PTC injury and increased blood urea nitrogen (BUN, a measure of renal function) that peaks between days 3 and 4 and returns to baseline by day 7 (FIG. 38). Male transgenic mice are more sensitive to DT than female mice, which show a milder and slightly later peak in BUN (see FIG. 39). However, we find reproducibly tight data points in both female and male mice using 5-6 mice per group. Moreover, while BUN returns to baseline after 7 days, there is renal fibrosis at higher doses of DT (FIG. 38, panel D). The latter finding is important since the purpose of this screen is to identify compounds that accelerate tubular regeneration following injury, and in so doing prevent long-term fibrotic sequelae resulting from severe AKI, which is being recognized increasingly as a cause of chronic renal insufficiency.

We evaluated efficacy and effective dosage of a second-generation PTBA analogue, m4PTB, by determining the kinetics of renal Histone H3 K9 acetylation (H3K9Ac) following a single SC injection. We saw maximal induction of H3K9A at 3.4 mg/kg, which persisted for 24 hours (FIG. 37). Therefore, using the PTC-DTR model, we treated female transgenic mice with 3.4 mg/kg m4PTB (or 1% DMSO vehicle) 24 hours after injection with DT (0.1 mg/kg, a dose of that induces relatively mild AKI), and continued with daily m4PTB (or control) injections for 6 days. There was a significant, 30% reduction in peak BUN 4 days after injury in the m4PTB group (FIG. 39). Moreover, while further studies are being performed to determine: 1) whether m4PTB is efficacious in more severe DT-induced AKI; and 2) whether accelerated renal recovery from more severe AKI is associated with reduced renal fibrosis at 4 week, these findings establish m4PTB as our first lead compound for further testing in mouse models of AKI.

Studies performed in male PTC-DTR mice using two different doses of DT predicted to induce mild (0.1 mg/kg) and severe AKI (1 mg/kg) (see FIG. 38), determine whether PTBA analogues have beneficial effect in mild, severe AKI or both. Treatment with the PTBA analogue is initiated 24 hours after DT injection and continued daily thereafter for 7 days. Each study includes 3 groups of mice: 1% DMSO (vehicle), m4PTB at 3.4 mg/kg/day and the new analogue at the dose established from renal histone acetylation studies. Based on our experience using this model seven mice per group are used. Mice have daily BUN assays. If BUN improves significantly (as determined by area under the curve growth curve analysis and post-hoc T-Test with Bonferroni correction), results are validated on the same samples by measuring serum creatinine by HPLC (Yuen P S, Dunn S R, Miyaji T, Yasuda H, Sharma K, Star R A. A simplified method for HPLC determination of creatinine in mouse serum. Am J Physiol Renal Physiol. 2004; 286(6):F1116-9). In addition to measuring BUN, mice are sacrificed at 28 days to evaluate renal fibrosis (trichrome blue and sirius red staining). Quantification of tubular atrophy and fibrotic indices and collagen accumulation from sirius red staining are quantified using the BIQUANT image analysis system. These analyses determine whether the PTBA analogues also reduce long term renal fibrosis following AKI. Compounds that accelerate recovery from AKI as well or better than m4PTB and that also reduce long term fibrosis are moved forward onto the secondary screening studies in mice.

Compounds that accelerate AKI recovery as well or better than m4PTB, and show beneficial effects on post-injury renal fibrosis in our primary screen, will be studied more extensively. This secondary screen will evaluate effects of these compounds using three other models of AKI that reflect the spectrum of disease pathology in human AKI: 1) ischemia/reperfusion; 2) toxin (cisplatin); and 3) sepsis (caecal ligation and perforation). Studies are performed using an outbred strain of mice (CD1) in order to more closely mimic the greater genetic diversity of patients in clinical settings.

Example 6—Additional Models

Caecal Ligation Model of AK:

mice are treated with second generation PTBA analogues 24 hours after injury and outcome determined relative to m4PTB and vehicle. BUN and serum creatinine are evaluated in all the mice, as well as renal histology for fibrosis on follow up where long term survival is feasible (ischemia/reperfusion and cisplatin models), as outlined above. For models showing improved renal function and/or beneficial effects on long term renal fibrosis, additional cohorts of mice are set up to evaluate renal histology pre-injury, at day of peak BUN and 7 days post-injury for renal tubular injury scores, tubular proliferation (BrdU incorporation) and apoptosis indices (TUNEL assay). Details of the specific models are outlined below:

Ischemia/Reperfusion (IR) Injury:

IR injury provides a model of AKI that mimics the effects of hypotension, hypovolemia and aortic surgery on the kidney in humans. Injury occurs in highly metabolically active S3 segment PTCs in the outer stripe of the medulla. The model originally developed in rats has been modified for use in mice (Kennedy S E, Erlich J H. Murine renal ischaemia-reperfusion injury. Nephrology (Carlton). 2008; 13(5):390-6) (19).

Cisplatin-Induced AKI:

There are different models of nephrotoxin-induced AKI. Cisplatin has direct cytotoxic effects on both proximal and distal tubular epithelium (dominant cortical PTCs) and has been used extensively as a model of AKI in mice and rats. Moreover, cisplatin is a chemotherapeutic agent used in the treatment of a variety of different malignancies, so the model has relevance to a human disorder. Mice injected on two consecutive days with 10 mg/kg cisplatin IP develop reproducible and reversible injury over a 7-day course but with reasonable survival (death occurs from bone marrow suppression and AKI) (Bi B, Schmitt R, Israilova M, Nishio H, Cantley L G. Stromal cells protect against acute tubular injury via an endocrine effect. J Am Soc Nephrol. 2007; 18(9):2486-96).

Sepsis (Cecal Ligation and Perforation):

Sepsis is one of the most common causes of AKI in humans, and is a contributory factor in the etiology of AKI in many different settings (including hypotensive AKI). One model that reflects the clinical scenario of sepsis-associated AKI is a surgical model that involves cecal ligation and limited cecal perforation (Doi K, Leelahavanichkul A, Yuen P S, Star R A. Animal models of sepsis and sepsis-induced kidney injury. J Clin Invest. 2009; 119(10):2868-78. PMCID: 2752080). By limiting the length of the ligated cecum, and treating mice with broad-spectrum antibiotics and S/C normal saline each day, mice survive for a period of 5-7 days and reproducibly develop AKI. PTBA analogue treatments are initiated 24 hours after surgery, as outlined above.

Alternatively, the LPS-induced AKI model in which transient AKI is induced by infusion of LPS (Doi K, et al. J Clin Invest. 2009; 119(10):2868-78. PMCID: 2752080) can be used.

PTBA analogues will accelerate the rate of renal recovery in AKI. However, the efficacy of any single compound-based therapy is necessarily limited by the maximal biological activity of their class. Since we know that this class of HDACi improves the rate of recovery following AKI, a complementary approach is to determine if a combination of compounds is more effective than a PTBA analogue alone. This combinatorial approach is a standard clinical methodology for treating disease (Boner G, et al. Combination antihypertensive therapy in the treatment of diabetic nephropathy. Diabetes Technol Ther. 2002; 4(3):313-21) (22). On this basis, by evaluating the effect of sub-optimal levels of the lead PTBA analogue, m4PTB, in combination with either (a) FDA approved drugs or (b) drug-like compounds, we expect to find a combination that can greatly expand the renal progenitor cell population in our zebrafish screen.

Whole-Embryo Combinatorial-Synergism Screen:

We know that m4PTB can cause a measurable expansion of the cad17:EGFP transgene at dose between 800 nM to 1 µM (FIG. 36). In addition, in an renal progenitor cell study using the lhx1a:EGFP transgene, we can start to see expansion of the renal progenitor cell population at doses as low as 600 nM (data not shown). Therefore, a combinatorial-synergism screen is performed by combining 600 nM m4PTB with different compound libraries. As with the second-generation compound screen, the cad17:EGFP transgene is used as the primary readout for expansion of kidney field, and compounds that expand cad17:EGFP expression are subjected to a secondary screen. Those compounds that enhance efficacy of sub-optimal doses of m4PTB are evaluated for combinatorial drug toxicity and efficacy, before progressing to our primary AKI screen.

Compound Selection:

It is important to seek new structures as well as to improve on the activity and selectivity of the current inhibitors we have identified. Therefore, (1) collections of FDA approved drugs or agents with known biological activity are examined and (2) libraries of maximal chemical diversity selected for their drug-like characteristics are interrogated. We have in hand the Library of Pharmacologically Active Compounds (LOPAC), the NCI 400 compound clinical trial set, and the 10,000-member TimTec ActiProbe library. The LOPAC library is extensively used at the UPDDI and contains 1280 compounds with known biological activity, including FDA approved drugs. The NCI 400 compound clinical trial set of FDA approved compounds. (Our original compound was found in the NCI diversity set.) The ActiProbe library was computationally selected by Jarvis-Patrick sampling to represent the chemical diversity of a large 2,000,000 member compound collection, and is biased towards diverse drug-like molecules through cheminformatics filtering including Lipinski Rule parameters.

Screen Outcomes:

We expect to identify a set of compounds that can work in concert with m4PTB to improve post-renal damage recovery. Once a hit is found a dose curve is performed in combination with m4PTB and individually for the new hit. Any compounds that expand the renal progenitor cell population without the aid of m4PTB (not an additive effect, but an independent effect) are just as important as compounds that work in a synergistic manner. If a large number of hits are identified, those that work in combination with m4PTB are priority compounds for assessing in mouse toxicity and efficacy studies. By using m4PTB, any potential hits can be moved quickly though the efficacy and toxicity studies into the PTC-DTR AKI model.

Example 7—Synthesis and Evaluation of PTBA Analogs

Figure 12:
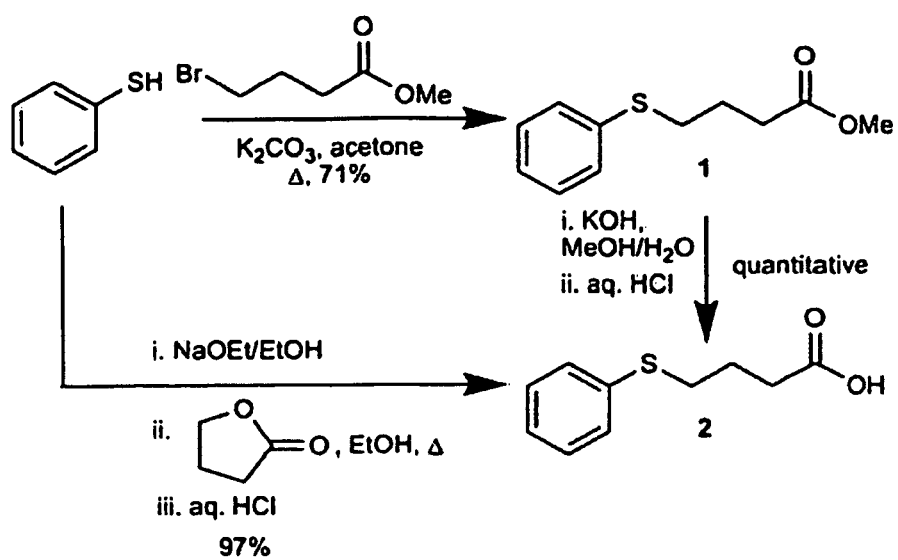
FIG. 12. Synthesis scheme for PTBA

A number of PTBA analogs were synthesized essentially as shown in FIG. 12 and evaluated using a pre-screening method essentially as described above. Physical data, including spectral analysis was performed for a number of the analogs, as indicated below. The following are physical data for various synthesized compounds:

Compound:

VNK-I-154; Yield: 95%; Rf: 0.10 Hex/EA 50:1; Mp, ° C.: colorless oil; $^1$H NMR (CDCl$_3$, 600 MHz): δ: 0.90 (t, J=7.8 Hz, 3H), 1.21 (d, J=6.0 Hz, 3H), 1.50-1.63 (m, 2H, diastereotopic CH$_2$), 1.97 (quintet, J=7.2 Hz, 2H), 2.46 (t, J=7.2 Hz, 2H), 2.98 (t, J=7.2 Hz, 2H), 4.86 (sextet, J=6.6 Hz, 1H), 7.17-7.21 (m, 1H), 7.30 (t, J=7.8 Hz, 2H), 7.36 (dd, J=8.4 Hz, J=1.2 Hz, 2H); $^{13}$C NMR (CDCl$_3$, 150 MHz): δ: 9.73, 19.49, 24.51, 28.80, 32.97, 33.28, 72.29, 126.02, 128.93, 129.30, 136.13, 172.62; HPLC/MS: >95%; HRMS: Calcd. 253.1262, Observed 253.1269.

Compound:

VNK-I-157; Yield: 56%; Rf: 0.30 Hex/EA 9:1; Mp, ° C.: colorless oil; $^1$H NMR (CDCl$_3$, 600 MHz): δ: 1.46 (s, 3H), 1.94 (quintet, J=7.2 Hz, 2H), 2.39 (t, J=7.2 Hz, 2H), 2.97 (t, J=7.2 Hz, 2H), 7.19 (t, J=7.2 Hz, 1H), 7.30 (t, J=7.2 Hz, 2H), 7.36 (d, J=7.2 Hz, 2H); $^{13}$C NMR (CDCl$_3$, 150 MHz): δ: 24.61, 28.11, 32.97, 34.23, 80.40, 125.97, 128.92, 129.25, 136.24, 172.30; HPLC/MS: >95%; HRMS: Calcd. 291.0821, Observed 291.0813.

Compound:

VNK-I-259; Yield: 71%; Rf: 0.10 DCM-MeOH 100:1; Mp, ° C.: white powder 67-68; $^1$H NMR (CDCl$_3$, 600 MHz): δ: (DMSO-d$_6$, 600 MHz), δ 1.77 (quintet, J=7.2 Hz, 2H), 2.09 (t, J=7.2 Hz, 2H), 2.95 (t, J=7.2 Hz, 2H), 7.10-7.20 (m, 1H), 7.25-7.35 (m, 4H), 11.01 (br.s, 1H); $^{13}$C NMR (CDCl$_3$, 150 MHz): δ: 24.90 (CH$_2$), 31.43 (CH$_2$), 31.80 (CH$_2$), 63.61 (CH$_3$), 126.06 (CH), 128.44 (CH), 129.52 (CH), 136.46 (Cq), 168.88 (C=O); HPLC/MS: >95%; HRMS: Calcd. [M+K]264.0461, Observed 264.0423.

Compound:

UPHD-00026; Yield: 78%; Rf: ; Mp, ° C.: colorless oil; $^1$H NMR (CDCl$_3$, 600 MHz): δ: 1.94 (quintet, J=7.2 Hz, 2H), 2.33 (s, 3H), 2.48 (t, J=7.2 Hz, 2H), 2.93 (t, J=7.2 Hz, 2H), 3.68 (s, 3H), 7.12 (d, J=7.8 Hz, 2H), 7.28 (d, J=7.8 Hz, 2H); $^{13}$C NMR (CDCl$_3$, 150 MHz): δ: 21.02, 24.35, 32.59, 33.69, 51.62, 129.72, 130.27, 132.10, 136.30, 173.46; HPLC/MS: >95%; HRMS: n/a.

Compound:

UPHD-00022; Yield: 69%; Rf: 0.18 Hex/EA 5:1; Mp, ° C.: colorless oil; $^1$H NMR (CDCl$_3$, 600 MHz): δ: 1.90 (quintet, J=7.2 Hz, 2H), 2.46 (t, J=7.2 Hz, 2H), 2.86 (t, J=7.2 Hz, 2H), 3.67 (s, 3H), 3.80 (s, 3H), 6.85 (d, J=9.0 Hz, 2H), 7.35 (d, J=9.0 Hz, 2H); $^{13}$C NMR (CDCl$_3$, 150 MHz): δ: 24.40, 32.54, 35.12, 51.61, 55.33, 114.59, 125.91, 133.40, 158.99, 173.50; HPLC/MS: >95%; HRMS: n/a.

Compound:

UPHD-00021; Yield: 97%; Rf: ; Mp, ° C.: colorless oil; $^1$H NMR (CDCl$_3$, 600 MHz): δ: 1.92 (quintet, J=7.2 Hz, 2H), 2.44 (t, J=7.2 Hz, 2H), 2.92 (t, J=7.2 Hz, 2H), 3.65 (s, 3H), 7.20-7.26 (m, 4H); $^{13}$C NMR (CDCl$_3$, 150 MHz): δ: n/a; HPLC/MS: >95%; HRMS: n/a.

Compound:

VNK-I-290; Yield: 98%; Rf: 0.25 Hex/EA 5:1; Mp, ° C.: colorless oil; $^1$H NMR (CDCl$_3$, 600 MHz): δ: 1.94 (quintet, J=7.2 Hz, 2H), 2.46 (t, J=7.2 Hz, 2H), 2.94 (t, J=7.2 Hz, 2H), 3.67 (s, 3H), 7.20 (d, J=8.4 Hz, 2H), 7.39 (d, J=8.4 Hz, 2H); $^{13}$C NMR (CDCl$_3$, 150 MHz): δ: 24.16, 32.51, 32.93, 51.69, 119.85, 130.78, 131.97, 135.28, 173.28; HPLC/MS: >95%; HRMS: Calcd. 288.9898, Observed 288.9873.

Compound:

UPHD-00030; Yield: 98%; 0.27; Hex/EA 5:1; Mp, ° C.: colorless oil; $^1$H NMR (CDCl$_3$, 600 MHz): δ: 1.92 (quintet, J=7.2 Hz, 2H), 2.46 (t, J=7.2 Hz, 2H), 2.91 (t, J=7.2 Hz, 2H), 3.67 (s, 3H), 7.00 (dd, $^3J_{H-H}$=8.4 Hz, $^3J_{H-F}$=8.4 Hz, 2H), 7.35 (dd, $^3J_{H-H}$=8.4 Hz, $^3J_{H-F}$=5.4 Hz, 2H); $^{13}$C NMR (CDCl$_3$, 150 MHz): δ: 24.29, 32.49, 34.27, 51.64, 116.05 (d, $J_{C-F}$=21 Hz), 130.73 (d, $J_{C-F}$=3 Hz), 132.46 (d, $J_{C-F}$=9 Hz), 161.82 (d, $J_{C-F}$=224.5 Hz), 173.36; HPLC/MS: >95%; HRMS: n/a.

Compound:

UPHD-00028; Yield: 52%; Rf: ; Mp, ° C.: white solid; 78-79; $^1$H NMR (CDCl$_3$, 600 MHz): δ: 1.94 (quintet, J=7.2 Hz, 2H), 2.34 (s, 3H), 2.53 (t, J=7.2 Hz, 2H), 2.95 (t, J=7.2 Hz, 2H), 7.12 (d, J=7.2 Hz, 2H), 7.28 (d, J=7.2 Hz, 2H), 10.29 (br.s, 2H); $^{13}$C NMR (CDCl$_3$, 150 MHz): δ: 21.03, 24.03, 32.21, 33.63, 129.75, 130.41, 131.89, 136.45, 177.61; HPLC/MS: >95%; HRMS: Submitted.

Compound:

VNK-I-289; Yield: 71%; Rf: 0.18 Hex/EA 3:1; Mp, ° C.: white solid; 73-75; $^1$H NMR (CDCl$_3$, 600 MHz): δ: 1.90 (quintet, J=7.2 Hz, 2H), 2.52 (t, J=7.2 Hz, 2H), 2.88 (t, J=7.2 Hz, 2H), 3.81 (s, 3H), 6.86 (d, J=9.0 Hz, 2H), 7.36 (d, J=9.0 Hz, 2H), 11.36 (br.s, 2H); $^{13}$C NMR (CDCl$_3$, 150 MHz): δ: 24.06, 32.42, 35.04, 55.34, 114.63, 125.72, 133.52, 159.06, 179.12; HPLC/MS: >95%; HRMS: Calcd. 242.0851, Observed 242.1847.

Compound:

UPHD-00027; Yield: 51%; Rf: ; Mp, ° C.: white solid 107-108; $^1$H NMR (CDCl$_3$, 600 MHz): δ: 1.94 (quintet, J=7.2 Hz, 2H), 2.53 (t, J=7.2 Hz, 2H), 2.96 (t, J=7.2 Hz, 2H), 7.25-7.27 (m, 4H), 10.95 (br.s, 1H); $^{13}$C NMR (CDCl$_3$, 150 MHz): δ: 23.85, 32.29, 33.10, 129.11, 130.82, 132.21, 134.31, 178.32; HPLC/MS: >95%; HRMS: n/a.

Compound:

VNK-I-292; Yield: 56%; Rf: ; Mp, ° C.: white solid 113-114; $^1$H NMR (CDCl$_3$, 600 MHz): δ: (DMSO-d6, 600 MHz), δ 1.76 (quintet, J=7.2 Hz, 2H), 2.35 (t, J=7.2 Hz, 2H), 2.98 (t, J=7.2 Hz, 2H), 7.28 (d, J=8.4 Hz, 2H), 7.48 (d, J=8.4 Hz, 2H), 12.15 (br.s, 2H); $^{13}$C NMR (CDCl$_3$, 150 MHz): δ: (DMSO-d6, 150 MHz), δ 24.39, 31.55, 32.76, 118.83, 130.25, 132.27, 136.23, 174.35; HPLC/MS: >95%; HRMS: Calcd. 289.9850Observed 289.9791.

Compound:

UPHD-00029; Yield: 58%; Rf: ; Mp, ° C.: white solid; ???; $^1$H NMR (CDCl$_3$, 600 MHz): δ: 1.93 (quintet, J=7.2 Hz, 2H), 2.53 (t, J=7.2 Hz, 2H), 2.94 (t, J=7.2 Hz, 2H), 7.02 (dd, $^3J_{H-H}$=8.4 Hz, $^3J_{H-F}$=8.4 Hz, 2H), 7.37 (dd, $^3J_{H-H}$=8.4 Hz, $^3J_{H-F}$=5.4 Hz, 2H), 10.74 (br.s, 1H); $^{13}$C NMR (CDCl$_3$, 150 MHz): δ: 23.94, 32.49, 34.20, 116.10 (d, $J_{C-F}$=21 Hz), 130.54 (d, $J_{C-F}$=3 Hz), 132.60 (d, $J_{C-F}$=7.5 Hz), 161.89 (d, $J_{C-F}$=246 Hz), 179.53; HPLC/MS: >95%; HRMS: n/a;

Example 8—Testing of Selected PTBA Analogs

Testing of the compounds is on-going, but for those tested, Table 6 provides first pass EC$_{50}$s based upon colormetric in situ hybridizations for the Lhx1a mRNA expression levels. After the procedure is run, in situ hybridization is done for the lhx1 mRNA expression and the number of embryos that show an expanded kidney field is manually counted to establish the percent of embryos showing expansion. Then the EC$_{50}$ is determined by plotting the percent expansion in Excel, graphing the results and using the trendline function to determine the 50 percent point. The compounds where there is more than one experiment, the EC$_{50}$ is an average of the multiple EC$_{50}$s generated.

TABLE 6

Renal Cell Expansion and EC$_{50}$ for selected compounds:

| Compound ID | Expansion of Cells (including repeats* and recounts**) | | | | | EC$_{50}$ (μM) |
|---|---|---|---|---|---|---|
| | 200 nM | 400 nM | 800 nM | 1.5 μM | 3 μM | |
| UPHD-00020 | 10% | 10% | 6% | 83% | 92% | 1.4 |
| | 5% | 12% | 47%* | 84%* | 100%* | |
| | | | 31% | 61% | 100% | |
| UPHD-00023 | 0% | 6% | 6 | 92% | 100% | 1.3 |
| | | | 32% | 89% | 100% | |
| UPHD-00029 | 6% | 35% | 60% | 100% | 100% | 1.31 |
| | 6.25% | 0% | 33% | 82.4% | (all uncountable) | |
| UPHD-00028 | 3% | 9% | 61% | 97% | 100% | |
| | 11% | 16% | 56% | 100% | 100% | |
| UPHD-00027 | | | 17% | 97% | 94% | |
| UPHD-00035 | 25% | 10% | 0% | 0% | 21.1% | >3 |
| UPHD-00034 | 16.7% | 10% | 35% | 53% | 0% | |
| | 0% | 9% | 14% | 29% | 9% | |
| UPHD-00050 | ND | ND | 0% | 0% | 0% | >3 |
| UPHD-00051 | 42.1% | 25% | 35.3% | 60% | 86.7% | 1.9* |
| | 6%* | 0%* | 37%* | 45%* | 71%* | |
| | 100% | 0% | 17% | 100% | 80% | |
| UPHD-00041 | ND | ND | 0% | 0% | 0% | >3 |
| UPHD-00042 | 10.5% | 16.7% | 0% | 0% | 10.5% | >3 |
| | 52% | 69% | 69% | 100% | 100% | |
| UPHD-00052 | 0% | 0% | 0% | 10% | 16% | >3 |
| | | | | | 0%** | |
| UPHD-00067 | 17% | 42% | 55% | 21% | 20% | 0.800 |
| | 19% | 15% | 15% | 0% | 30% | |
| UPHD-00061 | 5.5% | 0% | 0% | 6% | 37% | >3 uM |
| UPHD-00059 | 0% | 5% | 12% | 16% | 33% | >3 uM |
| UPHD-00069 | 0% | 0% | 0% | 0% | 0% | >3 uM |
| UPHD-00070 | 0% | 0% | 0% | 0% | 0% | >3 uM |
| UPHD-00024 | 0% | 10% | 19% | 89% | 94% | 1.27 |
| | | | 39% | 85% | 100% | |
| UPHD-00025 | 33% | 37.5% | 21% | 89% | 97% | 0.432 |
| | 30%* | 65%* | 81.3% | 93.8% | All dead | |
| | | | 71%* | 95%* | All dead* | |

TABLE 6-continued

Renal Cell Expansion and EC$_{50}$ for selected compounds:

| Compound ID | 200 nM | 400 nM | 800 nM | 1.5 μM | 3 μM | EC$_{50}$ (μM) |
|---|---|---|---|---|---|---|
| UPHD-00030 | 22% | 26% | 64% | 100% | All dead | 0.485 |
|  | 91% | 100% | 100% | 83% | All dead |  |
|  | 10.5% | 36.8% | 94.7% | uncountable | uncountable |  |
| UPHD-00021 |  |  |  | 72% | 97% |  |
| UPHD-00026 | 3% | 14% | 49% | 100% | 100% |  |
| UPHD-00022 | 16% | 0% | 39% | 83% | 85% | 1.4 |
|  | 3% | 29% | 57% | 91% | 100% |  |
| UPHD-00033 | ND | ND | 0% | 5% | 11% | >3 uM |
| UPHD-00032 | ND | ND | 0% | 0% | 0% | >3 uM |
| UPHD-00047 | 40%* | 50%* | 100% | 100% | 100% | 0.400 |
|  | 0% | 29% | 100%* | 100%* | (14 expanded, |  |
|  | 28%* | 100%* | 100% | 87% | 3 uncountable) |  |
|  |  |  | 94.4%* | 100%* | 100%* |  |
|  |  |  |  |  | 100% |  |
|  |  |  |  |  | 100%* |  |
| UPHD-00048 | 37%* | 69%* | 100% | 100% | 100% | 0.280 |
|  | 43%* | 50%* | 88%* | (15 expanded, | (1 expanded, |  |
|  | 67%* | 75%* | 100%* | 4 uncountable) | 7 uncountable) |  |
|  |  |  |  | 100%* | 100%* |  |
|  |  |  |  | 100%* | 100%* |  |
| UPHD-00090 | 0% | 12% | 25% | 26% | 65% | 2.34 |
| UPHD-00040 | ND | ND | 6% | 15% | 45% | >3 uM |
| UPHD-00039 | ND | ND | 20% | 35% | 11% | >3 uM |
| UPHD-00045 | ND | ND | 17% | 0% | 17% | >3 uM |
| UPHD-00046 | ND | ND | 17% | 30% | 20% | >3 uM |
|  |  |  | (2 expanded, | (3 expanded, | (3 expanded, |  |
|  |  |  | 10 not | 7 not expanded, | 12 not expanded, |  |
|  |  |  | expanded, | 10 uncountable) | 5 uncountable) |  |
|  |  |  | 6 uncountable) |  |  |  |
| UPHD-00057 | 19% | 19% | 11% | 18% | 29% | >3 uM |
| UPHD-00063 | 10% | 5% | 0% | 0% | 6% | >3 uM |
| UPHD-00062 | 11% | 12% | 0% | 0% | 0% | >3 uM |
| UPHD-00058 | 17% | 33% | 20% | 28% | 6% | >3 uM |
| UPHD-00065 | 0% | 20% | 6% | 11% | 29% | >3 uM |
| UPHD-00036 | ND | ND | 45% | 85% | 100% |  |
| UPHD-00038 | ND | ND | 58% | 81% | 85% |  |
| UPHD-00037 | 10%* | 20%* | 0% | 0% | 10% | 2.59** |
|  | 10%** | 0%** | 40%* | 45%* | 80%* |  |
|  |  |  | 20%** | 15%** | 60%** |  |
| UPHD-00049 | 5% | 35% | 60% | 95% | 100% | 0.890 |
| UPHD-00053 | 20% | 5% | 85% | 100% | 100% | 0.790 |
| UPHD-00077 | 40% | 100% | 100% | ND (All Dead) | ND (All Dead) | 0.230 |
| UPHD-00044 | 42%* | 50% | 11% | 40% | 63% | 1.49** |
|  | 16%** | 20%** | 55%* | 80%* | (1 uncountable) |  |
|  |  |  | 35%** | 55%** | 95%* |  |
|  |  |  |  |  | 85%** |  |
| UPHD-00043 | 0%* | 15%* | 5% | 47% | 57% | 3* |
|  |  |  | 0%* | 5%* | 50%* |  |
| UPHD-00073 | 5% | 10% | 0% | 20% | 30% | >3 uM |
| UPHD-00072 | 0% | 0% | 5% | 5% | 5% | >3 uM |
| UPHD-00060 | 5% | 0% | 10% | 20% | 5% | >3 uM |
| UPHD-00066 | 0% | 0% | 5% | 11% | 10% | >3 uM |
| UPHD-00071 | 12% | 42% | 74% | 26% | 70% |  |
| UPHD-00081 | 0% | 10% | 10% | 20% | 32% | >3 uM |

Figure 40A:
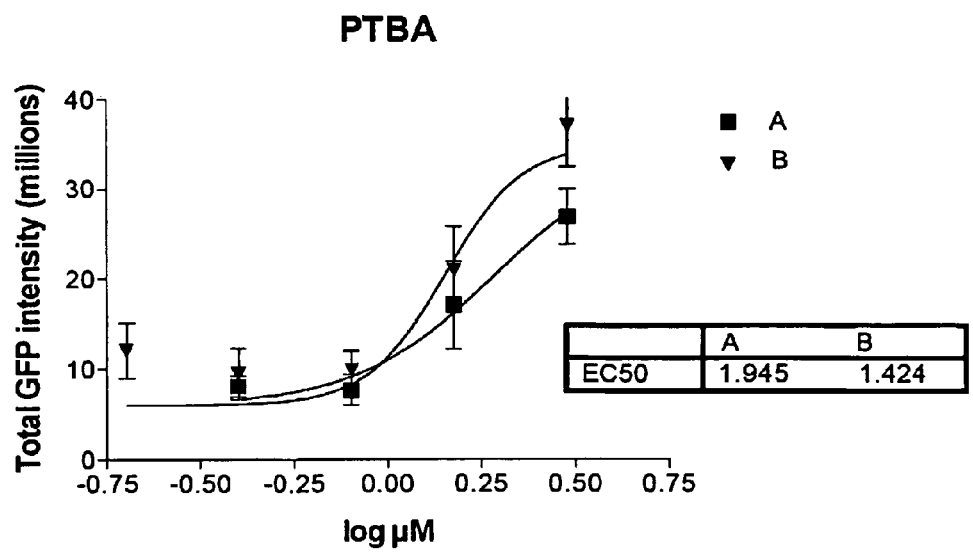
Figure 40B:
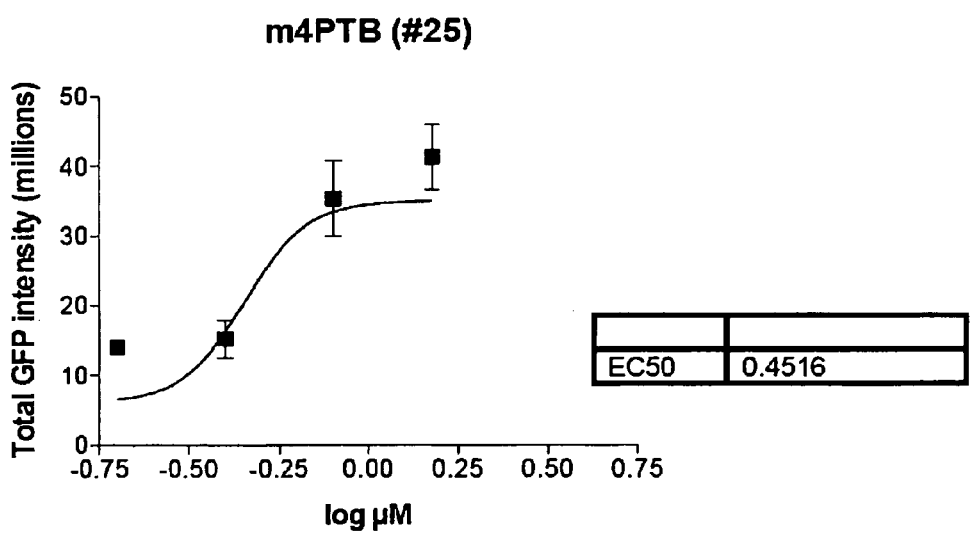

In addition, FIGS. 40A and 40B provide graphs showing EC$_{50}$s for PTBA (FIG. 40A) and m4PTB (FIG. 40B) done via CNT analysis, essentially as described above on the chd17:EGFP transgene. The results are very similar to the EC$_{50}$s provided in Table 6.

Example 9—HgCl$_2$-Induced AKI

FIG. 41 is a graph showing the results of an AKI model using HgCl$_2$ induced injury. The assay is a BUN time course of HgCl$_2$ at 20 mg/kg in BALB/c mice, treated daily after 48 hrs with 3 mg/kg of compound UPHD-00022 (n=5/group).

Example 10—Folic Acid-Induced AKI

FIG. 42 are photomicrographs showing the results of an AKI model using folic acid-induced injury. Folic acid is administered to CD1 mice (n=6/group) intraperitoneally (IP) at 250 mg/ml in 0.3M NaHCO$_3$. Compound UPHD-00022 was injected daily IP at 50 mg/ml in 30% PEG300 vehicle starting 24 hrs after folic acid treatment. Kidney tissue was stained using Trichrome and Sirus Red stained after 15 days. Blue in trichrome and the red in sirus red indicates fibrotic (scar) tissue. As can be seen, a reduction in fibrosis is seen.

Example 11—Gentamycin-Induced AKI

Figures 43A, 43B:
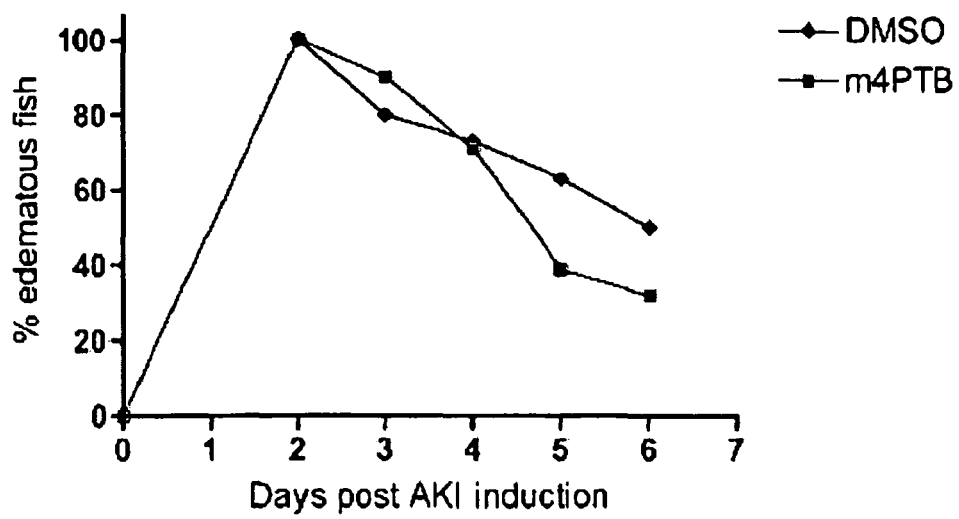

FIG. 43A is a graph showing the results of an AKI model using gentamycin-induced injury. AKI is generated as per a recent publication, Cianciolo Cosenitino, C., et al. ((2010) Intravenous microinjections of zebrafish larvae to study acute kidney injury. JoVE August 4 (42), pii: 2079. doi: 10.3791/2079). Four micromolar m4PTB (UPHD-00025) was added to the zebrafish E3 media in 0.5% DMSO at 2 days post injection of gentamicin and the larvae are scored daily for four days (6 days post injection) as alive or dead, with the final data tallied on day 6 post injection FIG. 43B.

Example 12—m4PTB Treatment Post AKI: Proliferation

Proliferation of renal cells was examined post AKI for m4PTB in zebrafish larvae (FIG. 44). AKI is generated as above with gentamycin, essentially as described in Example 11. Four µM m4PTB was added 2 days post injection of gentamicin. Zebrafish larvae at 5 days post injection were treated for 1 hour with the thymidine analogue EdU (10 milimolar), which incorporates into dividing (proliferating cells) while the larvae are in the zebrafish E3 media. The larvae where then fixed and processed for histology to count the number of proliferating cells in the proximal convulted tubule (as marked by the antibody 3G8). The number of proliferating cells was divided by the total number of cells in the proximal convulted tubule to generate the percent of proliferation also known as the proliferation index as shown in FIG. 44. Renal cell proliferation is significantly increased in the presence of m4PTB.

Whereas particular embodiments of this invention have been described above for purposes of illustration, it will be evident to those skilled in the art that numerous variations of the details of the present invention may be made without departing from the invention as defined in the appended claims.

What is claimed is:

1. A method of improving kidney function in a patient having acute kidney damage, comprising administering to the patient a compound having the formula:

R2—R\R3—C(=O)—R1, in which
R is S;
R1 is —OR5 where R5 is H or $C_{1-4}$ alkyl;
R2 is phenyl or

[R6-substituted phenyl structure], where R6 is halo, $C_{1-4}$ alkyl, or $C_{1-4}$ alkoxy; and
R3 is from 3 to 5 methylene groups ((—CH$_2$—)$_{3-5}$),
or a pharmaceutically acceptable salt thereof in an amount effective to increase renal progenitor cell production in a damaged kidney of the patient.

2. The method of claim 1, in which the amount effective to increase renal progenitor cell production in the renal cells is an amount effective to reduce blood urea nitrogen (BUN) levels in a patient.

3. The method of claim 1, in which the amount effective to increase renal progenitor cell production in the renal cells ranges from 0.05 to 200 mg/kg/day.

4. The method of claim 1, in which the amount effective to increase renal progenitor cell production in the renal cells ranges from 0.05 to 100 mg/kg/day.

5. A method of inhibiting a histone deacetylase in a cell in a patient having acute kidney injury, comprising contacting the cell with a compound having the formula:

R2—R\R3—C(=O)—R1, in which
R is S;
R1 is —OR5 where R5 is H or $C_{1-4}$ alkyl;
R2 is phenyl or

[R6-substituted phenyl structure], where R6 is halo, $C_{1-4}$ alkyl, or $C_{1-4}$ alkoxy; and
R3 is from 3 to 5 methylene groups ((—CH$_2$—)$_{3-5}$),
or a pharmaceutically acceptable salt thereof in an amount effective to inhibit a histone deacetylase in the cell.

6. The method of claim 1, wherein the compound has the formula:

(UPHD-00090)
[4-methoxyphenyl-S-(CH$_2$)$_4$-C(=O)-OMe structure]

or a pharmaceutically acceptable salt thereof.

7. The method of claim 1, wherein the compound has the formula:

(UPHD-00025)
[phenyl-S-(CH$_2$)$_3$-C(=O)-OMe structure]

or a pharmaceutically acceptable salt thereof.

8. The method of claim 1, wherein the compound has the formula:

(UPHD-00030)
[4-fluorophenyl-S-(CH$_2$)$_3$-C(=O)-OMe structure]

or a pharmaceutically acceptable salt thereof.

9. The method of claim 1, wherein the compound has the formula:

(UPHD-00022)
[4-methoxyphenyl-S-(CH$_2$)$_3$-C(=O)-OMe structure]

or a pharmaceutically acceptable salt thereof.

10. The method of claim 1, wherein the compound has the formula:

(UPHD-00047)
[phenyl-S-(CH$_2$)$_4$-C(=O)-OMe structure]

or a pharmaceutically acceptable salt thereof.

11. The method of claim 5, wherein the compound has the formula:

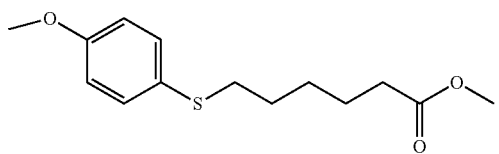
(UPHD-00090)

or a pharmaceutically acceptable salt thereof.

12. The method of claim 5, wherein the compound has the formula:

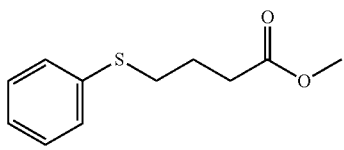
(UPHD-00025)

or a pharmaceutically acceptable salt thereof.

13. The method of claim 5, wherein the compound has the formula:

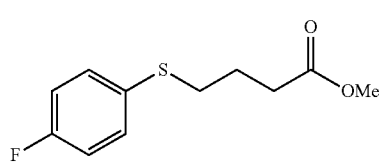
(UPHD-00030)

or a pharmaceutically acceptable salt thereof.

14. The method of claim 5, wherein the compound has the formula:

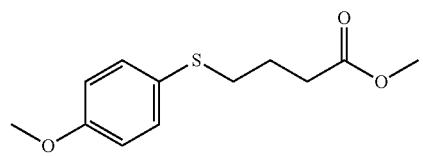
(UPHD-00022)

or a pharmaceutically acceptable salt thereof.

15. The method of claim 5, wherein the compound has the formula:

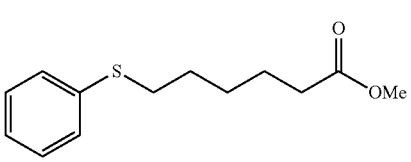
(UPHD-00047)

or a pharmaceutically acceptable salt thereof.

16. A method of improving kidney function in a patient having acute kidney damage, comprising administering to the patient a compound having the formula:

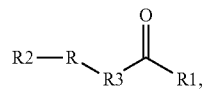

in which

R is S;

R1 is —OR5, where R5 is $C_{1-4}$ alkyl;

R2 is phenyl or

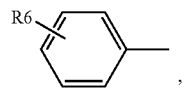

where R6 is halo, $C_{1-4}$ alkyl, or $C_{1-4}$ alkoxy and;

R3 is from 3 to 5 methylene groups ((—$CH_2$—)$_{3-5}$), or a pharmaceutically acceptable salt thereof in an amount effective to increase renal progenitor cell production in a damaged kidney of the patient.

* * * * *

UNITED STATES PATENT AND TRADEMARK OFFICE
CERTIFICATE OF CORRECTION

PATENT NO. : 10,160,705 B2
APPLICATION NO. : 13/982512
DATED : December 25, 2018
INVENTOR(S) : Billy W. Day et al.

Page 1 of 1

It is certified that error appears in the above-identified patent and that said Letters Patent is hereby corrected as shown below:

In the Specification

Column 1, Lines 22 through 25, under STATEMENT REGARDING FEDERAL FUNDING, delete "This invention was made with government support under Grant Nos. DK069403 and DK053287 awarded by the National Institutes of Health. The government has certain rights in the invention." and insert -- This invention was made with government support under grant numbers DK069403 and HD053297 awarded by the National Institutes of Health The government has certain rights in the invention. --

Signed and Sealed this
Twenty-sixth Day of March, 2019

Andrei Iancu
*Director of the United States Patent and Trademark Office*

SEQUENCE LISTING

<160> NUMBER OF SEQ ID NOS: 13

<210> SEQ ID NO 1
<211> LENGTH: 19
<212> TYPE: DNA
<213> ORGANISM: Danio rerio

<400> SEQUENCE: 1
cgtgctgtct tcccatcca                                                19

<210> SEQ ID NO 2
<211> LENGTH: 26
<212> TYPE: DNA
<213> ORGANISM: Danio rerio

<400> SEQUENCE: 2
ttcatactat ggagattatc aaagcg                                        26

<210> SEQ ID NO 3
<211> LENGTH: 22
<212> TYPE: DNA
<213> ORGANISM: Danio rerio

<400> SEQUENCE: 3
ggtcctgatg agggaacaaa ag                                            22

<210> SEQ ID NO 4
<211> LENGTH: 20
<212> TYPE: DNA
<213> ORGANISM: Danio rerio

<400> SEQUENCE: 4
gtccctggaa gcgactttc                                                20

<210> SEQ ID NO 5
<211> LENGTH: 18
<212> TYPE: DNA
<213> ORGANISM: Danio rerio

<400> SEQUENCE: 5
ttgactgggc tgcgatgg                                                 18

<210> SEQ ID NO 6

```
<211> LENGTH: 18
<212> TYPE: DNA
<213> ORGANISM: Danio rerio

<400> SEQUENCE: 6
gctccgccgt cactcctc                                                  18

<210> SEQ ID NO 7
<211> LENGTH: 22
<212> TYPE: DNA
<213> ORGANISM: Danio rerio

<400> SEQUENCE: 7
tctcctggtc actgtcatcg tg                                             22

<210> SEQ ID NO 8
<211> LENGTH: 24
<212> TYPE: DNA
<213> ORGANISM: Danio rerio

<400> SEQUENCE: 8
cgcagcacta ccaccaataa ctac                                           24

<210> SEQ ID NO 9
<211> LENGTH: 21
<212> TYPE: DNA
<213> ORGANISM: Danio rerio

<400> SEQUENCE: 9
gagcctgatg gggtgagagt c                                              21

<210> SEQ ID NO 10
<211> LENGTH: 25
<212> TYPE: DNA
<213> ORGANISM: Danio rerio

<400> SEQUENCE: 10
ttctggaaca ttacagtgga gactc                                          25

<210> SEQ ID NO 11
<211> LENGTH: 20
<212> TYPE: DNA
<213> ORGANISM: Danio rerio

<400> SEQUENCE: 11
gtgcgtcagc atttggtgtg                                                20

<210> SEQ ID NO 12
<211> LENGTH: 20
<212> TYPE: DNA
<213> ORGANISM: Danio rerio

<400> SEQUENCE: 12
cggaaaaggc tctccaacag                                                20

<210> SEQ ID NO 13
<211> LENGTH: 22
<212> TYPE: DNA
<213> ORGANISM: Danio rerio

<400> SEQUENCE: 13
tgctggtggg tcctaatatc tg                                             22
```